United States Patent
Fischer et al.

(10) Patent No.: US 9,550,739 B2
(45) Date of Patent: Jan. 24, 2017

(54) MOLECULES HAVING CERTAIN PESTICIDAL UTILITIES, AND INTERMEDIATES, COMPOSITIONS, AND PROCESSES RELATED THERETO

(71) Applicant: Dow AgroSciences LLC, Indianapolis, IN (US)

(72) Inventors: Lindsey G. Fischer, Indianapolis, IN (US); Gary D. Crouse, Noblesville, IN (US); Thomas C. Sparks, Greenfield, IN (US); Miriam E. Goldsmith, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/810,775

(22) Filed: Jul. 28, 2015

(65) Prior Publication Data
US 2016/0024026 A1    Jan. 28, 2016

Related U.S. Application Data

(60) Provisional application No. 62/029,763, filed on Jul. 28, 2014.

(51) Int. Cl.
*C07D 249/08*    (2006.01)
*C07D 401/12*    (2006.01)
*A01N 43/653*    (2006.01)

(52) U.S. Cl.
CPC .......... *C07D 249/08* (2013.01); *A01N 43/653* (2013.01); *C07D 401/12* (2013.01)

(58) Field of Classification Search
CPC ... C07D 249/08; C07D 213/56; C07D 401/12; A01N 43/653
See application file for complete search history.

(56) References Cited

U.S. PATENT DOCUMENTS

2016/0024027 A1 * 1/2016 Fischer ............... C07D 249/08
504/100

FOREIGN PATENT DOCUMENTS

WO    WO2014/004064 A1 *    1/2014    .......... C07D 403/12

* cited by examiner

*Primary Examiner* — Jane C Oswecki
(74) *Attorney, Agent, or Firm* — Yung H. Lee; Carl D. Corvin

(57) ABSTRACT

This disclosure relates to the field of molecules having pesticidal utility against pests in Phyla Nematoda, Arthropoda, and/or Mollusca, processes to produce such molecules and intermediates used in such processes, compositions containing such molecules, and processes of using such molecules against such pests. These molecules may be used, for example, as nematicides, acaricides, insecticides, miticides, and/or molluscicides. This document discloses molecules having the following formula ("Formula One").

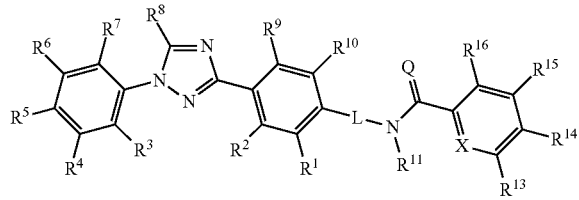

3 Claims, No Drawings

MOLECULES HAVING CERTAIN PESTICIDAL UTILITIES, AND INTERMEDIATES, COMPOSITIONS, AND PROCESSES RELATED THERETO

CROSS REFERENCE TO RELATED APPLICATIONS

This application claims the benefit of, and priority from, U.S. Provisional Patent Application Ser. No. 62/029,763 filed 28 Jul. 2014, the entire disclosure of which is hereby expressly incorporated by reference.

FIELD OF THE DISCLOSURE

This disclosure relates to the field of molecules having pesticidal utility against pests in Phyla Nematoda, Arthropoda, and Mollusca, processes to produce such molecules and intermediates used in such processes, compositions containing such molecules, and processes of using such molecules against such pests. These molecules may be used, for example, as nematicides, acaricides, insecticides, miticides, and molluscicides.

BACKGROUND OF THE DISCLOSURE

"Many of the most dangerous human diseases are transmitted by insect vectors" (Rivero, A. et al., Insect Control of Vector-Borne Diseases: When is Insect Resistance a Problem? Public Library of Science Pathogens, 6(8) (2010)). Historically, vector-borne diseases, such as, malaria, dengue, yellow fever, plague, and louse-borne typhus, among others, were responsible for more human disease and death from the 1600's through the early 1900's than all other causes combined (Gubler D., Resurgent Vector-Borne Diseases as a Global Health Problem, Emerging Infectious Diseases, Vol. 4, No. 3, July-September (1998)). Currently, vector-borne diseases are responsible for about 17% of the global parasitic and infectious diseases. It has been estimated that about 250 million people around the world have malaria and about 800,000 deaths occur each year—85% of those deaths are children under the age of five. A further 250,000 to 500,000 cases of dengue hemorrhagic fever occur each year (Matthews, G., Integrated Vector Management: controlling vectors of malaria and other insect vector borne diseases (2011)). Vector control plays a critical role in the prevention and control of infectious diseases. However, insecticide resistance, including resistance to multiple insecticides, has arisen in all insect species that are major vectors of human diseases (Rivero, A. et al.).

Each year insects, plant pathogens, and weeds destroy more than 40% of all potential food production. This loss occurs despite the application of pesticides and the use of a wide array of non-chemical controls, such as crop rotations and biological controls. If just some of this food could be saved, it could be used to feed the more than three billion people in the world who are malnourished (Pimental, D., Pest Control in World Agriculture, Agricultural Sciences—Vol. II (2009)).

Plant parasitic nematodes are among the most widespread pests, and are frequently one of the most insidious and costly. It has been estimated that losses attributable to nematodes are from about 9% in developed countries to about 15% in undeveloped countries. However, in the United States of America, a survey of 35 States on various crops indicated nematode-derived losses of up to 25% (Nicol, J. et al., Current Nematode Threats to World Agriculture, Genomic and Molecular Genetics of Plant—Nematode Interactions (Eds. Jones, J. et al.), Chapter 2, (2011)).

It is noted that gastropods (slugs and snails) are pests of less economic importance than insects or nematodes, but in certain areas, gastropods may reduce yields substantially, severely affecting the quality of harvested products, as well as transmitting human, animal, and plant diseases. While only a few dozen species of gastropods are serious regional pests, a handful of species are important pests on a world-wide scale. In particular, gastropods affect a wide variety of agricultural and horticultural crops, such as arable, pastoral, and fiber crops; vegetables; bush and tree fruits; herbs; and ornamentals (Speiser, B., Molluscicides, Encyclopedia of Pest Management (2002)).

Termites cause damage to all kinds of private and public structures, as well as to agricultural and forestry resources. In 2003, it was estimated that termites cause over US$20 billion in damage world-wide each year (Su, N. Y., Overview of the global distribution and control of the Formosan subterranean termite, *Sociobiology* 2003, 41, 177-192).

Therefore, for many reasons, including the above reasons, a need exists for new pesticides.

DEFINITIONS

The examples given in the definitions are generally non-exhaustive and must not be construed as limiting the molecules disclosed in this document. It is understood that a substituent should comply with chemical bonding rules and steric compatibility constraints in relation to the particular molecule to which it is attached.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, propyl, isopropyl, butyl, and tert-butyl.

"Alkynyl" means an acyclic, unsaturated (at least one carbon-carbon triple bond), branched or unbranched, substituent consisting of carbon and hydrogen, for example, ethynyl, propargyl, butynyl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbornyl, bicyclo [2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo [2.2.2]octyloxy.

"Halo" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. Examples of aromatic heterocyclyls include, but are not limited to, benzofuranyl, benzoisothiazolyl, benzoisoxazolyl, benzoxazolyl, benzothienyl, benzothiazolyl, cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, tetrahydrofuranyl, and tetrahydropyranyl. Examples of partially unsaturated heterocyclyls include, but are not limited to, 1,2,3,4-tetrahydro-quinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

DETAILED DESCRIPTION OF THE DISCLOSURE

This document discloses molecules having the following formula ("Formula One")

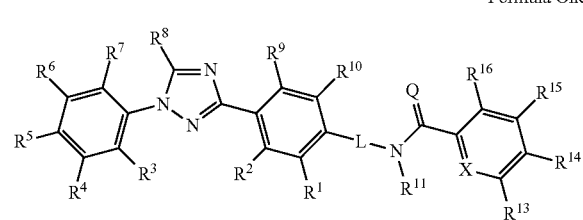

Formula One wherein:

(A) $R^1$, $R^2$, $R^3$, $R^4$, $R^5$, $R^6$, $R^7$, $R^9$, $R^{10}$, $R^{14}$, $R^{15}$, and $R^{16}$ is each independently selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, or $C_3$-$C_6$ cycloalkenyloxy, wherein each alkyl, alkenyl, alkenyloxy, alkynyl, alkynyloxy, haloalkyl, alkoxy, haloalkoxy, cycloalkyl, cycloalkoxy, cycloalkenyl, or cycloalkenyloxy, are optionally substituted with one or more substituents independently selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, or $C_3$-$C_6$ cycloalkenyloxy;

(B) $R^8$ is H;

(C) L is a linker that is bond connecting nitrogen to the carbon in the ring, or L is a $C_1$-$C_4$ alkyl that is optionally substituted with one or more substituents independently selected from a group consisting of F, Cl, CN, OH, or oxo;

(D) $R^{11}$ is selected from H, $(C_1$-$C_4)$alkyl, $(C_2$-$C_4)$alkenyl, $(C_2$-$C_4)$alkenyloxy, $(C_2$-$C_4)$alkynyl, $(C_2$-$C_4)$alkynyloxy, $(C_1$-$C_4)$haloalkyl, $(C_1$-$C_4)$alkoxy, $(C_1$-$C_4)$haloalkoxy, $(C_1$-$C_4)$alkyl $(C_1$-$C_4)$alkoxy, $(C_3$-$C_6)$cycloalkyl, $(C_3$-$C_6)$cycloalkoxy, $(C_3$-$C_6)$cycloalkenyl, $(C_3$-$C_6)$cycloalkenyloxy, $((C_1$-$C_4)$alkyl)) $(C_3$-$C_6)$cycloalkyl), $C(O)(C_1$-$C_4)$alkyl, $C(O)$phenyl, $((C_1$-$C_4)$alkyl)$C(O)(C_1$-$C_4)$alkyl, and $((C_1$-$C_4)$ alkyl)$C(O)O((C_1$-$C_4)$alkyl), wherein each alkyl, alkenyl, alkenyloxy, alkynyl, alkynyloxy, haloalkyl, alkoxy, haloalkoxy, cycloalkyl, cycloalkoxy, cycloalkenyl, cycloalkenyloxy, and phenyl, are optionally substituted with one or more substituents independently selected from H, F, Cl, Br, I, CN, $NO_2$, OH, oxo, and $OC(O)(C_1$-$C_4)$alkyl;

(E) X is selected from N or $CR^{12}$, wherein $R^{12}$ is selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, or $C_3$-$C_6$ cycloalkenyloxy;

(F) $R^{13}$ is selected from a group consisting of H, phenyl, or substituted phenyl, wherein said substituted phenyl is substituted with one or more substituents independently selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, $C_3$-$C_6$ cycloalkenyloxy, $OC_1$-$C_4$ alkylphenyl, $C(O)C_1$-$C_4$ alkyl, or $N(C_1$-$C_4$ alkyl)($C_1$-$C_4$ alkyl);

(G) Q is selected from O or S.

In another embodiment $R^5$ is $C_1$-$C_4$ haloalkyl, $C_1$-$C_4$ alkoxy, or $C_1$-$C_4$ haloalkoxy. This embodiment may be used in combination with the other embodiments of $R^1$, $R^2$, $R^3$, $R^4$, $R^6$, $R^7$, $R^8$, $R^9$, $R^{10}$, $R^{11}$, $R^{13}$, $R^{14}$, $R^{15}$, $R^{16}$, X, Q, and L.

In another embodiment $R^5$ is $CF_3$, $OCH(CH_3)_2$, $OCF_3$, or $OCF_2CF_3$. This embodiment may be used in combination with the other embodiments of $R^1$, $R^2$, $R^3$, $R^4$, $R^6$, $R^7$, $R^8$, $R^9$, $R^{10}$, $R^{11}$, $R^{13}$, $R^{14}$, $R^{15}$, $R^{16}$, X, Q, and L.

In another embodiment L is $C_1$-$C_4$ alkyl. This embodiment may be used in combination with the other embodiments of $R^1$, $R^2$, $R^3$, $R^4$, $R^6$, $R^7$, $R^8$, $R^9$, $R^{10}$, $R^{11}$, $R^{13}$, $R^{14}$, $R^{15}$, $R^{16}$, X, and Q.

In another embodiment L is a bond, —$CH_2$—, or —$CH_2CH_2$—. This embodiment may be used in combination with the other embodiments of $R^1$, $R^2$, $R^3$, $R^4$, $R^6$, $R^7$, $R^8$, $R^9$, $R^{10}$, $R^{11}$, $R^{13}$, $R^{14}$, $R^{15}$, $R^{16}$, X, and Q.

In another embodiment $R^{11}$ is H, $C_1$-$C_4$ alkyl, $C_1$-$C_4$ alkyl $C_3$-$C_6$ cycloalkyl, or $C(O)C_1$-$C_4$ alkyl. This embodiment may be used in combination with the other embodiments of $R^1$, $R^2$, $R^3$, $R^4$, $R^5$, $R^6$, $R^7$, $R^8$, $R^9$, $R^{10}$, $R^{13}$, $R^{14}$, $R^{15}$, $R^{16}$, X, Q, and L.

In another embodiment $R^{11}$ is $CH_3$, $CH_2CH_3$, $CH_2CH_2CH_3$, $CH_2$(cyclopropyl), or $C(O)CH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{13}$, $R^{14}$, $R^{15}$, $R^{16}$, X, Q, and L.

In another embodiment Q is O. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, X, and L.

In another embodiment Q is S. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^3$, $R^{14}$, $R^{15}$, $R^{16}$, X, and L.

In another embodiment X is N. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^3$, $R^{14}$, $R^{15}$, $R^{16}$, Q, and L.

In another embodiment X is $CR^{12}$ wherein $R^{12}$ is H or $C_1$-$C_4$ alkyl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, Q, and L.

In another embodiment X is $CR^{12}$ wherein $R^{12}$ is $CH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, Q, and L.

In another embodiment $R^{13}$ is H or phenyl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{14}$, $R^{15}$, $R^{16}$, X, Q, and L.

In another embodiment $R^{13}$ is substituted phenyl that is substituted with one or more substituents selected from the group consisting of H, F, Cl, $C_1$-$C_4$ alkyl, $C_1$-$C_4$ alkoxy, $C_1$-$C_4$ haloalkoxy, $OC_1$-$C_4$ alkyl phenyl, $C(O)C_1$-$C_4$ alkyl, or $N(C_1$-$C_4$ alkyl)($C_1$-$C_4$ alkyl). This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{14}$, $R^{15}$, $R^{16}$, X, Q, and L.

In another embodiment $R^{13}$ is substituted phenyl that is substituted with one or more substituents selected from the group consisting of $CH_3$, $CH_2CH_3$, $OCH_3$, $OCH_2CH_3$, $OCF_3$, $OCH_2C_6H_5$, $C(O)CH_3$, or $N(CH_3)_2$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{14}$, $R^{15}$, $R^{16}$, X, Q, and L.

In another embodiment $R^{14}$ is H, F, Cl, or $C_1$-$C_4$ alkoxy. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{15}$, $R^{16}$, X, Q, and L.

In another embodiment $R^{14}$ is $OCH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{15}$, $R^{16}$, X, Q, and L.

In another embodiment $R^{15}$ is H, F, or Cl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{16}$, X, Q, and L.

In another embodiment $R^{16}$ is H, F, or Cl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, X, Q, and L.

In another embodiment
(A) $R^1$, $R^2$, $R^3$, $R^4$, $R^5$, $R^6$, $R^7$, $R^9$, $R^{10}$, $R^{14}$, $R^{15}$, and $R^{16}$ is each independently selected from a group consisting of H, F, Cl, Br, I, $C_1$-$C_4$ haloalkyl, $C_1$-$C_4$ alkoxy, or $C_1$-$C_4$ haloalkoxy;
(B) $R^8$ is H;
(C) L is a bond or $C_1$-$C_4$ alkyl;
(D) $R^{11}$ is independently selected from a group consisting of H, $C_1$-$C_4$ alkyl, $C_1$-$C_4$ alkyl $C_3$-$C_6$ cycloalkyl, or $C(O)$ $C_1$-$C_4$ alkyl;
(E) X is selected from N or $CR^{12}$, wherein $R^{12}$ is selected from a group consisting of H or $C_1$-$C_4$ alkyl;
(F) $R^{13}$ is selected from a group consisting of H, phenyl, or substituted phenyl,
wherein said substituted phenyl is substituted with one or more substituents independently selected from a group consisting of H, F, Cl, Br, I, $C_1$-$C_4$ alkyl, $C_1$-$C_4$ alkoxy, $C_1$-$C_4$ haloalkoxy, $OC_1$-$C_4$ alkyl phenyl, $C(O)C_1$-$C_4$ alkyl, or $N(C_1$-$C_4$ alkyl)($C_1$-$C_4$ alkyl);
(G) Q is selected from O or S.

In another embodiment
(A) $R^1$, $R^2$, $R^3$, $R^4$, $R^5$, $R^6$, $R^7$, $R^9$, $R^{10}$, $R^{14}$, $R^{15}$, and $R^{16}$ is each independently selected from a group consisting of H, F, Cl, Br, I, $C_1$-$C_4$ haloalkyl, $C_1$-$C_4$ alkoxy, or $C_1$-$C_4$ haloalkoxy;
(B) $R^8$ is H;
(C) L is a bond or $C_1$-$C_4$ alkyl;
(D) $R^{11}$ is independently selected from a group consisting of H, $C_1$-$C_4$ alkyl, $C_1$-$C_4$ alkyl $C_3$-$C_6$ cycloalkyl, or $C(O)$ $C_1$-$C_4$ alkyl;
(E) X is $CR^{12}$, wherein $R^{12}$ is selected from a group consisting of H or $C_1$-$C_4$ alkyl;
(F) $R^{13}$ is a phenyl or substituted phenyl,
wherein said substituted phenyl is substituted with one or more substituents independently selected from a group consisting of H, F, Cl, Br, I, $C_1$-$C_4$ alkyl, $C_1$-$C_4$ alkoxy, $C(O)$ $C_1$-$C_4$ alkyl, or $N(C_1$-$C_4$ alkyl)($C_1$-$C_4$ alkyl);
(G) Q is selected from O or S.

In another embodiment
(A) $R^1$, $R^2$, $R^3$, $R^4$, $R^5$, $R^6$, $R^7$, $R^9$, $R^{10}$, $R^{14}$, $R^{15}$, and $R^{16}$ is each independently selected from a group consisting of H, F, Cl, Br, I, $C_1$-$C_4$ haloalkyl, $C_1$-$C_4$ alkoxy, or $C_1$-$C_4$ haloalkoxy;
(B) $R^8$ is H;
(C) L is a bond or $C_1$-$C_4$ alkyl;
(D) $R^{11}$ is independently selected from a group consisting of H, $C_1$-$C_4$ alkyl, or $C(O)C_1$-$C_4$ alkyl;
(E) X is $CR^{12}$, wherein $R^{12}$ is H;
(F) $R^{13}$ is a phenyl or substituted phenyl,
wherein said substituted phenyl is substituted with one or more substituents independently selected from a group consisting of H, F, Cl, Br, I, $C_1$-$C_4$ alkyl, $C_1$-$C_4$ alkoxy, $C(O)$ $C_1$-$C_4$ alkyl, or $N(C_1$-$C_4$ alkyl)($C_1$-$C_4$ alkyl);
(G) Q is selected from O or S.

Preparation of Amides

The amide products of Formula One can be prepared from the corresponding amine (1-3), wherein $R^1$, $R^2$, $R^3$, $R^4$, $R^5$, $R^6$, $R^7$, $R^8$, $R^9$, and $R^{10}$ are as previously defined, and acid chloride (1-2), wherein X, $R^{13}$, $R^{14}$, $R^{15}$, and $R^{16}$ are as previously defined. Usually, these acid chlorides can be generated and isolated from a suitable precursor and used directly without purification in the preparation of the amide. One such suitable precursor is a carboxylic acid (1-1) which can be converted into an acid chloride by using a reagent such as oxalyl chloride in a polar aprotic solvent such as dichloromethane or tetrahydrofuran, in the presence of a catalytic amount of dimethylformamide, at temperatures from about −78° C. to about 30° C. (Scheme 1, step a), followed by removal of solvent by concentration.

Scheme 1

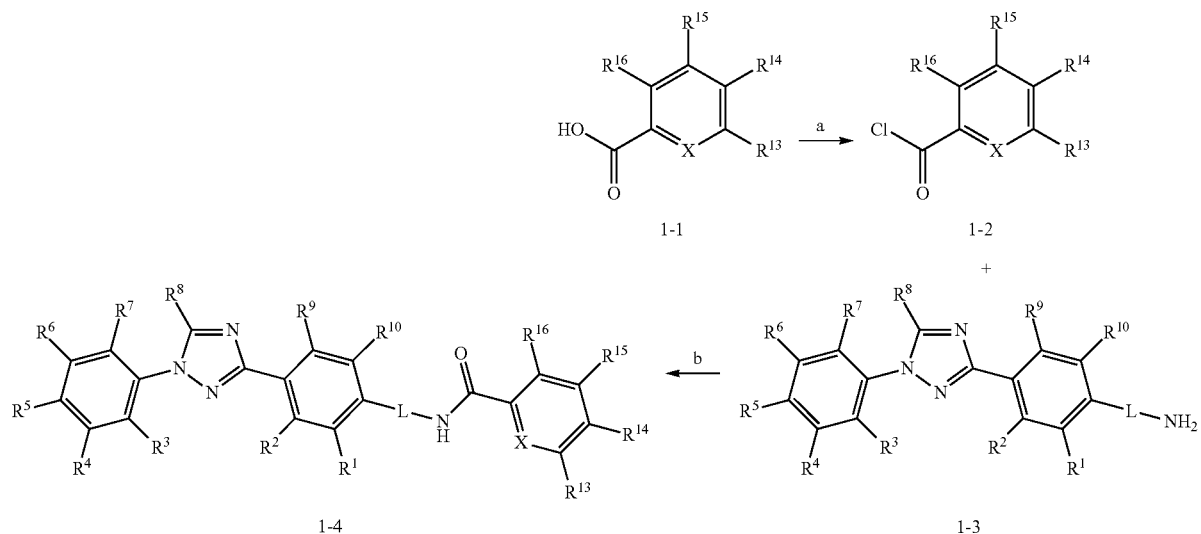

Alternatively, the carboxylic acid can also be converted into an acid chloride by treatment with thionyl chloride in a non-polar aprotic solvent such as toluene, at temperatures from about −10° C. to about 110° C., followed by removal of solvent by methods such as concentration or distillation. Accordingly, it is appreciated that the acid chloride may not always be fully characterized, but may simply be used directly without characterization, to generate the amide.

The acid chloride (1-2) can be treated directly with an aniline or amine (1-4) in the presence of an amine base such as diisopropylethylamine, resulting in the formation of an amide (1-4, Scheme 1, step b). The reaction can be performed at temperatures from about −10° C. to about 30° C., preferably from about 15° C. to about 25° C., in an aprotic solvent chosen from tetrahydrofuran, dichloromethane, toluene, but use of tetrahydrofuran is preferred.

Alternatively, an amine, (1-3), can be coupled directly to a carboxylic acid, (1-1) with an activating group such as dicyclohexylcarbodiimide, diisopropylcarbodiimide, or 1-ethyl-3-(3-dimethylaminopropyl)carbodiimide, and a triazole such as 1-hydroxy-benzotriazole or 1-hydroxy-7-azabenzotriazole, in the presence of an amine base such as diisopropylethylamine or triethylamine, in a polar aprotic solvent such as dimethylformamide, tetrahydrofuran, or dichloromethane, at temperatures from about −10° C. to about 30° C. (Scheme 2). The reaction can also be facilitated with uronium or phosphonium activating groups such as O-(7-azabenzotriazol-1-yl)-N,N,N',N'-tetramethyluronium hexafluorophosphate or benzotriazol-1-yl-oxytripyrrolidinophosphonium hexafluorophosphate, in the presence of an amine base such as diisopropylethylamine or triethylamine, in a polar aprotic solvent such as dimethylformamide, tetrahydrofuran, or dichloromethane, at temperatures from about −10° C. to about 30° C. to form the amide (1-4).

Scheme 2

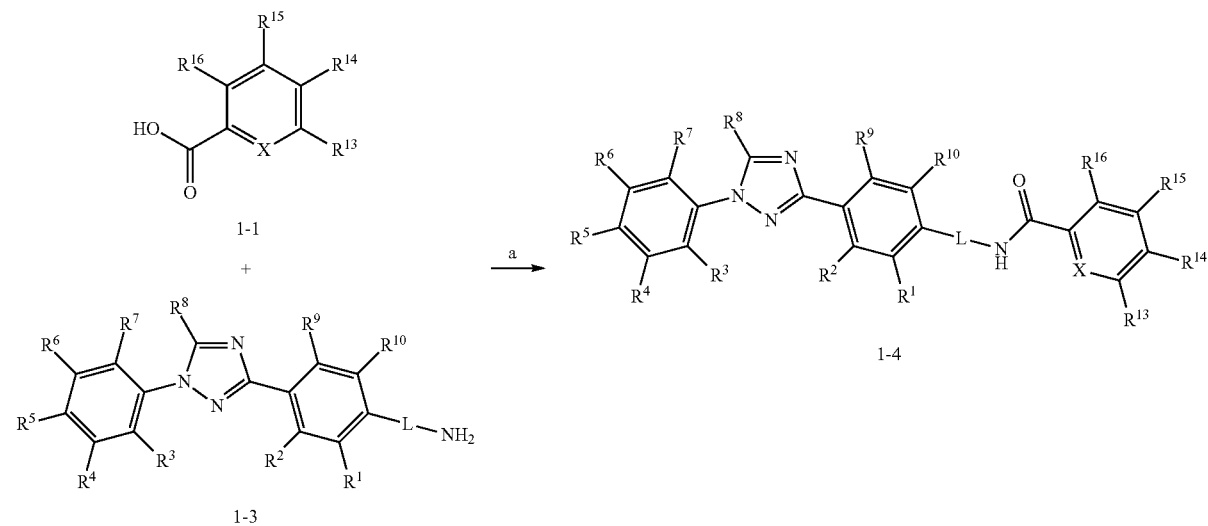

Preparation of N-Alkyl or N-Acyl Amides

The N-alkyl or N-acyl amide products (3-2, Scheme 3) of Formula One, wherein $R^{11}$ is as previously defined, may be prepared from the corresponding amide (1-4). The amide can be treated directly with an inorganic base such as sodium hydride, in a polar aprotic solvent such as dimethylformamide or tetrahydrofuran, at temperatures from about −10° C. to about 30° C., followed by treatment with an alkyl source such as

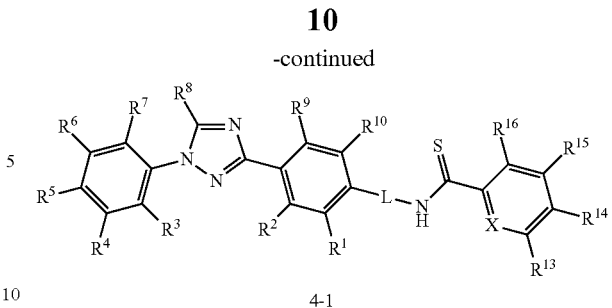

4-1

Scheme 3

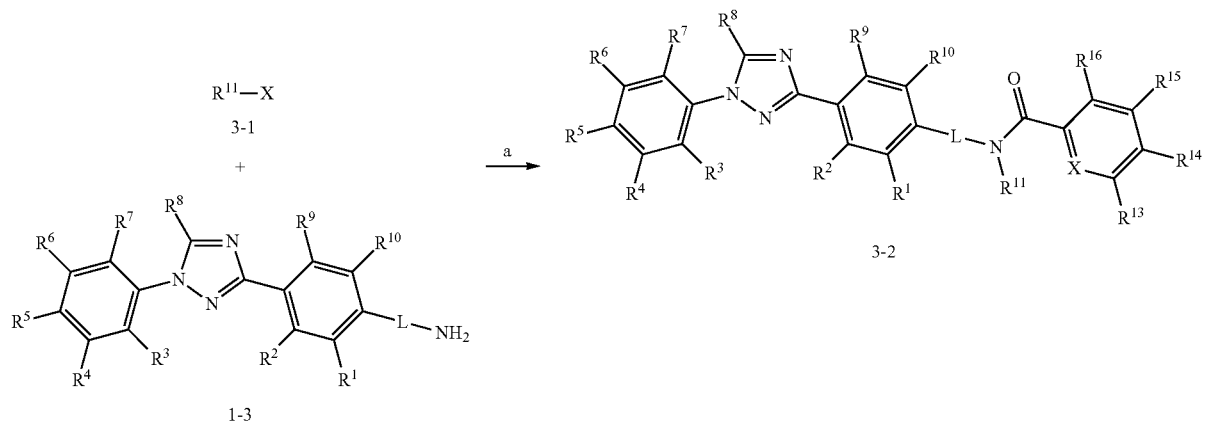

an alkyl halide, alkyl triflate, or alkyl sulfonate to form the alkylated amide (3-2); or followed by treatment with an acyl source such as acetyl chloride or acetic anhydride to form the acylated amide (3-2).

Preparation of Thioamides

The thioamide products (4-1, Scheme 4) of Formula One can be prepared from the corresponding amide (1-4). The amide can be treated directly with a source of sulfur, such as phosphorus pentasulfide or 2,4-bis(4-methoxyphenyl)-1,3,2,4-dithiadiphosphetane 2,4-disulfide (Lawesson's reagent), in an aprotic solvent chosen from tetrahydrofuran, dichloromethane, chloroform, toluene, or pyridine, at temperatures from about 60° C. to about 120° C. to form the thioamide (4-1).

Preparation of Triaryl Intermediates

Triaryl-aniline intermediates can be used to prepare molecules of Formula One. These triaryl intermediates can be prepared by methods previously described in the chemical literature, including Crouse, et al., WO2009102736 (the entire disclosure of which is hereby incorporated by reference).

Some of the procedures described above require use of triaryl-aniline intermediates, which are novel intermediates. These may be prepared as described in Scheme 5. An aryl halide (5-1) such as 4-trifluoromethylphenyl iodobenzene or 1-iodo-4-isopropoxybenzene, can be coupled to bromo-triazole (5-2, step a) in the presence of cesium carbonate or potassium phosphate, in a polar aprotic solvent such as dimethylformamide. This reaction is catalyzed by a copper salt such as copper(I) iodide and a chelator such as 8-hydroxyquinoline, both present in about 0.05 to about 0.25 equivalents, at a temperature ranging between about 80° C. and about 140° C., to form the corresponding triazole (5-3).

Coupling of the bromo-heterocycle (5-3) with a boronate ester (5-4, step b) can be accomplished using a palladium catalyst, such tetrakis(triphenylphosphine) palladium(0), in the presence of a base, such as sodium bicarbonate, in a suitable solvent system, such as dioxane/water, at temperatures from about 50° C. to about 120° C. to form the desired aniline (5-5).

Some of the procedures described below require use of triaryl bromide intermediates, which are novel intermediates. These may be prepared as described Scheme 4

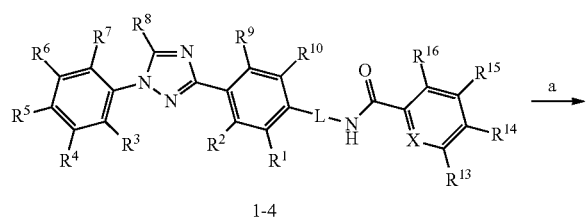

1-4

Scheme 5

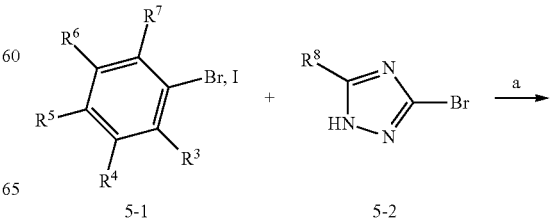

5-1  +  5-2

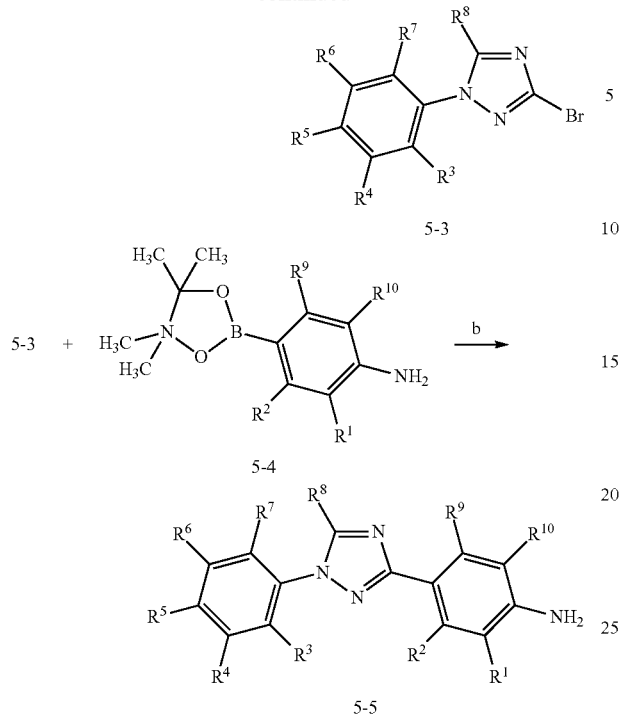

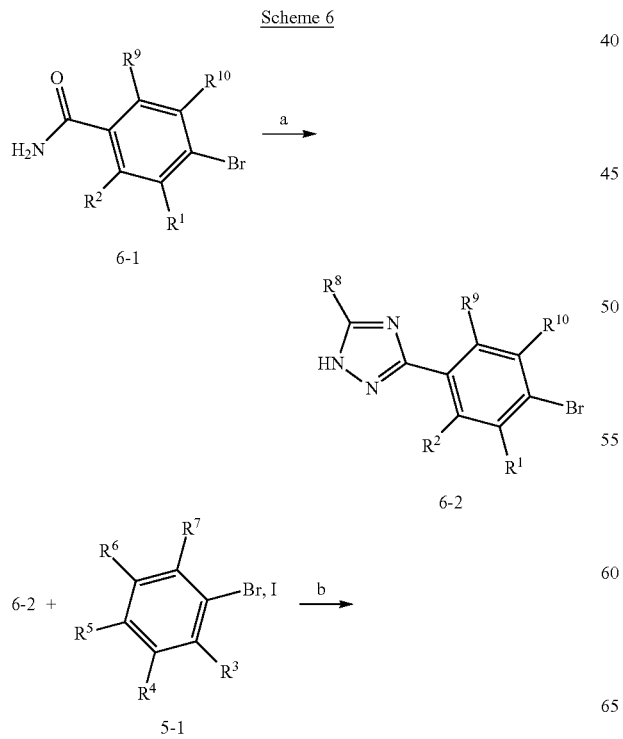

in Scheme 6. Bromotriazole (6-2, step a) may be prepared in two steps from 4-bromobenzamide (6-1) under conditions described previously (Crouse, et al., WO2009102736). This triazole can then be coupled to an aryl halide (5-1) such as 4-trifluoromethoxyphenyl bromobenzene, in the presence of cesium carbonate or

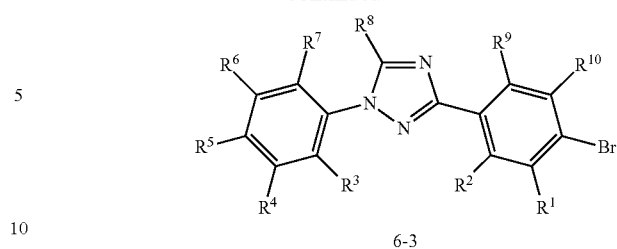

potassium phosphate, in a polar aprotic solvent such as dimethylformamide. This reaction is catalyzed by a copper salt such as copper(I) iodide and a chelator such as 8-hydroxyquinoline, both present in about 0.05 to about 0.25 equivalents, at a temperature ranging between about 80° C. and about 140° C., to form the triaryl bromide intermediate (6-3, step b).

Preparation of 1-Atom Linked Intermediates

Molecules of Formula One wherein L is $C_1$ alkyl, can be prepared as described in

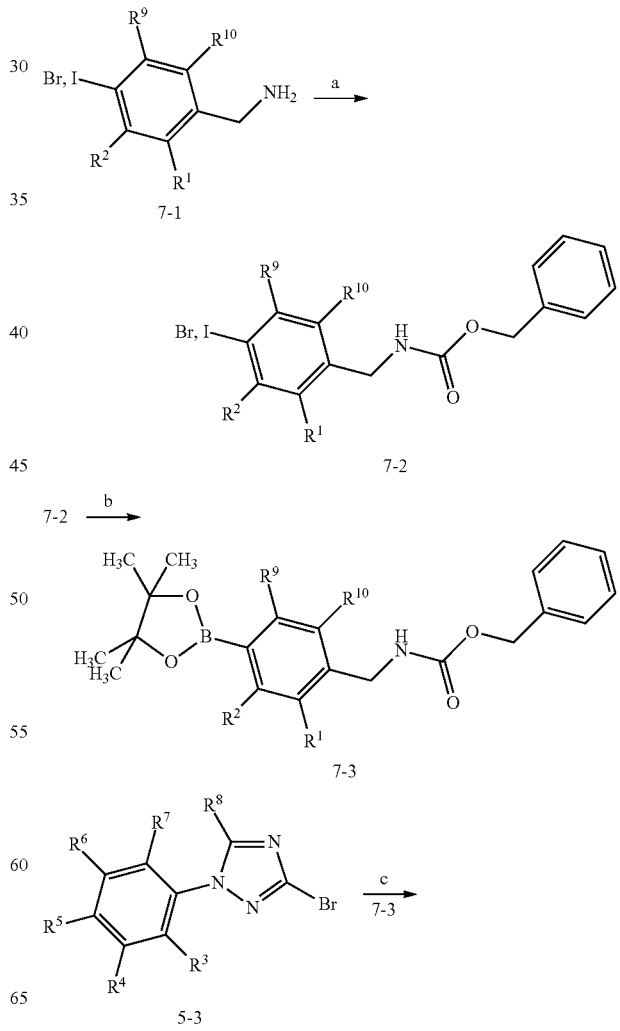

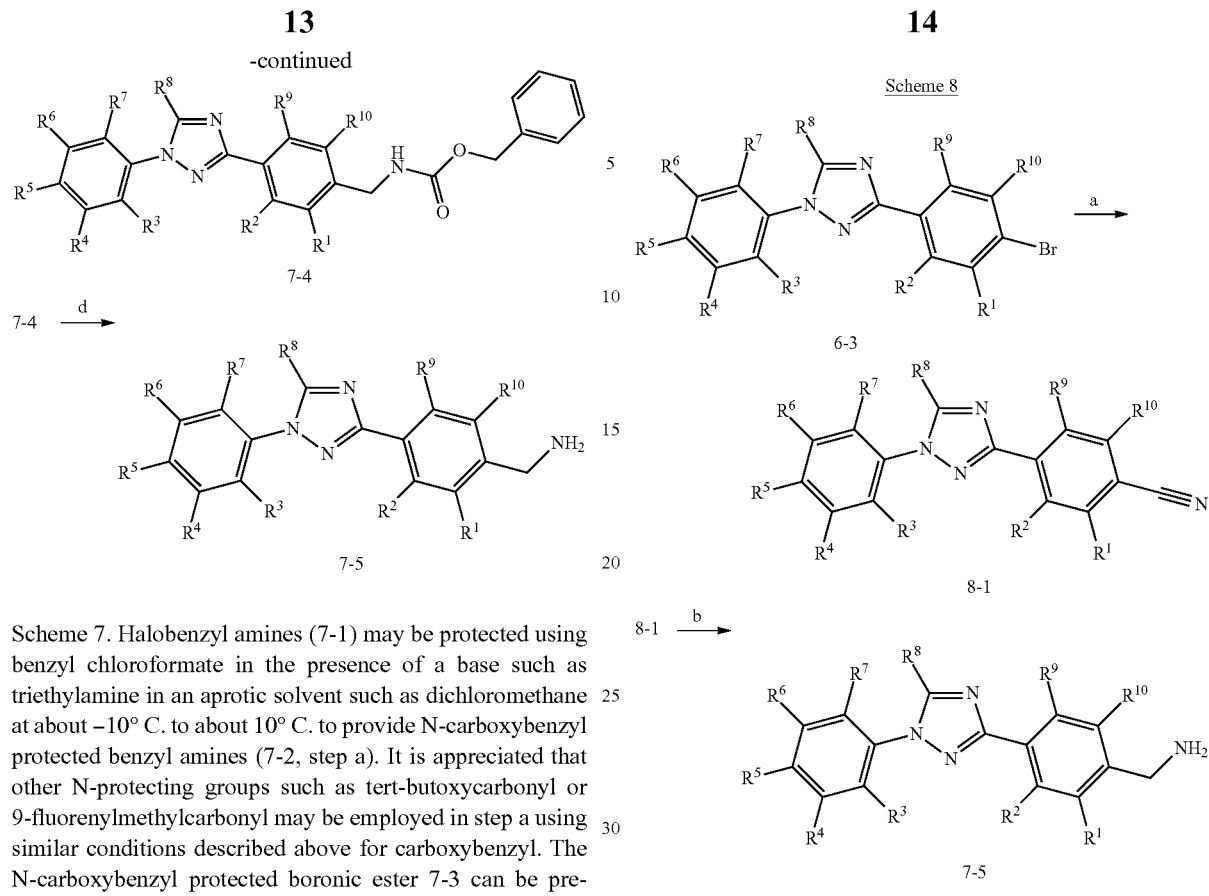

Scheme 7. Halobenzyl amines (7-1) may be protected using benzyl chloroformate in the presence of a base such as triethylamine in an aprotic solvent such as dichloromethane at about −10° C. to about 10° C. to provide N-carboxybenzyl protected benzyl amines (7-2, step a). It is appreciated that other N-protecting groups such as tert-butoxycarbonyl or 9-fluorenylmethylcarbonyl may be employed in step a using similar conditions described above for carboxybenzyl. The N-carboxybenzyl protected boronic ester 7-3 can be prepared using Miyaura conditions (step b). Coupling of the boronate esters with a bromo-heterocycle (5-3) can be accomplished using a palladium catalyst, such tetrakis(triphenylphosphine) palladium(0), in the presence of a base, such as sodium bicarbonate, potassium phosphate, or cesium fluoride, in a suitable solvent system, such as dioxane/water, at temperatures from about 50° C. to about 120° C. to form N-protected aminoalkylphenyl intermediates (7-4, step c). Deprotection of the carboxybenzyl group can be accomplished under acidic conditions with a strong acid such as hydrogen bromide, followed by free basing with a base such as sodium bicarbonate or sodium hydroxide, to furnish the free amines (7-5, step d). Alternatively, deprotection of the carboxybenzyl group may be accomplished by treatment with hydrogen in the presence of a transition metal catalyst, such as palladium on carbon. It is appreciated that similar methods could be applied to compounds wherein L is $C_1$-$C_4$ alkyl.

Alternatively, molecules of Formula One wherein L is $C_1$ alkyl, can be prepared as described in Scheme 8. Incorporation of the cyanide from a cyanide source such as zinc cyanide onto a bromo-heterocycle (5-3) can be accomplished using a palladium catalyst such as tetrakis(triphenylphosphine) palladium(0), in a suitable solvent system, such as dimethylformamide, at temperatures from about 50° C. to about 120° C. to form triaryl cyano intermediates (8-1, step a). Reduction of the cyano group can be accomplished by treatment with a metal reductant such as palladium on carbon in the presence of a strong acid such as hydrogen chloride, followed by free basing with a base such as sodium bicarbonate or sodium hydroxide, to furnish the free benzyl amines (7-5, step b).

Preparation of Ethyl Linked Intermediates

Preparation of compounds wherein L is $C_2$ alkyl is described in Schemes 9. Using conditions first described by Molander et al. *Org. Lett.,* 2007, 9 (2), pp 203-206, coupling of a triaryl bromide (6-3, step a), with potassium (2-((tert-butoxycarbonyl)amino)ethyl)trifluoroborate in the presence of a palladium catalyst such as palladium(II) acetate, and a base such as cesium carbonate, at temperatures from about 80° C. to about 120° C., may result in the formation of the corresponding 2-(tert-butoxycarbonyl)amino)ethyl derivative 9-1. Further treatment of this material with about 1 to about 5 equivalents of an acid such as trifluoroacetic acid, in an aprotic solvent such as dichloromethane or dioxane at temperatures from about 0° C. to about 50° C., may result in the cleavage of the tert-butoxycarbonyl group and formation of the corresponding acid salt of the amine (9-3, step b). It is appreciated that the obtained amine salts may be treated with a base, such as sodium bicarbonate or triethylamine to obtain the free amine.

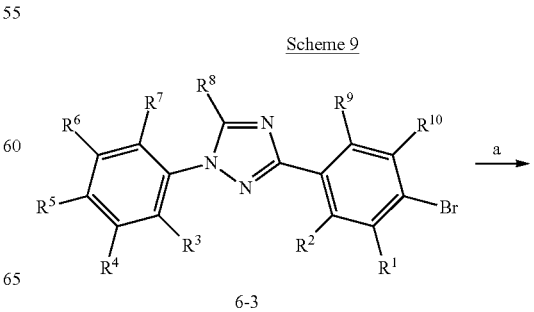

-continued

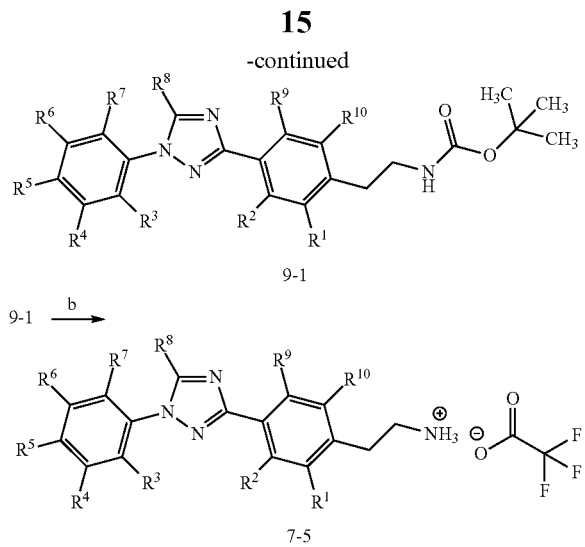

9-1

9-1 →b 7-5

EXAMPLES

These examples are for illustration purposes and are not to be construed as limiting the disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw or ACD Name Pro. If such programs are unable to name a molecule, the molecule is named using conventional naming rules. $^1$H NMR spectral data are in ppm (δ) and were recorded at 300, 400 or 600 MHz, and $^{13}$C NMR spectral data are in ppm (δ) and were recorded at 75, 100 or 150 MHz, unless otherwise stated.

Example 1

Preparation of 3-bromo-1-(4-isopropoxyphenyl)-1H-1,2,4-triazole

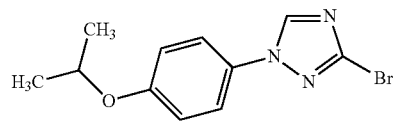 [SMILES: CC(C)Oc1ccc(-n2cnc(Br)n2)cc1]

3-bromo-1H-1,2,4-triazole (1.75 g, 11.8 mmol), copper(I) iodide (0.370 g, 1.94 mmol), cesium carbonate (4.98 g, 15.3 mmol), and 1-iodo-4-isopropoxybenzene (2.04 g, 7.78 mmol) (Katsumatu, T., et al. Macromolecular Chemistry and Physics, 2009, 210 (22), 1891-1902) was placed in dimethylsulfoxide (50 mL) and degassed with nitrogen for 10 minutes. The solution was heated at 100° C. for 20 hours. After cooling to room temperature, the reaction mixture was diluted with ethyl acetate and filtered through Celite®. The resulting filter cake was rinsed with additional ethyl acetate (100 mL). The filtrate was washed with water (2×50 mL). The combined aqueous washes were neutralized with hydrochloric acid (2 N) as measured by pH paper. The aqueous solution was extracted with ethyl acetate (2×30 mL) and the organic extracts were combined, and then dried over anhydrous magnesium sulfate. The organic solution was concentrated onto Celite® and purified by silica gel chromatography using 0-100% ethyl acetate/hexanes as eluent. The relevant fractions were concentrated to obtain the title compound as a yellow oil (0.540 g, 23%): $^1$H NMR (400 MHz, CDCl$_3$) δ 8.31 (s, 1H), 7.51 (d, J=9.1 Hz, 2H), 6.98 (d, J=9.0 Hz, 2H), 4.59 (p, J=6.1 Hz, 1H), 1.36 (d, J=6.1 Hz, 6H); ESIMS m/z 283 ([M+H]$^+$).

Example 2

Preparation of 4-(1-(4-isopropoxyphenyl)-1H-1,2,4-triazol-3-yl)aniline (C2)

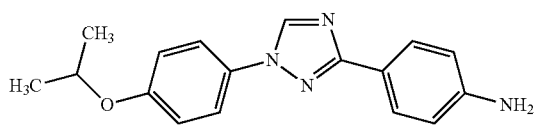 [SMILES: CC(C)Oc1ccc(-n2cnc(-c3ccc(N)cc3)n2)cc1]

Placed 3-bromo-1-(4-isopropoxyphenyl)-1H-1,2,4-triazole (C1) (0.540 g, 1.91 mmol), 4-(4,4,5,5-tetramethyl-1,3,2-dioxaborolan-2-yl)aniline (0.510 g, 2.32 mmol), tetrakis(triphenylphosphine) palladium(0) (0.240 g, 0.210 mmol), and potassium carbonate (2.65 g, 19.2 mmol) in 1,2-dimethoxyethane (8 mL) and water (2 mL) and degassed the mixture with nitrogen for 10 minutes. The solution was heated at 120° C. for 15 hours. The solution was cooled to room temperature and diluted the mixture with ethyl acetate (5 mL). The resultant salts were filtered and the layers were separated. The aqueous layers were extracted with ethyl acetate (2×5 mL). The combined organic layers were dried over anhydrous magnesium sulfate and concentrated onto Celite®. Purification by silica gel chromatography using 0-100% ethyl acetate/hexanes as eluent provided the title compound as a tan solid (0.430 g, 73%): $^1$H NMR (400 MHz, CDCl$_3$) δ 8.40 (s, 1H), 7.99 (d, J=8.7 Hz, 2H), 7.60 (d, J=9.1 Hz, 2H), 6.99 (d, J=9.0 Hz, 2H), 6.76 (d, J=8.7 Hz, 2H), 4.59 (p, J=6.1 Hz, 1H), 3.83 (s, 2H), 1.37 (d, J=6.1 Hz, 6H); ESIMS m/z 295 ([M+H]$^+$).

Example 3

Preparation of N-(4-(1-(4-isopropoxyphenyl)-1H-1,2,4-triazol-3-yl)phenyl)-2'-methoxy-[1,1'-biphenyl]-3-carboxamide (F5)

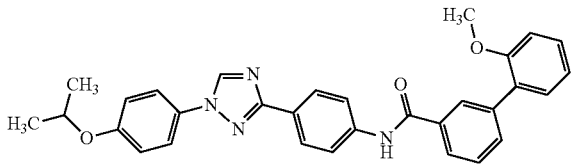 [SMILES: COc1ccccc1-c1cccc(C(=O)Nc2ccc(-c3ncn(-c4ccc(OC(C)C)cc4)n3)cc2)c1]

To a mixture of 2'-methoxy-[1,1'-biphenyl]-3-carboxylic acid (0.140 g, 0.610 mmol) in dichloromethane (5 mL) was added oxalyl chloride (0.150 mL, 1.75 mmol) and dimethylformamide (2 drops). After stirring for 3 hours at room temperature, the reaction was concentrated to dryness. The resulting yellow oil was dissolved in anhydrous tetrahydrofuran (2 mL) and added to a solution of 4-(1-(4-isopropoxyphenyl)-1H-1,2,4-triazol-3-yl)aniline (C2) (0.134 g, 0.460 mmol) dissolved in tetrahydrofuran (3 mL) and diisopropylethylamine (0.190 mL, 1.09 mmol) and stirred at room temperature for 18 hours. The solution was diluted with ethyl acetate (10 mL) and washed with saturated aqueous sodium bicarbonate. The aqueous wash was extracted with ethyl acetate (2×5 mL) and the combined organic layers were dried over anhydrous magnesium sulfate. The solution was concentrated onto Celite® and purified by silica gel chromatography using 0-100% ethyl acetate/(1:1 hexanes/dichloromethane) as eluent. The relevant fractions were concentrated to give the title compound as an off-white solid (0.151 g, 62%).

The following compounds were prepared according to the procedures disclosed in Example 3:

6-Fluoro-N-(4-(1-(4-isopropoxyphenyl)-1H-1,2,4-triazol-3-yl)phenyl)-[1,1'-biphenyl]-3-carboxamide (F16)

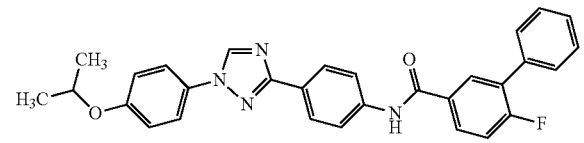 [SMILES: CC(C)Oc1ccc(-n2cnc(-c3ccc(NC(=O)c4ccc(F)c(-c5ccccc5)c4)cc3)n2)cc1]

Isolated as a white solid (0.118 g, 52%).

6-Fluoro-N-(4-(1-(4-isopropoxyphenyl)-1H-1,2,4-triazol-3-yl)phenyl)-2'-methoxy-[1,1'-biphenyl]-3-carboxamide (F4)

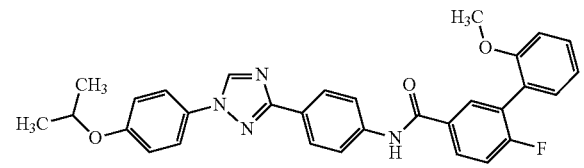 [SMILES: COc1ccccc1-c1cc(C(=O)Nc2ccc(-c3ncn(-c4ccc(OC(C)C)cc4)n3)cc2)ccc1F]

Isolated as a white solid (0.106 g, 42%).

Example 4

Preparation of N-(4-(1-(4-(trifluoromethoxy)phenyl)-1H-1,2,4-triazol-3-yl)phenyl)-[1,1'-biphenyl]-3-carboxamide (F24)

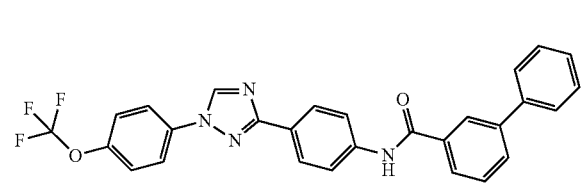 [SMILES: O=C(Nc1ccc(-c2ncn(-c3ccc(OC(F)(F)F)cc3)n2)cc1)c1cccc(-c2ccccc2)c1]

To a mixture of [1,1'-biphenyl]-3-carboxylic acid (0.172 g, 0.870 mmol) in dichloromethane (4 mL) was added oxalyl chloride (0.150 mL, 1.75 mmol) and dimethylformamide (2 drops). After stirring for 3 hours at room temperature, the reaction was concentrated to dryness. The resulting yellow oil was dissolved in anhydrous tetrahydrofuran (1 mL) and added to a solution of 4-(1-(4-(trifluoromethoxy)phenyl)-1H-1,2,4-triazol-3-yl)aniline (0.102 g, 0.320 mmol) (WO 2009102736) dissolved in tetrahydrofuran (3 mL) and diisopropylethylamine (0.150 mL, 0.860 mmol) and stirred at room temperature for 18 hours. The solution was diluted with ethyl acetate (10 mL) and washed with saturated aqueous sodium bicarbonate. The aqueous wash was extracted with ethyl acetate (2×5 mL) and the combined organic layers were dried over anhydrous magnesium sulfate. The solution was concentrated onto Celite® and purified by flash column chromatography using 0-100% ethyl acetate/(1:1 hexanes/dichloromethane) as eluent. The relevant fractions were concentrated to give the title compound as a white solid (0.0440 g, 28%).

The following compounds were prepared according to the procedures disclosed in Example 4:

5-Fluoro-N-(4-(1-(4-(trifluoromethoxy)phenyl)-1H-1,2,4-triazol-3-yl)phenyl)-[1,1'-biphenyl]-3-carboxamide (F25)

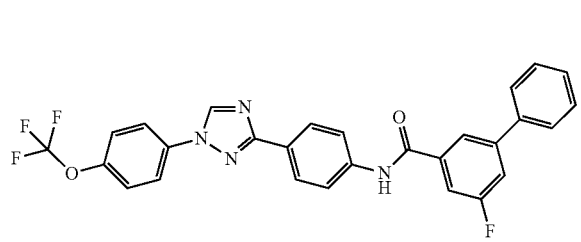 [SMILES: O=C(Nc1ccc(-c2ncn(-c3ccc(OC(F)(F)F)cc3)n2)cc1)c1cc(F)cc(-c2ccccc2)c1]

Isolated as an off-white solid (0.062 g, 27%).

5-Fluoro-2'-methyl-N-(4-(1-(4-(trifluoromethoxy)phenyl)-1H-1,2,4-triazol-3-yl)phenyl)-[1,1'-biphenyl]-3-carboxamide (F39)

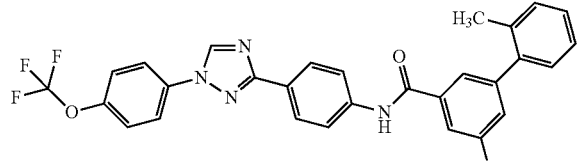

Isolated as an orange oily solid (0.136 g, 57%).

5-Chloro-N-(4-(1-(4-(trifluoromethoxy)phenyl)-1H-1,2,4-triazol-3-yl)phenyl)-[1,1'-biphenyl]-3-carboxamide (F43)

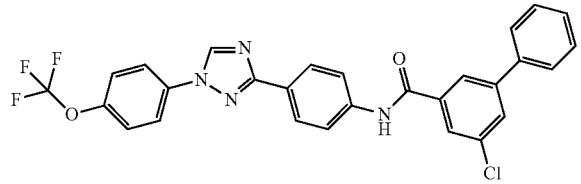 [SMILES: O=C(Nc1ccc(-c2ncn(-c3ccc(OC(F)(F)F)cc3)n2)cc1)c1cc(Cl)cc(-c2ccccc2)c1]

Isolated as an off-white solid (0.148 g, 65%).

2'-Chloro-N-(4-(1-(4-(trifluoromethoxy)phenyl)-1H-1,2,4-triazol-3-yl)phenyl)-[1,1'-biphenyl]-3-carboxamide (F30)

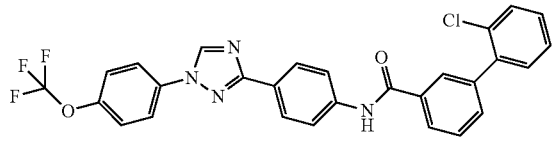 [SMILES: O=C(Nc1ccc(-c2ncn(-c3ccc(OC(F)(F)F)cc3)n2)cc1)c1cccc(-c2ccccc2Cl)c1]

Isolated as an off-white solid (0.061 g, 25%).

4-Chloro-N-(4-(1-(4-(trifluoromethoxy)phenyl)-1H-1,2,4-triazol-3-yl)phenyl)-[1,1'-biphenyl]-3-carboxamide (F15)

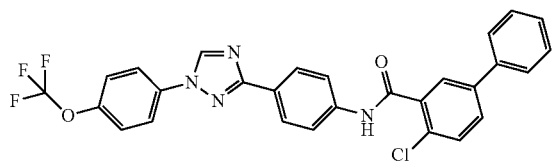 [SMILES: O=C(Nc1ccc(-c2ncn(-c3ccc(OC(F)(F)F)cc3)n2)cc1)c1cc(-c2ccccc2)ccc1Cl]

Isolated as an off-white solid (0.066 g, 29%).

2'-Methyl-N-(4-(1-(4-(trifluoromethoxy)phenyl)-1H-1,2,4-triazol-3-yl)phenyl)-[1,1'-biphenyl]-3-carboxamide (F17)

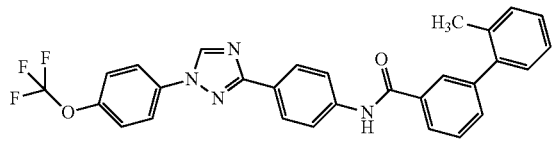 [SMILES: Cc1ccccc1-c1cccc(C(=O)Nc2ccc(-c3ncn(-c4ccc(OC(F)(F)F)cc4)n3)cc2)c1]

Isolated as an off-white solid (0.130 g, 53%).

2'-Methoxy-N-(4-(1-(4-(trifluoromethoxy)phenyl)-1H-1,2,4-triazol-3-yl)phenyl)-[1,1'-biphenyl]-3-carboxamide (F22)

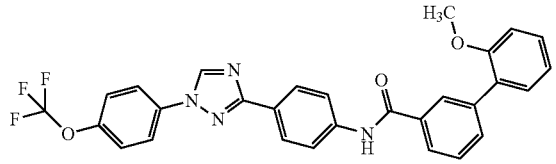 [SMILES: COc1ccccc1-c1cccc(C(=O)Nc2ccc(-c3ncn(-c4ccc(OC(F)(F)F)cc4)n3)cc2)c1]

Isolated as an off-white solid (0.142 g, 73%).

2',6'-Dimethyl-N-(4-(1-(4-(trifluoromethoxy)phenyl)-1H-1,2,4-triazol-3-yl)phenyl)-[1,1'-biphenyl]-3-carboxamide (F12)

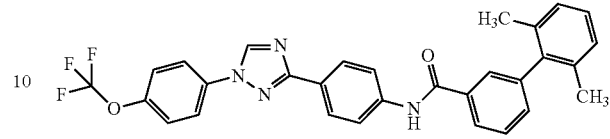

Isolated as an off-white solid (0.206 g, 54%).

6-Fluoro-N-(4-(1-(4-(trifluoromethoxy)phenyl)-1H-1,2,4-triazol-3-yl)phenyl)-[1,1'-biphenyl]-3-carboxamide (F11)

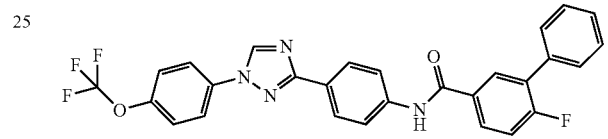

Isolated as an off-white solid (0.052 g, 25%).

4'-Methoxy-2'-methyl-N-(4-(1-(4-(trifluoromethoxy)phenyl)-1H-1,2,4-triazol-3-yl)phenyl)-[1,1'-biphenyl]-3-carboxamide (F49)

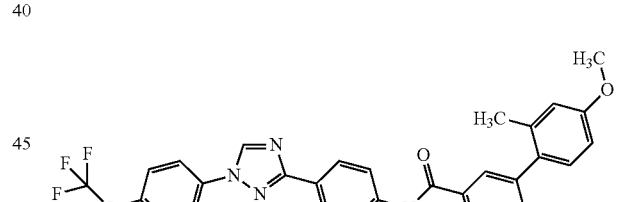

Isolated as an off-white solid (0.120 g, 52%).

6-Phenyl-N-(4-(1-(4-(trifluoromethoxy)phenyl)-1H-1,2,4-triazol-3-yl)phenyl)picolinamide (F27)

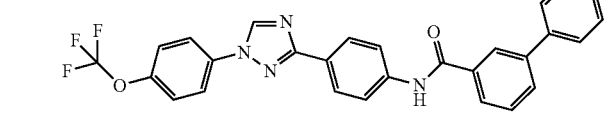

Isolated as an off-white solid (0.078 g, 35%).

4-Fluoro-N-(4-(1-(4-(trifluoromethoxy)phenyl)-1H-1,2,4-triazol-3-yl)phenyl)-[1,1'-biphenyl]-3-carboxamide (F48)

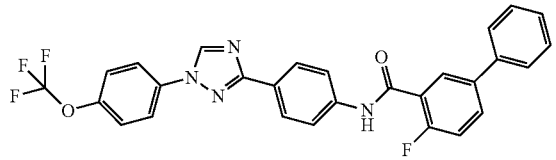

Isolated as a white solid (0.107 g, 49%).

6-Chloro-2'-methyl-N-(4-(1-(4-(trifluoromethoxy)phenyl)-1H-1,2,4-triazol-3-yl)phenyl)-[1,1'-biphenyl]-3-carboxamide (F32)

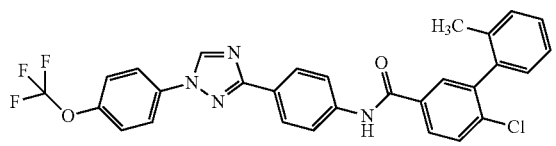 [SMILES: Cc1ccccc1-c1cc(C(=O)Nc2ccc(-c3ncn(-c4ccc(OC(F)(F)F)cc4)n3)cc2)ccc1Cl]

Isolated as a white solid (0.149 g, 66%).

6-(2,4-Dichlorophenyl)-N-(4-(1-(4-(trifluoromethoxy)phenyl)-1H-1,2,4-triazol-3-yl)phenyl)picolinamide (F18)

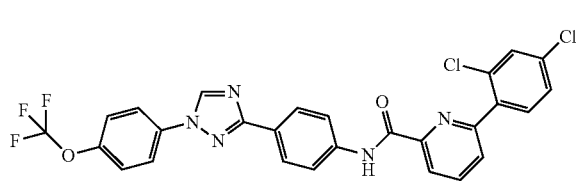 [SMILES: O=C(Nc1ccc(-c2ncn(-c3ccc(OC(F)(F)F)cc3)n2)cc1)c1cccc(-c2ccc(Cl)cc2Cl)n1]

Isolated as an off-white solid (0.041 g, 16%).

6-(2,4-Dimethylphenyl)-N-(4-(1-(4-(trifluoromethoxy)phenyl)-1H-1,2,4-triazol-3-yl)phenyl)picolinamide (F2)

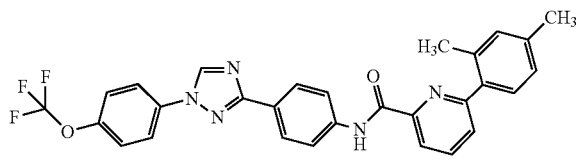 [SMILES: Cc1ccc(-c2cccc(C(=O)Nc3ccc(-c4ncn(-c5ccc(OC(F)(F)F)cc5)n4)cc3)n2)c(C)c1]

Isolated as a tan solid (0.107 g, 45%).

6-(o-Tolyl)-N-(4-(1-(4-(trifluoromethoxy)phenyl)-1H-1,2,4-triazol-3-yl)phenyl)picolinamide (F33)

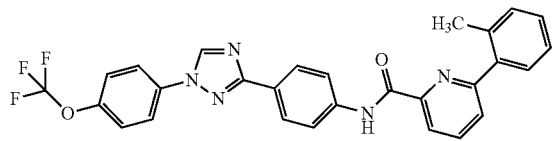 [SMILES: Cc1ccccc1-c1cccc(C(=O)Nc2ccc(-c3ncn(-c4ccc(OC(F)(F)F)cc4)n3)cc2)n1]

Isolated as a white solid (0.161 g, 68%).

6-Methoxy-N-(4-(1-(4-(trifluoromethoxy)phenyl)-1H-1,2,4-triazol-3-yl)phenyl)-[1,1'-biphenyl]-3-carboxamide (F37)

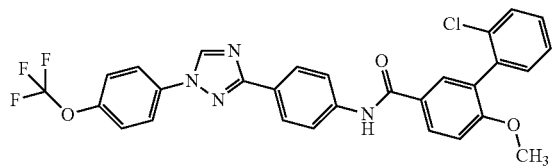 [SMILES: COc1ccc(C(=O)Nc2ccc(-c3ncn(-c4ccc(OC(F)(F)F)cc4)n3)cc2)cc1-c1ccccc1Cl]

Isolated as a white solid (0.206 g, 70%).

2'-(Trifluoromethoxy)-N-(4-(1-(4-(trifluoromethoxy)phenyl)-1H-1,2,4-triazol-3-yl)phenyl)-[1,1'-biphenyl]-3-carboxamide (F1)

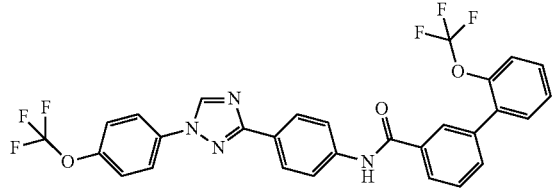 [SMILES: O=C(Nc1ccc(-c2ncn(-c3ccc(OC(F)(F)F)cc3)n2)cc1)c1cccc(-c2ccccc2OC(F)(F)F)c1]

Isolated as an off-white solid (0.087 g, 34%).

2'-Acetyl-N-(4-(1-(4-(trifluoromethoxy)phenyl)-1H-1,2,4-triazol-3-yl)phenyl)-[1,1'-biphenyl]-3-carboxamide (F41)

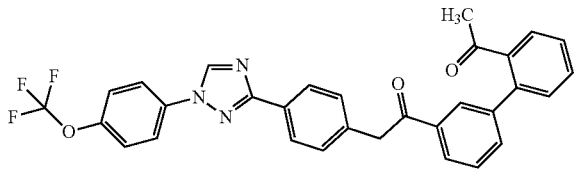 [SMILES: CC(=O)c1ccccc1-c1cccc(C(=O)Cc2ccc(-c3ncn(-c4ccc(OC(F)(F)F)cc4)n3)cc2)c1]

Isolated as an off-white solid (0.074 g, 30%).

6-Fluoro-2'-methoxy-N-(4-(1-(4-(trifluoromethoxy) phenyl)-1H-1,2,4-triazol-3-yl)phenyl)-[1,1'-biphenyl]-3-carboxamide (F44)

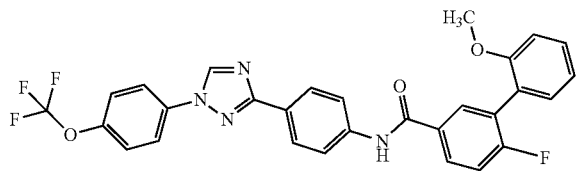 [SMILES: COc1ccccc1-c1cc(C(=O)Nc2ccc(-c3ncn(-c4ccc(OC(F)(F)F)cc4)n3)cc2)ccc1F]

Isolated as a white solid (0.160 g, 46%).

2',6-Difluoro-N-(4-(1-(4-(trifluoromethoxy)phenyl)-1H-1,2,4-triazol-3-yl)phenyl)-[1,1'-biphenyl]-3-carboxamide (F28)

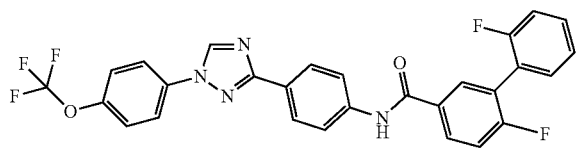 [SMILES: O=C(Nc1ccc(-c2ncn(-c3ccc(OC(F)(F)F)cc3)n2)cc1)c1ccc(F)c(-c2ccccc2F)c1]

Isolated as an off-white solid (0.121 g, 49%).

2'-(Benzyloxy)-N-(4-(1-(4-(trifluoromethoxy)phenyl)-1H-1,2,4-triazol-3-yl)phenyl)-[1,1'-biphenyl]-3-carboxamide (F3)

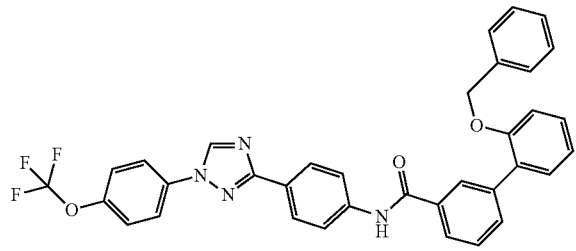 [SMILES: O=C(Nc1ccc(-c2ncn(-c3ccc(OC(F)(F)F)cc3)n2)cc1)c1cccc(-c2ccccc2OCc2ccccc2)c1]

Isolated as a white solid (0.101 g, 35%).

2'-Ethyl-N-(4-(1-(4-(trifluoromethoxy)phenyl)-1H-1,2,4-triazol-3-yl)phenyl)-[1,1'-biphenyl]-3-carboxamide (F8)

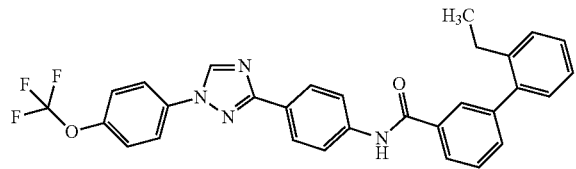 [SMILES: CCc1ccccc1-c1cccc(C(=O)Nc2ccc(-c3ncn(-c4ccc(OC(F)(F)F)cc4)n3)cc2)c1]

Isolated as a white solid (0.089 g, 30%).

2'-Ethoxy-N-(4-(1-(4-(trifluoromethoxy)phenyl)-1H-1,2,4-triazol-3-yl)phenyl)-[1,1'-biphenyl]-3-carboxamide (F38)

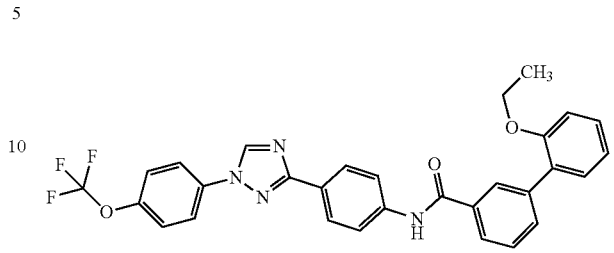

Isolated as a white solid (0.209 g, 73%).

2'-(Dimethylamino)-N-(4-(1-(4-(trifluoromethoxy) phenyl)-1H-1,2,4-triazol-3-yl)phenyl)-[1,1'-biphenyl]-3-carboxamide (F10)

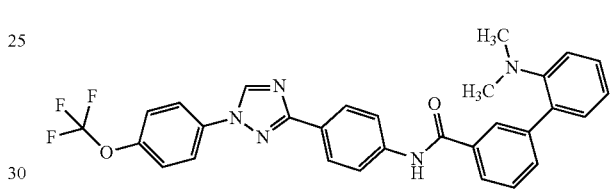

Isolated as a yellow oil (0.084 g, 29%).

6-Chloro-N-(4-(1-(4-(trifluoromethoxy)phenyl)-1H-1,2,4-triazol-3-yl)phenyl)-[1,1'-biphenyl]-3-carboxamide (F34)

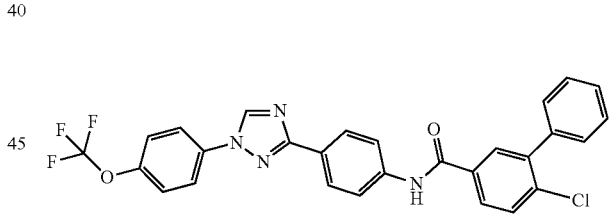

Isolated as a tan solid (0.141 g, 59%).

2-Methyl-N-(4-(1-(4-(trifluoromethoxy)phenyl)-1H-1,2,4-triazol-3-yl)phenyl)-[1,1'-biphenyl]-3-carboxamide (F14)

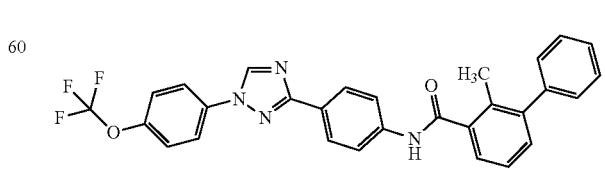

Isolated as an off-white solid (0.090 g, 40%).

Example 5

Preparation of 2'-methoxy-N-methyl-N-(4-(1-(4-(trifluoromethoxy)phenyl)-1H-1,2,4-triazol-3-yl)phenyl)-[1,1'-biphenyl]-3-carboxamide (F19)

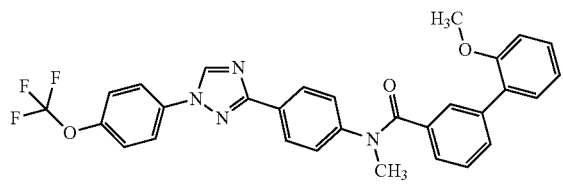 [SMILES: COc1ccccc1-c1cccc(C(=O)N(C)c2ccc(-c3ncn(-c4ccc(OC(F)(F)F)cc4)n3)cc2)c1]

To a solution of 2'-methoxy-N-(4-(1-(4-(trifluoromethoxy)phenyl)-1H-1,2,4-triazol-3-yl)phenyl)-[1,1'-biphenyl]-3-carboxamide (F22) (0.080 g, 0.15 mmol) dissolved in tetrahydrofuran (2 mL) was added sodium hydride (60% by weight, 0.0096 g, 0.24 mmol). After stirring at room temperature for 20 minutes, methyl iodide (0.025 mL, 0.40 mmol) was added and the mixture stirred for 18 hours. Saturated aqueous sodium bicarbonate was added to the solution followed by extraction with ethyl acetate (3×5 mL). The combined organic extracts were dried over anhydrous magnesium sulfate and concentrated. Purification by flash column chromatography using 0-40% ethyl acetate/1:1 hexanes/dichloromethane as eluent provided the title compound as a colorless oil (0.039 g, 45%).

The following example was prepared according to the procedures disclosed in Example 5:

N-Ethyl-6-fluoro-2'-methoxy-N-(4-(1-(4-(trifluoromethoxy)phenyl)-1H-1,2,4-triazol-3-yl)phenyl)-[1,1'-biphenyl]-3-carboxamide (F64)

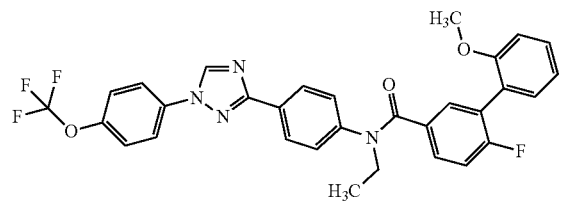 [SMILES: CCN(C(=O)c1ccc(F)c(-c2ccccc2OC)c1)c1ccc(-c2ncn(-c3ccc(OC(F)(F)F)cc3)n2)cc1]

Isolated as a colorless oil (0.163 g, 86%).

6-Fluoro-2'-methoxy-N-propyl-N-(4-(1-(4-(trifluoromethoxy)phenyl)-1H-1,2,4-triazol-3-yl)phenyl)-[1,1'-biphenyl]-3-carboxamide (F65)

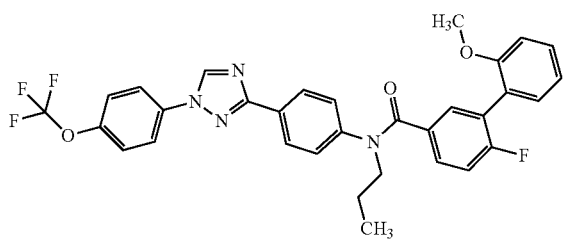 [SMILES: CCCN(C(=O)c1ccc(F)c(-c2ccccc2OC)c1)c1ccc(-c2ncn(-c3ccc(OC(F)(F)F)cc3)n2)cc1]

Isolated as a colorless oil (0.160 g, 89%).

N-(cyclopropylmethyl)-6-fluoro-2'-methoxy-N-(4-(1-(4-(trifluoromethoxy)phenyl)-1H-1,2,4-triazol-3-yl)phenyl)-[1,1'-biphenyl]-3-carboxamide (F66)

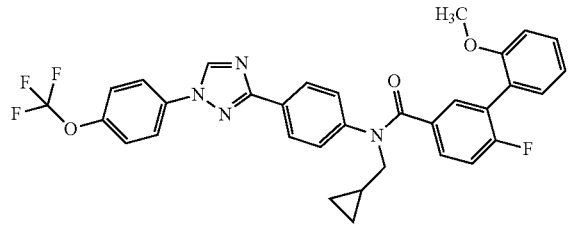 [SMILES: COc1ccccc1-c1cc(C(=O)N(CC2CC2)c2ccc(-c3ncn(-c4ccc(OC(F)(F)F)cc4)n3)cc2)ccc1F]

Isolated as a colorless oil (0.040 g, 22%).

N-acetyl-6-fluoro-2'-methoxy-N-(4-(1-(4-(trifluoromethoxy)phenyl)-1H-1,2,4-triazol-3-yl)phenyl)-[1,1'-biphenyl]-3-carboxamide (F67)

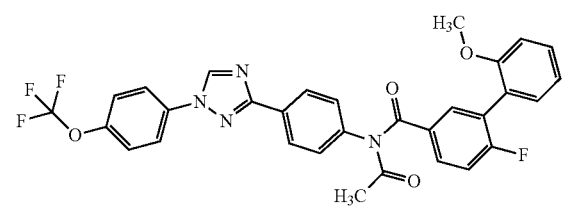 [SMILES: COc1ccccc1-c1cc(C(=O)N(C(C)=O)c2ccc(-c3ncn(-c4ccc(OC(F)(F)F)cc4)n3)cc2)ccc1F]

Acetic anhydride used as electrophile. Isolated as a colorless oil (0.214 g, 83%).

Example 6

Preparation of 2',6'-dimethyl-N-(4-(1-(4-(trifluoromethoxy)phenyl)-1H-1,2,4-triazol-3-yl)phenyl)-[1,1'-biphenyl]-3-carbothioamide (F46)

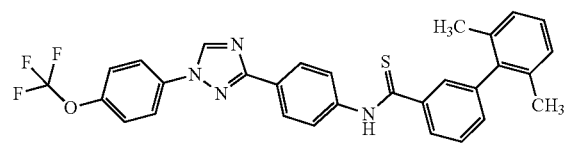 [SMILES: Cc1cccc(C)c1-c1cccc(C(=S)Nc2ccc(-c3ncn(-c4ccc(OC(F)(F)F)cc4)n3)cc2)c1]

To a solution of 2',6'-dimethyl-N-(4-(1-(4-(trifluoromethoxy)phenyl)-1H-1,2,4-triazol-3-yl)phenyl)-[1,1'-biphenyl]-3-carboxamide (F12) (0.132 g, 0.250 mmol) dissolved in tetrahydrofuran (3 mL) was added 2,4-bis(4-methoxyphenyl)-1,3,2,4-dithiadiphosphetane 2,4-disulfide (Lawesson's reagent) (0.129 g, 0.320 mmol) and the mixture was heated at 60° C. for 18 hours. Additional 2,4-bis(4-methoxyphenyl)-1,3,2,4-dithiadiphosphetane 2,4-disulfide (0.262 g, 0.65 mmol) was added and the reaction was allowed to heat at 60° C. until the reaction was determined to be complete. The reaction mixture was concentrated onto Celite® and purified by flash column chromatography using 0-100% ethyl acetate/(1:1 hexanes/dichloromethane). The title compound was obtained as a yellow oil (0.043 g, 30%).

The following example was prepared according to the procedures disclosed in Example 6:

2'-Methoxy-N-(4-(1-(4-(trifluoromethoxy)phenyl)-1H-1,2,4-triazol-3-yl)phenyl)-[1,1'-biphenyl]-3-carbothioamide (F21)

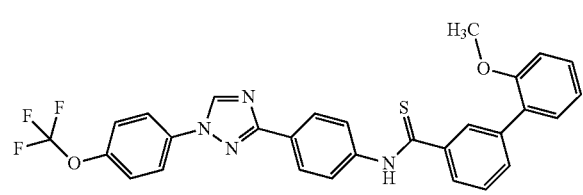 [SMILES: COc1ccccc1-c1cccc(C(=S)Nc2ccc(-c3ncn(-c4ccc(OC(F)(F)F)cc4)n3)cc2)c1]

Isolated as a yellow solid (0.087 g, 48%).

Example 7

Preparation of N-(4-(1-(4-(perfluoroethoxy)phenyl)-1H-1,2,4-triazol-3-yl)phenyl)-[1,1'-biphenyl]-3-carboxamide (F45)

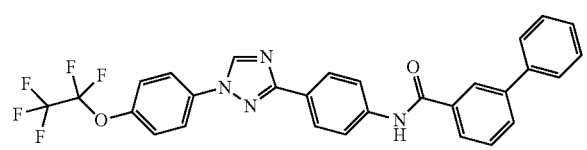

To a mixture of [1,1'-biphenyl]-3-carboxylic acid (0.172 g, 0.870 mmol) in dichloromethane (4 mL) was added oxalyl chloride (0.150 mL, 1.75 mmol) and dimethylformamide (2 drops). After stirring for 3 hours at room temperature, the reaction was concentrated to dryness. The resulting yellow oil was dissolved in anhydrous tetrahydrofuran (1 mL) and added to a solution of 4-(1-(4-(perfluoroethoxy)phenyl)-1H-1,2,4-triazol-3-yl)aniline (0.102 g, 0.280 mmol) (WO 2009102736) dissolved in tetrahydrofuran (3 mL) and diisopropylethylamine (0.150 mL, 0.860 mmol) and stirred at room temperature for 18 hours. The reaction was diluted with ethyl acetate (10 mL) and washed with saturated aqueous sodium bicarbonate. The aqueous wash was extracted with ethyl acetate (2×5 mL) and the combined organic layers were dried over anhydrous magnesium sulfate. The solution was concentrated onto Celite® and purified by flash column chromatography using 0-100% ethyl acetate/(1:1 hexanes/dichloromethane) as eluent. The relevant fractions were concentrated to give the title compound as an white solid (0.109 g, 68%).

The following examples were prepared according to the procedures disclosed in Example 7:

2'-Methyl-N-(4-(1-(4-(perfluoroethoxy)phenyl)-1H-1,2,4-triazol-3-yl)phenyl)-[1,1'-biphenyl]-3-carboxamide (F35)

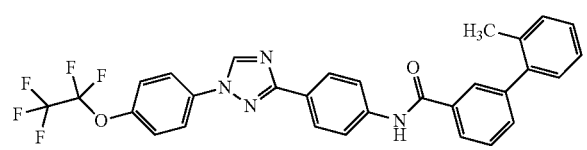 [SMILES: Cc1ccccc1-c1cccc(C(=O)Nc2ccc(-c3ncn(-c4ccc(OC(F)(F)C(F)(F)F)cc4)n3)cc2)c1]

Isolated as a white solid (0.095 g, 56%).

N-(4-(1-(4-(Perfluoroethoxy)phenyl)-1H-1,2,4-triazol-3-yl)phenyl)-6-phenylpicolinamide (F47)

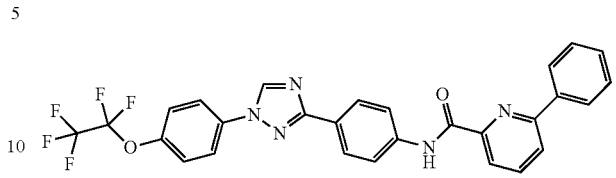

Isolated as a white solid (0.102 g, 67%).

6-Methoxy-N-(4-(1-(4-(perfluoroethoxy)phenyl)-1H-1,2,4-triazol-3-yl)phenyl)-[1,1'-biphenyl]-3-carboxamide (F13)

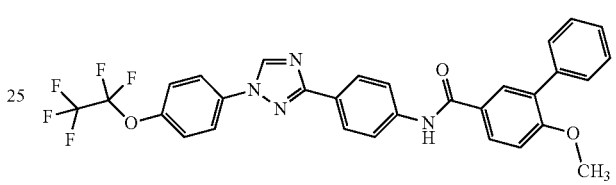

Isolated as a white solid (0.094 g, 42%).

2'-Methoxy-N-(4-(1-(4-(perfluoroethoxy)phenyl)-1H-1,2,4-triazol-3-yl)phenyl)-[1,1'-biphenyl]-3-carboxamide (F26)

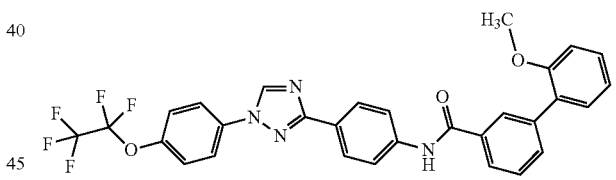

Isolated as a white solid (0.284 g, 67%).

N-(4-(1-(4-(Perfluoroethoxy)phenyl)-1H-1,2,4-triazol-3-yl)phenyl)-2'-(trifluoromethoxy)-[1,1'-biphenyl]-3-carboxamide (F36)

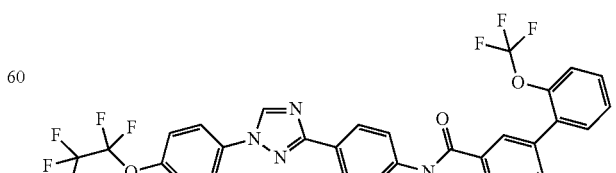

Isolated as an off-white solid (0.057 g, 22%).

2'-Acetyl-N-(4-(1-(4-(perfluoroethoxy)phenyl)-1H-1,2,4-triazol-3-yl)phenyl)-[1,1'-biphenyl]-3-carboxamide (F9)

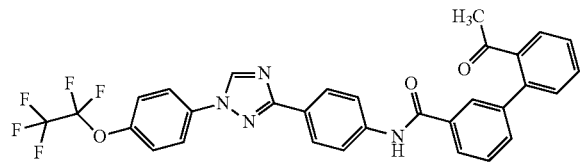 [SMILES: CC(=O)c1ccccc1-c1cccc(C(=O)Nc2ccc(-c3ncn(-c4ccc(OC(F)(F)C(F)(F)F)cc4)n3)cc2)c1]

Isolated as an off-white solid (0.110 g, 52%).

6-Fluoro-N-(4-(1-(4-(perfluoroethoxy)phenyl)-1H-1,2,4-triazol-3-yl)phenyl)-[1,1'-biphenyl]-3-carboxamide (F40)

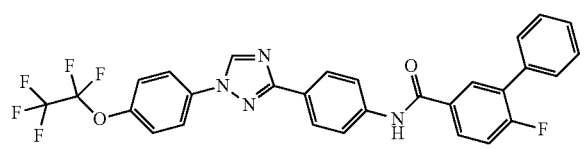 [SMILES: O=C(Nc1ccc(-c2ncn(-c3ccc(OC(F)(F)C(F)(F)F)cc3)n2)cc1)c1ccc(F)c(-c2ccccc2)c1]

Isolated as an off-white solid (0.138 g, 63%).

5-Chloro-N-(4-(1-(4-(perfluoroethoxy)phenyl)-1H-1,2,4-triazol-3-yl)phenyl)-[1,1'-biphenyl]-3-carboxamide (F6)

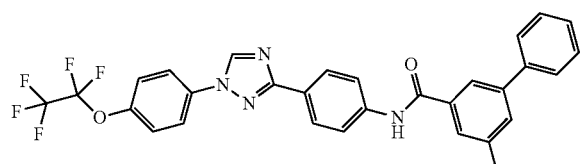

Isolated as an off-white solid (0.141 g, 63%).

5-Fluoro-2'-methyl-N-(4-(1-(4-(perfluoroethoxy)phenyl)-1H-1,2,4-triazol-3-yl)phenyl)-[1,1'-biphenyl]-3-carboxamide (F42)

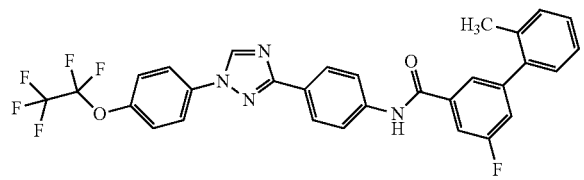 [SMILES: Cc1ccccc1-c1cc(F)cc(C(=O)Nc2ccc(-c3ncn(-c4ccc(OC(F)(F)C(F)(F)F)cc4)n3)cc2)c1]

Isolated as an off-white solid (0.160 g, 70%).

2',6'-Dimethyl-N-(4-(1-(4-(perfluoroethoxy)phenyl)-1H-1,2,4-triazol-3-yl)phenyl)-[1,1'-biphenyl]-3-carboxamide (F31)

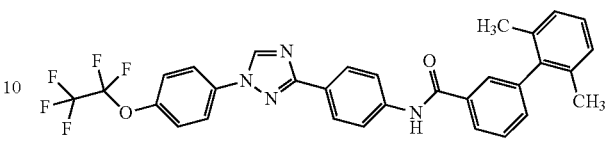

Isolated as an off-white solid (0.140 g, 63%).

6-Fluoro-2'-methoxy-N-(4-(1-(4-(perfluoroethoxy)phenyl)-1H-1,2,4-triazol-3-yl)phenyl)-[1,1'-biphenyl]-3-carboxamide (F7)

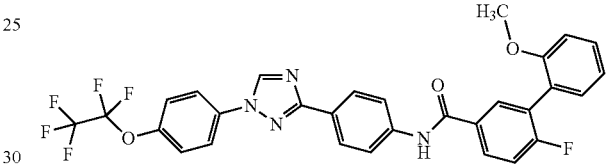

Isolated as an off-white solid (0.128 g, 62%).

Example 8

Preparation of 5-fluoro-N,2'-dimethyl-N-(4-(1-(4-(perfluoroethoxy)phenyl)-1H-1,2,4-triazol-3-yl)phenyl)-[1,1'-biphenyl]-3-carboxamide (F29)

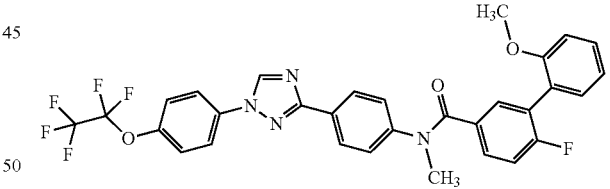

To a solution of 5-fluoro-2'-methyl-N-(4-(1-(4-(perfluoroethoxy)phenyl)-1H-1,2,4-triazol-3-yl)phenyl)-[1,1'-biphenyl]-3-carboxamide (F42) (0.070 g, 0.12 mmol) dissolved in tetrahydrofuran (2 mL) was added sodium hydride (60% by weight, 0.0096 g, 0.24 mmol). After stirring at room temperature for 20 minutes, methyl iodide (0.025 mL, 0.40 mmol) was added and the mixture was stirred for 2.5 hours. Saturated aqueous sodium bicarbonate was added to the solution followed by extraction with ethyl acetate (3×5 mL). The combined organic extracts were dried over anhydrous magnesium sulfate and concentrated. Purification by flash column chromatography using 0-40% ethyl acetate/ (1:1 hexanes/dichloromethane) as eluent provided the title compound as a colorless oil (0.044 g, 58%).

Example 9

Preparation of 2'-methoxy-N-(4-(1-(4-(perfluoroethoxy)phenyl)-1H-1,2,4-triazol-3-yl)phenyl)-[1,1'-biphenyl]-3-carbothioamide (F23)

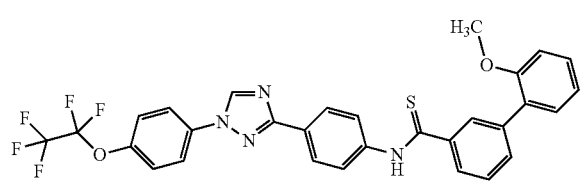 [SMILES: COc1ccccc1-c1cccc(C(=S)Nc2ccc(-c3ncn(-c4ccc(OC(F)(F)C(F)(F)F)cc4)n3)cc2)c1]

To a solution of 2'-methoxy-N-(4-(1-(4-(perfluoroethoxy)phenyl)-1H-1,2,4-triazol-3-yl)phenyl)-[1,1'-biphenyl]-3-carboxamide (F26) (0.132 g, 0.230 mmol) dissolved in tetrahydrofuran (2 mL) was added 2,4-bis(4-methoxyphenyl)-1,3,2,4-dithiadiphosphetane 2,4-disulfide (0.129 g, 0.320 mmol) and the mixture was heated at 60° C. for 18 hours. Additional 2,4-bis(4-methoxyphenyl)-1,3,2,4-dithiadiphosphetane 2,4-disulfide (0.074 g, 0.18 mmol) and the reaction was allowed to heat at reflux until the reaction was determined to be complete. The reaction mixture was concentrated onto Celite® and purified by flash column chromatography using 0-100% ethyl acetate/(1:1 hexanes/dichloromethane). The title compound was obtained as a yellow solid (0.071 g, 49%).

Example 10

Preparation of 3-bromo-1-(4-(trifluoromethyl)phenyl)-1H-1,2,4-triazole (C3)

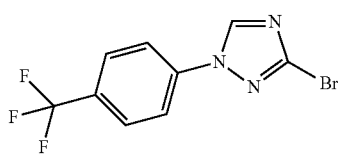

3-Bromo-1-(4-isopropoxyphenyl)-1H-1,2,4-triazole (7.15 g, 48.3 mmol), copper(I) iodide (1.25 g, 6.56 mmol), cesium carbonate (18.9 g, 58.0 mmol), and 1-iodo-4-(trifluoromethyl)benzene (8.29 g, 28.8 mmol) were placed in dimethylsulfoxide (50 mL) and degassed with nitrogen for 10 minutes. The solution was heated at 100° C. for 20 hours. After cooling to room temperature, the reaction mixture was diluted with ethyl acetate and filtered through Celite®. The resulting filter cake was rinsed with additional ethyl acetate (100 mL). Saturated aqueous ammonium chloride was added to the filtrate which was then stirred for 30 minutes. The layers were separated and the aqueous layer was extracted with ethyl acetate (2×50 mL). The combined organic extracts were dried over anhydrous magnesium sulfate and concentrated onto Celite®. Purification by flash column chromatography using 0-100% ethyl acetate/hexanes as eluent provided the title compound as a white solid (5.64 g, 64%): mp 87-89° C.; $^1$H NMR (400 MHz, CDCl$_3$) δ 8.53 (s, 1H), 7.85-7.77 (m, 4H); ESIMS m/z 292 ([M+H]$^+$).

Example 11

Preparation of 4-(1-(4-(trifluoromethyl)phenyl)-1H-1,2,4-triazol-3-yl)aniline (C4)

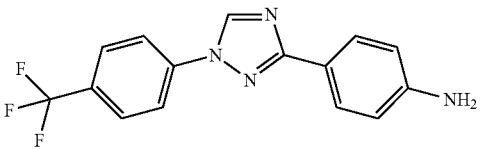 [SMILES: Nc1ccc(-c2ncn(-c3ccc(C(F)(F)F)cc3)n2)cc1]

Placed 3-bromo-1-(4-(trifluoromethyl)phenyl)-1H-1,2,4-triazole (C3) (8.64 g, 29.6 mmol), 4-(4,4,5,5-tetramethyl-1,3,2-dioxaborolan-2-yl)aniline (7.42 g, 33.9 mmol), tetrakis(triphenylphosphine) palladium(0) (3.30 g, 2.86 mmol), and potassium carbonate (7.82 g, 56.6 mmol) in 1,2-dimethoxyethane (75 mL) and water (18 mL) and degassed the mixture with nitrogen for 10 minutes. The reaction mixture was heated at 120° C. for 16 hours. The reaction was cooled to room temperature and diluted with ethyl acetate. The resultant salts were filtered and the filtrated layers were separated. The aqueous layer was separated with ethyl acetate (2×). The combined organic layers were dried over anhydrous magnesium sulfate and concentrated onto Celite®. Purification by flash column chromatography using 0-100% ethyl acetate/hexanes as eluent provided the title compound as a yellow solid (5.34 g, 58%): $^1$H NMR (400 MHz, CDCl$_3$) δ 8.60 (s, 1H), 8.03-7.97 (m, 2H), 7.88 (d, J=8.4 Hz, 2H), 7.77 (d, J=8.5 Hz, 2H), 6.79-6.74 (m, 2H), 3.88 (s, 2H); $^{13}$C NMR (101 MHz, CDCl$_3$) δ 163.94, 148.07, 139.68, 129.67, 129.34, 128.04, 127.07, 127.04, 127.00, 126.96, 125.05, 120.50, 119.35, 114.87; $^{19}$F NMR (376 MHz, CDCl3) δ −62.43; ESIMS m/z 305 ([M+H]$^+$).

Example 12

Preparation of 6-fluoro-2'-methoxy-N-(4-(1-(4-(trifluoromethyl)phenyl)-1H-1,2,4-triazol-3-yl)phenyl)-[1,1'-biphenyl]-3-carboxamide (F20)

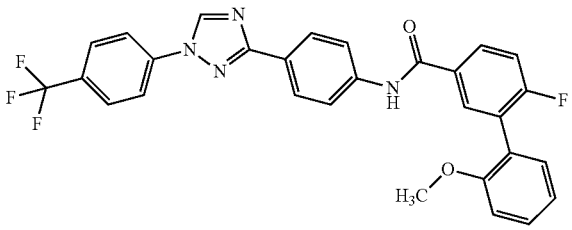 [SMILES: COc1ccccc1-c1cc(C(=O)Nc2ccc(-c3ncn(-c4ccc(C(F)(F)F)cc4)n3)cc2)ccc1F]

To a mixture of 6-fluoro-2'-methoxy-[1,1'-biphenyl]-3-carboxylic acid (0.086 g, 0.35 mmol) in dichloromethane (3 mL) was added oxalyl chloride (0.070 mL, 0.82 mmol) and dimethylformamide (2 drops). After stirring for 3 hours at room temperature, the reaction was concentrated to dryness. The resulting yellow oil was dissolved in anhydrous tetrahydrofuran (2 mL) and added to a solution of 4-(1-(4-(trifluoromethyl)phenyl)-1H-1,2,4-triazol-3-yl)aniline (C4) (0.16 mg, 0.54 mmol) dissolved in tetrahydrofuran (3 mL) and diisopropylethylamine (0.20 mL, 1.15 mmol) and stirred at room temperature for 18 hours. The reaction was diluted with ethyl acetate (10 mL) and washed with saturated aqueous sodium bicarbonate. The aqueous wash was extracted with ethyl acetate (2×5 mL) and the combined organic layers were dried over anhydrous magnesium sulfate. The solution was concentrated onto Celite® and purified by flash column chromatography using 0-100% ethyl acetate/(1:1 hexanes/dichloromethane) as eluent. The relevant fractions were concentrated to give the title compound as a white solid (0.071 g, 23%).

The following examples were prepared according to the procedures disclosed in Example 12:

6-Fluoro-2'-methyl-N-(4-(1-(4-(trifluoromethyl)phenyl)-1H-1,2,4-triazol-3-yl)phenyl)-[1,1'-biphenyl]-3-carboxamide (F58)

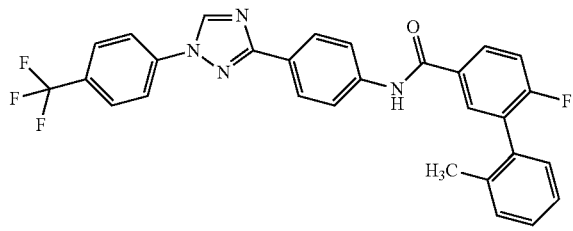 [SMILES: Cc1ccccc1-c1cc(C(=O)Nc2ccc(-c3ncn(-c4ccc(C(F)(F)F)cc4)n3)cc2)ccc1F]

Isolated as a white solid (0.300 g, 58%).

2',6-Difluoro-N-(4-(1-(4-(trifluoromethyl)phenyl)-1H-1,2,4-triazol-3-yl)phenyl)-[1,1'-biphenyl]-3-carboxamide (F59)

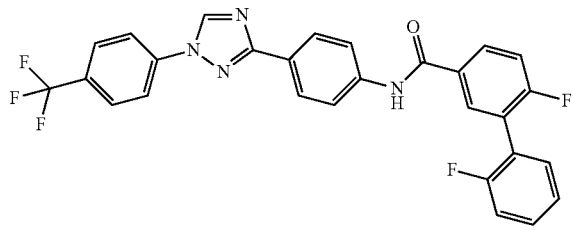 [SMILES: O=C(Nc1ccc(-c2ncn(-c3ccc(C(F)(F)F)cc3)n2)cc1)c1ccc(F)c(-c2ccccc2F)c1]

Isolated as a white solid (0.149 g, 47%).

2'-Methoxy-N-(4-(1-(4-(trifluoromethyl)phenyl)-1H-1,2,4-triazol-3-yl)phenyl)-[1,1'-biphenyl]-3-carboxamide (F60)

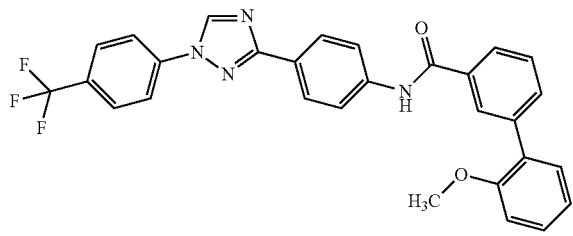 [SMILES: COc1ccccc1-c1cccc(C(=O)Nc2ccc(-c3ncn(-c4ccc(C(F)(F)F)cc4)n3)cc2)c1]

Isolated as an off-white solid (0.192 g, 58%).

6-Methoxy-N-(4-(1-(4-(trifluoromethyl)phenyl)-1H-1,2,4-triazol-3-yl)phenyl)-[1,1'-biphenyl]-3-carboxamide (F61)

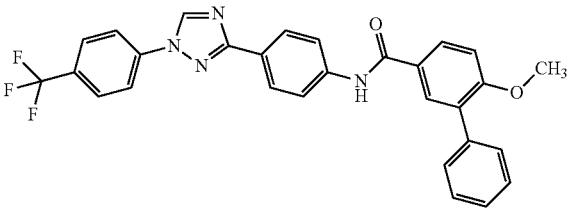 [SMILES: COc1ccc(C(=O)Nc2ccc(-c3ncn(-c4ccc(C(F)(F)F)cc4)n3)cc2)cc1-c1ccccc1]

Isolated as a white solid (0.162 g, 42%).

6-Fluoro-N-(4-(1-(4-(trifluoromethyl)phenyl)-1H-1,2,4-triazol-3-yl)phenyl)-[1,1'-biphenyl]-3-carboxamide (F62)

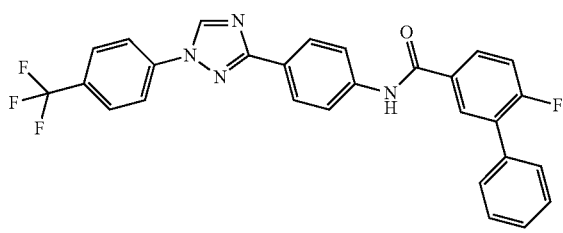 [SMILES: O=C(Nc1ccc(-c2ncn(-c3ccc(C(F)(F)F)cc3)n2)cc1)c1ccc(F)c(-c2ccccc2)c1]

Isolated as a white solid (0.068 g, 25%).

N-(4-(1-(4-(trifluoromethyl)phenyl)-1H-1,2,4-triazol-3-yl)phenyl)picolinamide (F68)

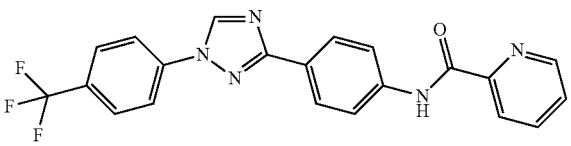 [SMILES: O=C(Nc1ccc(-c2ncn(-c3ccc(C(F)(F)F)cc3)n2)cc1)c1ccccn1]

Isolated as a white solid (0.097 g, 40%).

Example 13

Preparation of (E)-4-bromo-N-((dimethylamino)methylene)benzamide (C5)

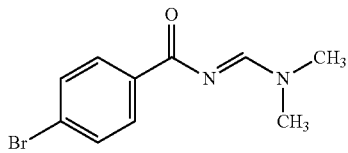

4-Bromobenzamide (21.9 g, 109 mmol) in dimethylformamide dimethylacetal (40 mL) was refluxed for 5 hours. The solution was cooled to room temperature and concentrated. Hexanes was added to the residue and stirred for 30 minutes. The solid was filtered, rinsed with hexanes, and dried overnight to provide the title compound as a tan solid (17.2 g, 59%): mp 103-106° C.; $^1$H NMR (400 MHz, CDCl$_3$) δ 8.63 (s, 1H), 8.17-8.11 (m, 2H), 7.57-7.52 (m, 2H), 3.21 (dd, J=7.2, 0.5 Hz, 6H); ESIMS m/z 257 ([M+ 2H]$^+$).

Example 14

Preparation of 3-(4-bromophenyl)-1H-1,2,4-triazole (C6)

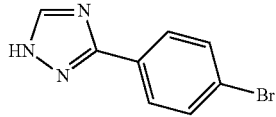 [SMILES: Brc1ccc(-c2nc[nH]n2)cc1]

(E)-4-Bromo-N-((dimethylamino)methylene)benzamide (C5) (17.2 g, 67.3 mmol) in acetic acid (35 mL) was cooled in an ice bath. Hydrazine.monohydrate (6.50 mL, 104 mmol) was slowly added while stirring vigorously. A white solid began to form. The reaction was heated at 90° C. for 3 hours. The solution was cooled and poured into cold water (150 mL). The precipitate was filtered, washed with cold water, and dried under vacuum overnight to provide the title compound as a white solid (14.5 g, 91%): mp>200° C. (dec.); $^1$H NMR (400 MHz, DMSO-d$_6$) δ 14.24 (s, 1H), 8.52 (s, 1H), 8.04-7.91 (m, 2H), 7.75-7.63 (m, 2H); ESIMS m/z 224 ([M]$^+$).

Example 15

Preparation of 3-(4-bromophenyl)-1-(4-(trifluoromethoxy)phenyl)-1H-1,2,4-triazole (C7)

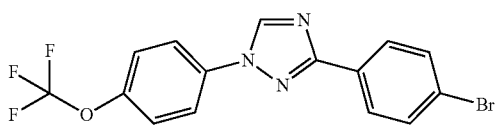 [SMILES: FC(F)(F)Oc1ccc(-n2cnc(-c3ccc(Br)cc3)n2)cc1]

3-(4-Bromophenyl)-1H-1,2,4-triazole (C6) (10.9 g, 48.5 mmol), copper(I) iodide (2.38 g, 12.5 mmol), and cesium carbonate (30.3 g, 93.0 mmol) in a round-bottomed flask was flushed with nitrogen. Dimethylsulfoxide (85 mL) was added, followed by 1-iodo-4-(trifluoromethoxy)benzene (13.2 g, 45.8 mmol). The reaction was degassed for 5 minutes, then heated at 100° C. for 3 days. The reaction was cooled to room temperature, diluted with ethyl acetate, and filtered through a plug of Celite® rinsing with ethyl acetate. To the filtrate was added saturated ammonium chloride and stirred for 1.5 hours. The layers were separated and the aqueous layer was extracted with ethyl acetate (3×). The combined organic layers were dried over magnesium sulfate, filtered, and concentrated onto Celite®. Purification by flash column chromatography using 0-40% EtOAc/hexanes as eluent provided the title compound as an off-white solid (9.65 g, 52%): mp 109-112° C.; $^1$H NMR (400 MHz, CDCl$_3$) δ 8.56 (s, 1H), 8.10-8.03 (m, 2H), 7.83-7.75 (m, 2H), 7.64-7.57 (m, 2H), 7.42-7.35 (m, 2H); ESIMS m/z 386 ([M+2H]$^+$).

Example 16

Preparation of tert-butyl 4-(1-(4-(trifluoromethoxy)phenyl)-1H-1,2,4-triazol-3-yl)phenethylcarbamate (C8)

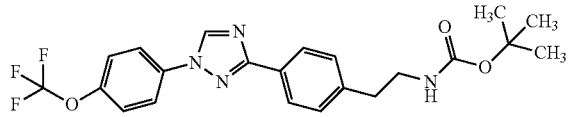 [SMILES: CC(C)(C)OC(=O)NCCc1ccc(-c2ncn(-c3ccc(OC(F)(F)F)cc3)n2)cc1]

To a solution of 3-(4-bromophenyl)-1-(4-(trifluoromethoxy)phenyl)-1H-1,2,4-triazole (C7) (0.13 g, 0.32 mmol) in toluene (4 mL) and water (1 mL) was added potassium (2-((tert-butoxycarbonyl)amino)ethyl)trifluoroborate (0.082 g, 0.33 mmol), palladium(II) acetate (0.027 g, 0.027 mmol), cesium carbonate (0.33 g, 1.0 mmol), and dicyclohexyl(2',6'-diisopropoxy-[1,1'-biphenyl]-2-yl)phosphine (0.016 g, 0.034 mmol), and the solution was stirred under nitrogen and heated to 95° C. for 8 hours. The solution was then cooled and diluted with diethyl ether (5 mL) and adsorbed onto a silica gel pre-column. Flash column chromatography using 0-50% ethyl acetate/hexanes as eluent furnished the title compound as a light tan solid (0.095 g, 63%): mp 149-153° C.; $^1$H NMR (400 MHz, CDCl$_3$) δ 8.56 (s, 1H), 8.18-8.10 (m, 2H), 7.84-7.77 (m, 2H), 7.43-7.35 (m, 2H), 7.31 (d, J=8.2 Hz, 2H), 4.58 (d, J=8.1 Hz, 1H), 3.49-3.34 (m, 1H), 2.87 (t, J=7.0 Hz, 1H), 1.44 (s, 9H); ESIMS m/z 449 ([M+H]$^+$).

Example 17

Preparation of 2-(4-(1-(4-(trifluoromethoxy)phenyl)-1H-1,2,4-triazol-3-yl)phenyl)ethylammonium trifluoroacetate (C9)

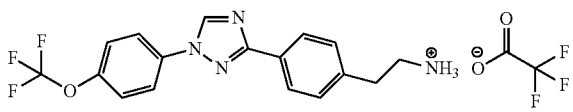 [SMILES: [NH3+]CCc1ccc(-c2ncn(-c3ccc(OC(F)(F)F)cc3)n2)cc1 ; O=C([O-])C(F)(F)F]

To tert-butyl 4-(1-(4-(trifluoromethoxy)phenyl)-1H-1,2,4-triazol-3-yl)phenethylcarbamate (C8) (5.76 g, 12.8 mmol) in dichloromethane (60 mL) was added trifluoroacetic acid (8 mL, 104 mmol) and stirred at room temperature overnight. The solution was concentrated to give a yellow oil. The yellow oil was partially dissolved in dichloromethane and water was added, upon which a precipitate began to form. Saturated sodium bicarbonate was added and the precipitate was filtered and rinsed with dichloromethane to provide the title compound as a white solid (5.43 g, 87%): $^1$H NMR (400 MHz, DMSO-d$_6$) δ 9.41 (s, 1H), 8.11-8.05 (m, 4H), 7.98 (s, 2H), 7.66-7.59 (m, 2H), 7.43 (d, J=8.3 Hz, 2H), 3.12 (s, 2H), 2.99-2.91 (m, 2H); $^{19}$F NMR (376 MHz, DMSO-d$_6$) δ −57.00, −73.64; ESIMS m/z 349 ([M+H]$^+$).

Example 18

Preparation of 2'-methoxy-N-(4-(1-(4-(trifluoromethoxy)phenyl)-1H-1,2,4-triazol-3-yl)phenethyl)-[1,1'-biphenyl]-3-carboxamide (F50)

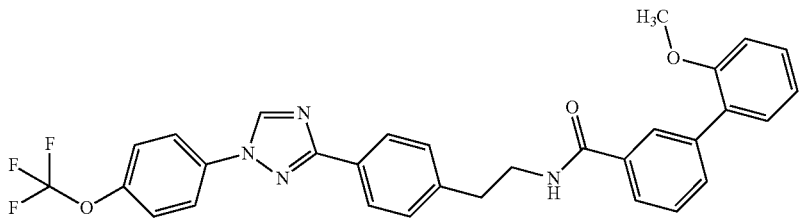 [SMILES: COc1ccccc1-c1cccc(C(=O)NCCc2ccc(-c3ncn(-c4ccc(OC(F)(F)F)cc4)n3)cc2)c1]

2'-Methoxy-[1,1'-biphenyl]-3-carboxylic acid (0.488 g, 2.10 mmol) was dissolved in dichloromethane (10 mL) and oxalyl chloride (0.250 mL, 2.90 mmol) and dimethylformamide (2 drops) were added. Vigorous bubbling occurred and the mixture was stirred at room temperature for 3 hours. The solution was concentrated to give a yellow oil. Half of this solution was added to a solution of 2-(4-(1-(4-(trifluoromethoxy)phenyl)-1H-1,2,4-triazol-3-yl)phenyl)ethylammonium trifluoroacetate (C9) (0.288 g, 0.620 mmol) in anhydrous tetrahydrofuran (5.2 mL) and diisopropylethylamine (0.970 mL, 5.60 mmol). The reaction mixture was stirred overnight at room temperature, quenched with saturated sodium bicarbonate, and extracted with ethyl acetate (3×). The combined organic layers were dried over magnesium sulfate and adsorbed onto Celite®. Purification by flash column chromatography using 0-100% ethyl acetate/1:1 dichloromethane/hexanes as eluent provided the title compound as a white solid (0.181 g, 49%).

The following examples were prepared according to the procedures disclosed in Example 18:

6-Fluoro-N-(4-(1-(4-(trifluoromethoxy)phenyl)-1H-1,2,4-triazol-3-yl)phenethyl)-[1,1'-biphenyl]-3-carboxamide (F51)

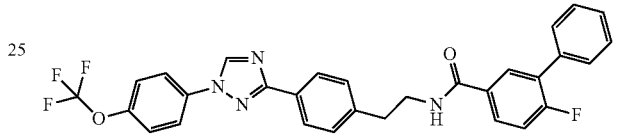

Isolated as a white solid (0.146 g, 46%).

2'-(Dimethylamino)-N-(4-(1-(4-(trifluoromethoxy)phenyl)-1H-1,2,4-triazol-3-yl)phenethyl)-[1,1'-biphenyl]-3-carboxamide (F52)

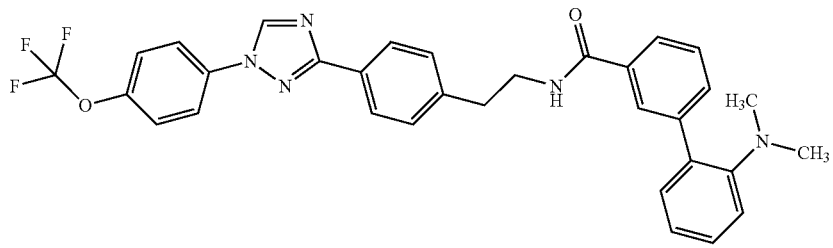 [SMILES: CN(C)c1ccccc1-c1cccc(C(=O)NCCc2ccc(-c3ncn(-c4ccc(OC(F)(F)F)cc4)n3)cc2)c1]

Isolated as a white solid (0.237 g, 41%).

6-Fluoro-2'-methyl-N-(4-(1-(4-(trifluoromethoxy)phenyl)-1H-1,2,4-triazol-3-yl)phenethyl)-[1,1'-biphenyl]-3-carboxamide (F53)

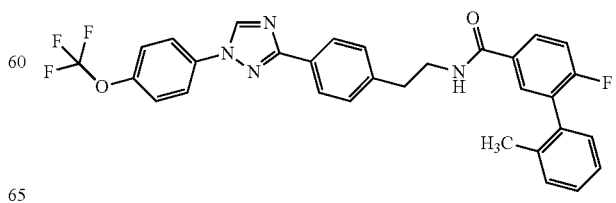

Isolated as a white solid (0.049 g, 5%).

6-Fluoro-2'-methoxy-N-(4-(1-(4-(trifluoromethoxy) phenyl)-1H-1,2,4-triazol-3-yl)phenethyl)-[1,1'-biphenyl]-3-carboxamide (F54)

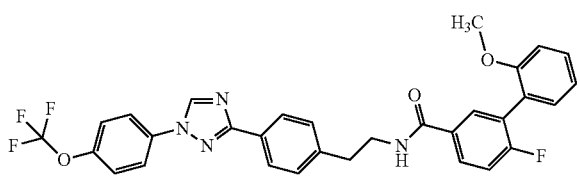 [SMILES: COc1ccccc1-c1cc(C(=O)NCCc2ccc(-c3ncn(-c4ccc(OC(F)(F)F)cc4)n3)cc2)ccc1F]

Isolated as a colorless oil (0.012 g, 1%).

2',6-Difluoro-N-(4-(1-(4-(trifluoromethoxy)phenyl)-1H-1,2,4-triazol-3-yl)phenethyl)-[1,1'-biphenyl]-3-carboxamide (F55)

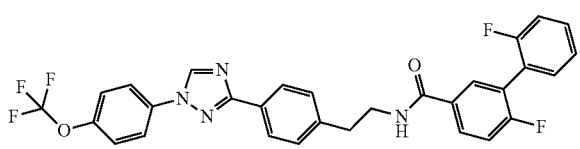 [SMILES: O=C(NCCc1ccc(-c2ncn(-c3ccc(OC(F)(F)F)cc3)n2)cc1)c1ccc(F)c(-c2ccccc2F)c1]

Isolated as a white solid (0.094 g, 26%).

6-Methoxy-N-(4-(1-(4-(trifluoromethoxy)phenyl)-1H-1,2,4-triazol-3-yl)phenethyl)-[1,1'-biphenyl]-3-carboxamide (F56)

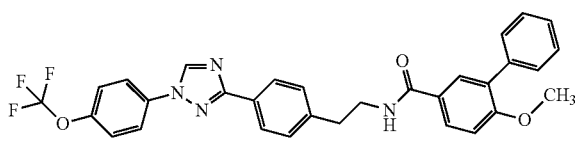 [SMILES: COc1ccc(C(=O)NCCc2ccc(-c3ncn(-c4ccc(OC(F)(F)F)cc4)n3)cc2)cc1-c1ccccc1]

Isolated as a white solid (0.172 g, 52%).

Example 19

Preparation of benzyl 4-bromobenzylcarbamate (C10)

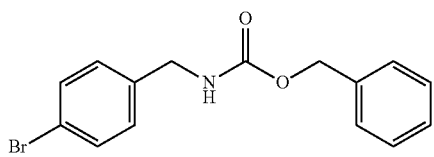 [SMILES: O=C(NCc1ccc(Br)cc1)OCc1ccccc1]

In a round-bottomed flask (500 mL), (4-bromophenyl) methanaminium chloride (10.0 g, 44.9 mmol) and sodium hydroxide (4.00 g, 100 mmol) were dissolved in tetrahydrofuran (80 mL) and water (80 mL). The solution was cooled in an ice water bath and benzyl chloroformate (7.06 mL, 49.4 mmol) was added dropwise. The reaction was allowed to stir for 1 hour. The reaction was poured into a brine solution and extracted with ethyl acetate (2×). The combined organics were dried over magnesium sulfate, filtered, and concentrated to provide the title compound as a white solid (14.8 g, 10%): $^1$H NMR (400 MHz, DMSO-$d_6$) δ 7.92 (t, J=6.0 Hz, 1H), 7.64-7.53 (m, 2H), 7.47-7.33 (m, 5H), 7.32-7.20 (m, 2H), 5.10 (s, 2H), 4.23 (d, J=6.2 Hz, 2H); $^{13}$C NMR (101 MHz, DMSO-$d_6$) δ 156.33, 139.20, 137.05, 131.10, 129.22, 128.33, 127.72, 119.77, 65.42, 43.19; ESIMS m/z 320, 322 ([M+H]$^+$).

Example 19

Preparation of benzyl 4-(4,4,5,5-tetramethyl-1,3,2-dioxaborolan-2-yl)benzylcarbamate (C11)

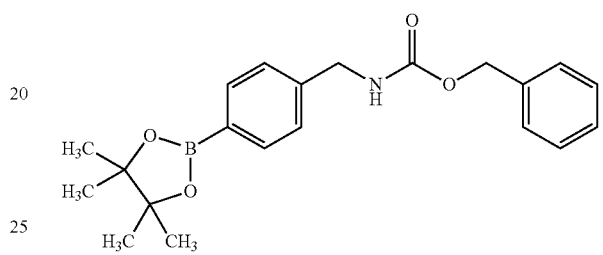

In a round-bottomed flask (500 mL), benzyl 4-bromobenzylcarbamate (C10) (14.1 g, 44.0 mmol), 4,4,4',4',5,5,5',5'-octamethyl-2,2'-bi(1,3,2-dioxaborolane) (12.3 g, 48.4 mmol), and potassium acetate (8.64 g, 88.0 mmol) were suspended in dioxane (200 mL). The suspension was sparged with nitrogen for 5 minutes after which time [1,1'-bisdiphenylphosphinoferrocene]palladium(II) dichloride (1.61 g, 2.20 mmol) was added. The reaction was pumped and purged with nitrogen (2×). The reaction was then warmed to an internal temperature of 70° C., stirring overnight. The reaction was cooled to room temperature, poured into a brine solution, and extracted with ethyl acetate (3×250 mL). The combined organics were dried over magnesium sulfate, filtered, and concentrated onto Celite®. Purification via flash column chromatography (2×) using 0-22% ethyl acetate/hexanes as eluent provided the title compound as a white solid (13.8 g, 81%): $^1$H NMR (400 MHz, DMSO-$d_6$) δ 7.87 (t, J=6.2 Hz, 1H), 7.70-7.60 (m, 2H), 7.46-7.22 (m, 7H), 5.06 (s, 2H), 4.24 (d, J=6.2 Hz, 2H), 1.29 (s, 12H); $^{13}$C NMR (101 MHz, DMSO-$d_6$) δ 156.35, 143.18, 137.12, 134.45, 128.31, 127.69, 126.38, 83.51, 66.32, 65.37, 64.89, 43.83, 24.62; ESIMS m/z 368 ([M+H]$^+$).

Example 20

Preparation of benzyl 4-(1-(4-(trifluoromethoxy) phenyl)-1H-1,2,4-triazol-3-yl)benzylcarbamate (C12)

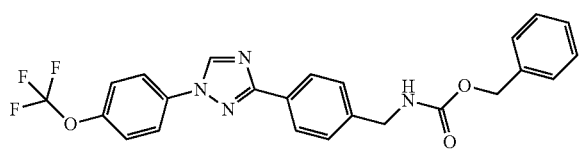 [SMILES: O=C(NCc1ccc(-c2ncn(-c3ccc(OC(F)(F)F)cc3)n2)cc1)OCc1ccccc1]

To a round-bottomed flask (100 mL), 3-bromo-1-(4-(trifluoromethoxy)phenyl)-1H-1,2,4-triazole (5.19 g, 16.8 mmol), benzyl 4-(4,4,5,5-tetramethyl-1,3,2-dioxaborolan-2-yl)benzylcarbamate (C11) (6.80 g, 18.5 mmol) and potassium phosphate (7.15 g, 33.7 mmol) were dissolved in dioxane (140 mL) and water (35.0 mL). The reaction mixture was sparged with nitrogen for 5 minutes after which time [1,1'-bis(di-tert-butylphosphino)ferrocene]dichloropalladium(II) (0.329 g, 0.505 mmol) was added. The flask was sealed and placed under nitrogen atmosphere. The reaction was then heated to an internal temperature of 75° C. for 9 hours. The reaction was poured into a brine solution and extracted with ethyl acetate (4×100 mL). The combined organics were dried over magnesium sulfate, filtered, and concentrated. The resulting residue was purified by flash column chromatography using 10-80% ethyl acetate/hexanes to provide the title compound as an off-white solid (9.31 g, 94%): $^1$H NMR (400 MHz, DMSO-$d_6$) δ 9.40 (s, 1H), 8.16-8.01 (m, 4H), 7.91 (t, J=6.2 Hz, 1H), 7.67-7.58 (m, 2H), 7.48-7.15 (m, 7H), 5.07 (s, 2H), 4.28 (d, J=6.2 Hz, 2H); $^{19}$F NMR (376 MHz, DMSO-$d_6$) δ −56.96; ESIMS m/z 469 ([M+H]$^+$).

Example 21

Preparation of (4-(1-(4-(trifluoromethoxy)phenyl)-1H-1,2,4-triazol-3-yl)phenyl)methanamine—Method A (C13)

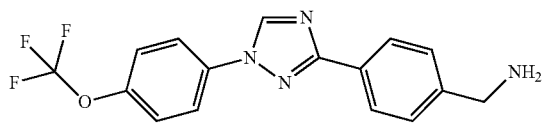 [SMILES: NCc1ccc(-c2ncn(-c3ccc(OC(F)(F)F)cc3)n2)cc1]

In a round-bottomed flask (200 mL), benzyl 4-(1-(4-(trifluoromethoxy)phenyl)-1H-1,2,4-triazol-3-yl)benzylcarbamate (C12) (0.599 g, 1.28 mmol) was diluted with hydrogen bromide (8.00 mL, 45.7 mmol). The suspension was stirred for 1 hour at room temperature. To this suspension was added diethyl ether (100 mL) and the suspension was stirred for 30 minutes. The precipitate was collected via filtration through a glass fritted funnel. The collected solid was then treated with aqueous sodium hydroxide and extracted with ethyl acetate (3×75 mL). The combined organics were dried over magnesium sulfate, filtered, and concentrated to provide the title compound (0.395 g, 92%): $^1$H NMR (400 MHz, DMSO-$d_6$) δ 9.45 (s, 1H), 8.25-8.03 (m, 4H), 7.74-7.62 (m, 2H), 7.60-7.48 (m, 2H), 3.85 (s, 2H); $^{19}$F NMR (376 MHz, DMSO-$d_6$) δ −56.97; ESMIS m/z 318 ([M−NH$_2$+H]$^+$).

Example 22

Preparation of 4-(1-(4-(trifluoromethoxy)phenyl)-1H-1,2,4-triazol-3-yl)benzonitrile (C14)

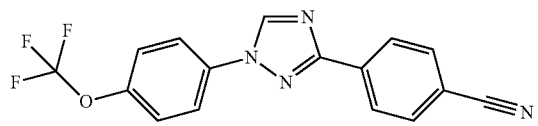 [SMILES: N#Cc1ccc(-c2ncn(-c3ccc(OC(F)(F)F)cc3)n2)cc1]

To a solution of 3-(4-bromophenyl)-1-(4-(trifluoromethoxy)phenyl)-1H-1,2,4-triazole (C7) (4.00 g, 10.4 mmol) in dimethylformamide (30 mL) under nitrogen, zinc cyanide (1.46 g, 12.4 mmol), tetrakis(triphenylphosphine)palladium(0) (0.601 g, 0.0500 mmol) were added and the reaction was heated to 110° C. for 16 hours after degassing with argon. The reaction mixture was cooled to room temperature and was diluted with ethyl acetate and washed with water. The aqueous layer was extracted with ethyl acetate and the combined organic layers were washed with water and brine. The organic layer was dried over sodium sulfate and concentrated under reduced pressure. Purification by flash column chromatography provided an off-white solid which was further triturated with hexanes to provide the title compound as a white solid (3.40 g, 94%): $^1$H NMR (400 MHz, CDCl$_3$) δ 8.60 (s, 1H), 8.31 (d, J=6.6 Hz 2H) 7.81-7.76 (m, 4H), 7.41 (d, J=8.8 Hz, 2H); ESIMS m/z 331 ([M+H]$^+$).

Example 23

Preparation of (4-(1-(4-(trifluoromethoxy)phenyl)-1H-1,2,4-triazol-3-yl)phenyl)methanamine—Method B (C13)

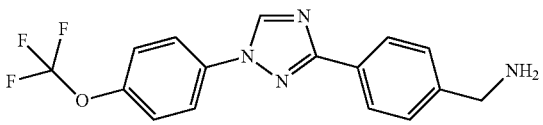 [SMILES: NCc1ccc(-c2ncn(-c3ccc(OC(F)(F)F)cc3)n2)cc1]

To a solution of 4-(1-(4-(trifluoromethoxy)phenyl)-1H-1,2,4-triazol-3-yl)benzonitrile (C14) (3.00 g, 9.09 mmol) in ethanol (30 mL), concentrated hydrochloric acid (3 mL), palladium on carbon (10 weight %, 0.500 g) were added and the reaction mixture was evacuated and purged with hydrogen. The reaction mixture was stirred under hydrogen (50 psi) for 24 hours. The reaction mixture was filtered over Celite®, washed with ethanol and concentrated under reduced pressure to obtain a crude solid, which was washed with diethyl ether to provide the title compound as an off-white solid (2.80 g, 93%): $^1$H NMR (300 MHz, DMSO-$d_6$) δ 9.43 (s, 1H), 8.37 (bs, 3H), 8.18 (d, J=8.1 Hz, 2H), 8.08 (d, J=9.3 Hz, 2H), 7.63 (d, J=8.1 Hz 2H), 4.11-4.07 (m, 2H); ESIMS m/z 335 ([M+H]$^+$).

Example 24

Preparation of N-(4-(1-(4-(trifluoromethoxy)phenyl)-1H-1,2,4-triazol-3-yl)benzyl)-[1,1'-biphenyl]-3-carboxamide (F57)

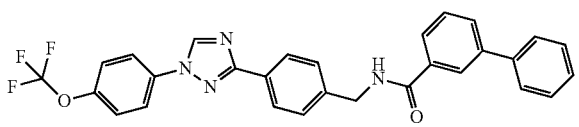 [SMILES: O=C(NCc1ccc(-c2ncn(-c3ccc(OC(F)(F)F)cc3)n2)cc1)c1cccc(-c2ccccc2)c1]

To a solution of [1,1'-biphenyl]-3-carboxylic acid (0.213 g, 1.08 mmol) in dimethylformamide (3.5 mL) was added diisopropylethylamine (0.406 g, 3.14 mmol), 1-[bis(dimethylamino)methylene]-1H-1,2,3-triazolo[4,5-b]pyridinium 3-oxid hexafluorophosphate (0.409 g, 1.08 mmol), and (4-(1-(4-(trifluoromethoxy)phenyl)-1H-1,2,4-triazol-3-yl)phenyl)methanamine (C13) (0.300 g, 0.890 mmol) at room temperature. The resulting reaction mixture was stirred for 16 hours, quenched with hydrochloric acid (2 N), and extracted with ethyl acetate (2×50 mL). The combined organic layer was washed with brine, dried over sodium sulfate, and concentrated under reduced pressure. The crude obtained was purified by flash column chromatography to provide the title compound as an off-white solid (0.0600 g, 13%).

Using the procedures disclosed herein the following list of prophetic molecules having a structure according to Formula One may be made (Table 1).

Cabbage Looper is a member of the moth family Noctuidae. It is found throughout the world. It is attacks cabbage, cauliflower, broccoli, Brussel sprouts, tomatoes, cucumbers, potatoes, kale, turnips, mustard, peppers, eggplant, watermelons, melons, squash, cantaloupe, peas, beans, collards, lettuce, spinach, celery, parsley, beets, peas, alfalfa, soybeans, and cotton. This species is very destructive to plants due to its voracious consumption of leaves. In the case of cabbage, however, they feed not only on the wrapper leaves, but also may bore into the developing head. The larvae

TABLE 1

Structure and Preparation Method for Prophetic Compounds

| No. | Structure | May be Prepared according to Example: |
|---|---|---|
| P1 | 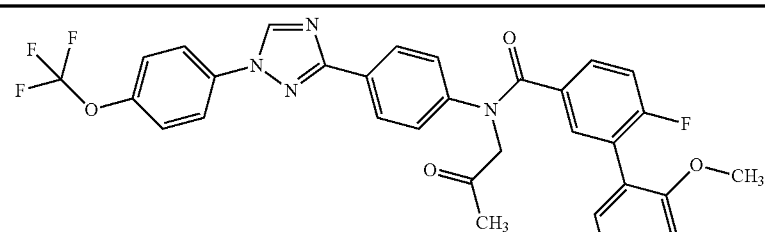 | 5 |
| P2 | 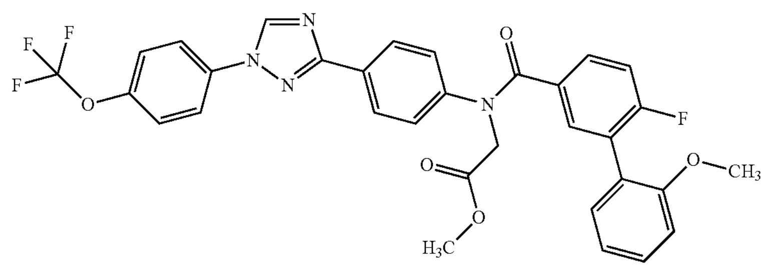 [SMILES: COC(=O)CN(C(=O)c1ccc(F)c(-c2ccccc2OC)c1)c1ccc(-c2ncn(-c3ccc(OC(F)(F)F)cc3)n2)cc1] | 5 |
| P3 | 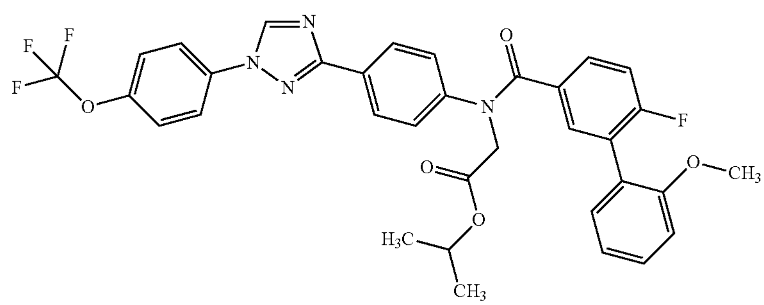 [SMILES: COc1ccccc1-c1cc(C(=O)N(CC(=O)OC(C)C)c2ccc(-c3ncn(-c4ccc(OC(F)(F)F)cc4)n3)cc2)ccc1F] | 5 |

Example A

Bioassays on Beet Armyworm (*Spodoptera exigua*, LAPHEG) ("BAW") and Cabbage Looper (*Trichoplusia ni*, TRIPNI) ("CL")

BAW has few effective parasites, diseases, or predators to lower its population. BAW infests many weeds, trees, grasses, legumes, and field crops. In various places, it is of economic concern upon asparagus, cotton, corn, soybeans, tobacco, alfalfa, sugar beets, peppers, tomatoes, potatoes, onions, peas, sunflowers, and citrus, among other plants. The consume three times their weight in plant material daily. The feeding sites are marked by large accumulations of sticky, wet fecal material.

Consequently, because of the above factors control of these pests is important. Furthermore, molecules that control these pests (BAW and CL), which are known as chewing pests, are useful in controlling other pests that chew on plants.

Certain molecules disclosed in this document were tested against BAW and CEW using procedures described in the following examples. In the reporting of the results, the "BAW & CL Rating Table" was used (See Table Section).

Bioassays on BAW

Bioassays on BAW were conducted using a 128-well diet tray assay. one to five second instar BAW larvae were placed in each well (3 mL) of the diet tray that had been previously filled with 1 mL of artificial diet to which 50 μg/cm² of the test compound (dissolved in 50 μL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Bioassays on Cabbage Looper in CL

Bioassays on CL were conducted using a 128-well diet tray assay. one to five second instar CL larvae were placed in each well (3 mL) of the diet tray that had been previously filled with 1 mL of artificial diet to which 50 μg/cm² of the test compound (dissolved in 50 μL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Example B

Bioassays on Green Peach Aphid (*Myzus persicae*, MYZUPE) ("GPA")

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other plants. GPA also attacks many ornamental crops such as carnation, chrysanthemum, flowering white cabbage, poinsettia, and roses. GPA has developed resistance to many pesticides. Consequently, because of the above factors control of this pest is important. Furthermore, molecules that control this pest (GPA), which is known as a sucking pest, are useful in controlling other pests that suck on plants.

Certain molecules disclosed in this document were tested against GPA using procedures described in the following example. In the reporting of the results, the "GPA Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows.

$$\text{Corrected \% Control} = 100*(X-Y)/X$$

where
X=No. of live aphids on solvent check plants and
Y=No. of live aphids on treated plants The results are indicated in the table entitled "Table ABC: Biological Results" (See Table Section).

Example C

Bioassays on Yellow Fever Mosquito (*Aedes aegypti*, AEDSAE) ("YFM")

YFM prefers to feed on humans during the daytime and is most frequently found in or near human habitations. YFM is a vector for transmitting several diseases. It is a mosquito that can spread the dengue fever and yellow fever viruses. Yellow fever is the second most dangerous mosquito-borne disease after malaria. Yellow fever is an acute viral hemorrhagic disease and up to 50% of severely affected persons without treatment will die from yellow fever. There are an estimated 200,000 cases of yellow fever, causing 30,000 deaths, worldwide each year. Dengue fever is a nasty, viral disease; it is sometimes called "breakbone fever" or "break-heart fever" because of the intense pain it can produce. Dengue fever kills about 20,000 people annually. Consequently, because of the above factors control of this pest is important. Furthermore, molecules that control this pest (YFM), which is known as a sucking pest, are useful in controlling other pests that cause human and animal suffering.

Certain molecules disclosed in this document were tested against YFM using procedures described in the following paragraph. In the reporting of the results, the "YFM Rating Table" was used (See Table Section).

Master plates containing 400 μg of a molecule dissolved in 100 μL of dimethyl sulfoxide (DMSO) (equivalent to a 4000 ppm solution) are used. A master plate of assembled molecules contains 15 μL per well. To this plate, 135 μL of a 90:10 water:acetone mixture is added to each well. A robot (Biomek® NXP Laboratory Automation Workstation) is programmed to dispense 15 μL aspirations from the master plate into an empty 96-well shallow plate ("daughter" plate). There are 6 reps ("daughter" plates) created per master. The created daughter plates are then immediately infested with YFM larvae.

The day before plates are to be treated, mosquito eggs are placed in Millipore water containing liver powder to begin hatching (4 g. into 400 mL). After the daughter plates are created using the robot, they are infested with 220 μL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality.

The results are indicated in the table entitled "Table ABC: Biological Results" (See Table Section).

Agriculturally Acceptable Acid Addition Salts, Salt Derivatives, Solvates, Ester Derivatives, Polymorphs, Isotopes, and Radionuclides Molecules of Formula One may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxyl-methanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide, potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One may be made into ester derivatives. These ester derivatives can then be applied in the same manner as the molecules disclosed in this document is applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) in place of $^1H$.

Molecules of Formula One may be made with different radionuclides. Of particular importance are molecules having $^{14}C$.

Stereoisomers

Molecules of Formula One may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Combinations

In another embodiment, molecules of Formula One may be used in combination (such as, in a compositional mixture, or a simultaneous or sequential application) with one or more compounds each having a mode of action that is the same as, similar to, or different from, the mode of action ("MoA") of the molecules of Formula One. Modes of action include, for example the following: Acetylcholinesterase (AChE) inhibitors; GABA-gated chloride channel antagonists; Sodium channel modulators; Nicotinic acetylcholine (nAChR) agonists; Nicotinic acetylcholine receptor (nAChR) allosteric activators; Chloride channel activators; Juvenile hormone mimics; Miscellaneous non-specific (multi-site) inhibitors; Selective homopteran feeding blockers; Mite growth inhibitors; Microbial disruptors of insect midgut membranes; Inhibitors of mitochondrial ATP synthase; Undouplers of oxidative phosphorylation via disruption of the proton gradient; Nicotinic acetylcholine receptor (nAChR) channel blockers; Inhibitors of chitin biosynthesis, type 0; Inhibitors of chitin biosynthesis, type 1; Moulting disruptor, Dipteran; Ecdysone receptor agonists; Octopamine receptor agonists; Mitochondrial complex III electron transport inhibitors; Mitochondrial complex I electron transport inhibitors; Voltage-dependent sodium channel blockers; Inhibitors of acetyl CoA carboxylase; Mitochondrial complex IV electron transport inhibitors; Mitochondrial complex II electron transport inhibitors; and Ryanodine receptor modulators.

In another embodiment, molecules of Formula One may be used in combination (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, and/or virucidal properties.

In another embodiment, the molecules of Formula One may be used in combination (such as, in a compositional mixture, or a simultaneous or sequential application) with one or more compounds that are antifeedants, bird repellents, chemosterilants, herbicide safeners, insect attractants, insect repellents, mammal repellents, mating disrupters, plant activators, plant growth regulators, and/or synergists.

In another embodiment, the molecules of Formula One may be used in combination (such as, in a compositional mixture, or a simultaneous or sequential application) with "another compound", such as one or more of the following compounds—(3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-diolamine, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, afidopyropen, afoxolaner, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, anabasine sulfate, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzovindiflupyr, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, cholecalciferol, chromafenozide, cinerin I, cinerin II, cinerins, cinidon-ethyl, cinmethylin, cinosulfuron, ciobutide, cisanilide, cismethrin, clacyfos, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclaniliprole, cyclethrin, cycloate, cycloheximide, cycloprate, cycloprothrin, cyclopyrimorate, cyclosulfamuron, cycloxaprid, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmediphan, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-P-potassium, dichlorprop-P-sodium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, enoxastrobin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenaminstrobin, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenquinotrione, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenoxystrobin, flufenprox, flufenpyr, flufenpyr-ethyl, flufiprole, fluhexafon, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, fluralaner, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halauxifen, halauxifen-methyl, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptaflu-thrin, heptenophos, heptopargil, herbimycin, heterophos, hexachloroacetone, hexachlorobenzene, hexachlorobutadi-ene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isofetamid, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, Ivdingjunzhi, Ivxiancaolin, lythidathion, MAA, malathion, maleic hydrazide, malonoben, maltodextrin, MAMA, mancopper, mancozeb, mandipropamid, mandestrobin, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotri-one, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, momfluorothrin, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, napropamide-M, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxathiapiprolin, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentachlorophenyl laurate, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picarbutrazox, picloram, picloram-2-ethylhexyl, picloram-isoctyl, picloram-methyl, picloram-olamine, picloram-potassium, picloram-triethylammonium, picloram-tris(2-hydroxypropyl) ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pyflubumide, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyriminostrobin, pyrimisulfan, pyrimitate, pyrinuron, pyriofenone, pyriprole, pyripropanol, pyriproxyfen, pyrisoxazole, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, rescalure, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetraniliprole, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiafenacil, tiaojiean, tiocarbazil, tioclorim, tioxazafen, tioxymid, tirpate, tolclofos-methyl, tolfenpyrad, tolprocarb, tolpyralate, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyricarb, triclopyr-triethylammonium, tricyclazole, tridemorph, tridiphane, trietazine, trifenmorph, trifenofos, trifloxystrobin, trifloxysulfuron, trifloxysulfuron-sodium, trifludimoxazin, triflumezopyrim, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid. For more information consult the "COMPENDIUM OF PESTICIDE COMMON NAMES" located at alanwood.net. Also consult "THE PESTICIDE MANUAL" 15th Edition, edited by C D S Tomlin, copyright 2009 by British Crop Production Council, or its prior, or more recent editions.

In another embodiment, molecules of Formula One may also be used in combination (such as in a compositional mixture, or a simultaneous or sequential application) with the following compound.

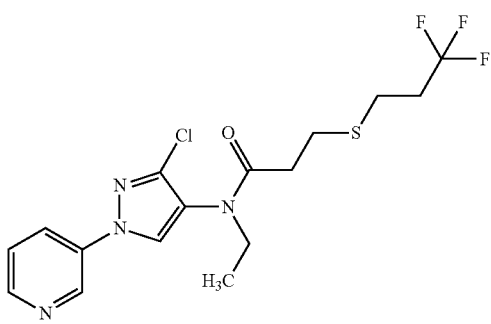 [SMILES: CCN(C(=O)CCSCCC(F)(F)F)c1cn(-c2cccnc2)nc1Cl]

In another embodiment, molecules of Formula One may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on: entomopathogenic fungi (e.g. *Metarhizium anisopliae*); entomopathogenic nematodes (e.g. *Steinernema feltiae*); and entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

In another embodiment, the above possible combinations may be used in a wide variety of weight ratios. For example, a two component mixture, the weight ratio of a molecule of Formula One to another compound, can be from about 100:1 to about 1:100; in another example the weight ratio can be about 50:1 to about 1:50; in another example the weight ratio can be about 20:1 to about 1 to 20; in another example the weight ratio can be about 10:1 to about 1:10; in another example the weight ratio can be about 5:1 to 1:5; in another example the weight ratio can be about 3:1 to about 1:3; in another example the weight ratio can be about 2:1 to about 1:2; and in a final example the weight ratio can be about 1:1. However, preferably, weight ratios less than about 10:1 to about 1:10 are preferred. It is also preferred sometimes to use a three or four component mixture comprising one or more molecules of Formula One and one or more other compounds from the above possible combinations.

TABLE A

| No. | Range of the Weight Ratio of a molecule of the Formula One to another compound |
|---|---|
| 1 | 100:1 to 1:100 |
| 2 | 50:1 to 1:50 |
| 3 | 20:1 to 1:20 |
| 4 | 10:1 to 1:10 |
| 5 | 5:1 to 1:5 |
| 6 | 3:1 to 1:3 |
| 7 | 2:1 to 1:2 |
| 8 | 1:1 |

Weight ratios of a molecule of the Formula One or any agriculturally acceptable salt thereof to another compound envisioned to be synergistic pesticidal compositions may be depicted as X:Y; wherein X is the parts by weight of a molecule of the Formula One or any agriculturally acceptable salt thereof, and Y is the parts by weight of another compound. The numerical range of the parts by weight for X is $0<X\leq100$ and the parts by weight for Y is $0<Y\leq100$ as shown graphically in TABLE B. By way of non-limiting example, the weight ratio of the pesticide to another compound may be about 20:1.

TABLE B

| Another Compound (Y) Parts by weight | 100 | X, Y | | | X, Y | | | | |
|---|---|---|---|---|---|---|---|---|---|
| | 50 | X, Y | X, Y | | | X, Y | | | |
| | 20 | X, Y | | | X, Y | | | | |
| | 15 | X, Y | X, Y | X, Y | X, Y | | | | |
| | 10 | X, Y | | | X, Y | | X, Y | | X, Y |
| | 3 | X, Y | X, Y | | | X, Y | X, Y | X, Y | X, Y |
| | 2 | X, Y | | | X, Y | | X, Y | X, Y | |
| | 1 | X, Y | X, Y | X, Y | X, Y | X, Y | X, Y | X, Y | X, Y |
| | | 1 | 2 | 3 | 10 | 15 | 20 | 50 | 100 |
| | | Molecule of the Formula One (X) Parts by weight | | | | | | | |

Ranges of weight ratios of a molecule of the Formula One or any agriculturally acceptable salt thereof to another compound envisioned to be synergistic pesticidal compositions may be depicted as $X_1:Y_1$ to $X_2:Y_2$, wherein X and Y are defined as above. In one particular embodiment, the range of weight ratios may be $X_1:Y_1$ to $X_2:Y_2$, wherein $X_1>Y_1$ and $X_2<Y_2$. By way of non-limiting example, the range of weight ratios of a molecule of the Formula One or any agriculturally acceptable salt thereof to another compound may be between about 3:1 and about 1:3. In some embodiments, the range of weight ratios may be $X_1:Y_1$ to $X_2:Y_2$, wherein $X_1>Y_1$ and $X_2>Y_2$. By way of non-limiting example, the range of a molecule of the Formula One or any agriculturally acceptable salt thereof to another compound may be between about 15:1 and about 3:1. In further embodiments, the range of weight ratios may be $X_1:Y_1$ to $X_2:Y_2$, wherein $X_1<Y_1$ and $X_2<Y_2$. By way of non-limiting example, the range of weight ratios of a molecule of the Formula One or any agriculturally acceptable salt thereof to another compound may be between about 1:3 and about 1:20.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions. For further information on formulation types see "Catalogue of Pesticide Formulation Types and International Coding System" Technical Monograph n° 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra-low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, the molecules of Formula One may be used to control pests e.g. ants, aphids, beetles, bristletails, cockroaches, crickets, earwigs, fleas, flies, grasshoppers, leafhoppers, lice, locusts, mites, moths, nematodes, scales, symphylans, termites, *thrips*, ticks, wasps, and whiteflies.

In another embodiment, the molecules of Formula One may be used to control pests in the Phyla Nematoda and/or Arthropoda.

In another embodiment, the molecules of Formula One may be used to control pests in the Subphyla Chelicerata, Myriapoda, and/or Hexapoda.

In another embodiment, the molecules of Formula One may be used to control pests in the Classes of Arachnida, Symphyla, and/or Insecta.

In another embodiment, the molecules of Formula One may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.

In another embodiment, the molecules of Formula One may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes puncitventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile*, and *Zabrus tenebrioides*.

In another embodiment, the molecules of Formula One may be used to control pests of the Order Dermaptera.

In another embodiment, the molecules of Formula One may be used to control pests of the Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis*, and *Supella longipalpa*.

In another embodiment, the molecules of Formula One may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana*, and *Stomoxys calcitrans*.

In another embodiment, the molecules of Formula One may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis, and Zulia entrerriana.

In another embodiment, the molecules of Formula One may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richteri, Solenopsis xyloni*, and *Tapinoma sessile*.

In another embodiment, the molecules of Formula One may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis*, and *Reticulitermes virginicus*.

In another embodiment, the molecules of Formula One may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae*, and *Zeuzera pyrina*.

In another embodiment, the molecules of Formula One may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae*, and *Trichodectes canis*.

In another embodiment, the molecules of Formula One may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria*, and *Scudderia furcata*.

In another embodiment, the molecules of Formula One may be used to control pests of the Order Siphonaptera. A non-exhaustive list of particular species includes, but is not limited to, *Ceratophyllus gallinae, Ceratophyllus niger, Ctenocephalides canis, Ctenocephalides felis*, and *Pulex irritans*.

In another embodiment, the molecules of Formula One may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis,* and *Taeniothrips rhopalantennalis, Thrips hawaiiensis, Thrips nigropilosus, Thrips orientalis, Thrips tabaci.*

In another embodiment, the molecules of Formula One may be used to control pests of the Order Thysanura. A non-exhaustive list of particular genera includes, but is not limited to, *Lepisma* spp. and *Thermobia* spp.

In another embodiment, the molecules of Formula One may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae,* and *Varroa destructor.*

In another embodiment, the molecules of Formula One may be used to control pest of the Order Symphyla. A non-exhaustive list of particular sp. includes, but is not limited to, *Scutigerella immaculata.*

In another embodiment, the molecules of Formula One may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis,* and *Rotylenchulus reniformis.*

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Controlling pests of Phyla Nematoda, Arthropoda, and/or Mollusca generally means that pest populations, pest activity, or both, are reduced in an locus. This can come about when:

(a) pest populations are repulsed from a locus;
(b) pests are incapacitated in, or around, a locus; or
(c) pests are exterminated in, or around, a locus.

Of course, a combination of these results can occur. Generally, pest populations, activity, or both are desirably reduced more than fifty percent, preferably more than 90 percent, and most preferably more than 98 percent. Generally, the locus is not in, or on, a human; consequently, the locus is generally a non-human locus.

In another embodiment, the locus to which a molecule of Formula One is applied can be any locus that is inhabited, or that may become inhabited, or that may be traversed, by a pest of Phyla Nematoda, Arthropoda, and/or Mollusca. For example, the locus can be:

(a) where crops, trees, fruits, cereals, fodder species, vines, turf, and/or ornamental plants, are growing;
(b) where domesticated animals are residing;
(c) the interior or exterior surfaces of buildings (such as places where grains are stored);
(d) the materials of construction used in buildings (such as impregnated wood); and
(e) the soil around buildings.

Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a molecule of Formula One when growing various plants.

In another embodiment, molecules of Formula One are generally used in amounts from about 0.0001 grams per hectare to about 5000 grams per hectare to provide control. In another embodiment, it is preferred that molecules of Formula One are used in amounts from about 0.001 grams per hectare to about 500 grams per hectare. In another embodiment, it is more preferred that molecules of Formula One are used in amounts from about 0.01 gram per hectare to about 50 grams per hectare.

The molecules of Formula One may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). Furthermore, such molecules may be used during times when pest activity is low, such as before the plants that are growing begin to produce valuable agricultural commodities. Such times include the early planting season when pest pressure is usually low.

The molecules of Formula One can be applied to the foliar and fruiting portions of plants to control pests. The molecules will either come in direct contact with the pest, or the pest will consume the pesticide when eating leaf, fruit mass, or extracting sap, that contains the pesticide. The molecules of Formula One can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula One.

The molecules of Formula One can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the molecules of Formula One may be desirable to control newly emerged larvae.

Systemic movement of pesticides in plants may be utilized to control pests on one portion of the plant by applying (for example by spraying an area) the molecules of Formula One to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the molecules of Formula One may further enhance the ability of a plant to better withstand stressful growing conditions. This results in a healthier, more vigorous plant, which can lead to higher yields at harvest time. Generally, about 1 gram of the molecules of Formula One to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the molecules of Formula One may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The molecules of Formula One may be used for controlling endoparasites and ectoparasites in the veterinary medicine sector or in the field of non-human animal keeping. The molecules of Formula One are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The molecules of Formula One may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The molecules of Formula One may also be used for controlling parasitic worms, especially of the intestine, in the animals listed above.

The molecules of Formula One may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The molecules of Formula One may also be used on such new invasive species to control them in such new environment.

The molecules of Formula One may also be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A molecule according to Formula One can be tested to determine its efficacy against pests. Furthermore, mode of action studies can be conducted to determine if said molecule has a different mode of action than other pesticides. Thereafter, such acquired data can be disseminated, such as by the internet, to third parties.

The headings in this document are for convenience only and must not be used to interpret any portion hereof.

Table Section

TABLE 2

| | Structures for Intermediates | | |
|---|---|---|---|
| No. | Structure | App. | Prepared according to Example: |
| C1 | 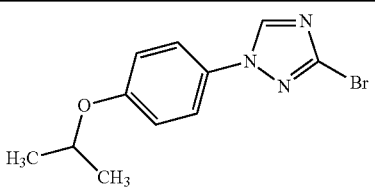 | Yellow Oil | 1 |

TABLE 2-continued

Structures for Intermediates

| No. | Structure | App. | Prepared according to Example: |
|---|---|---|---|
| C2 | 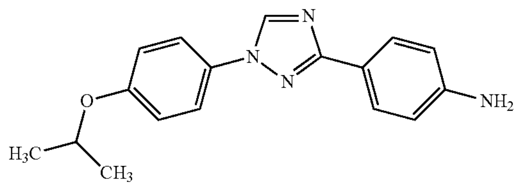 [SMILES: CC(C)Oc1ccc(-n2cnc(-c3ccc(N)cc3)n2)cc1] | Tan Solid | 2 |
| C3 | 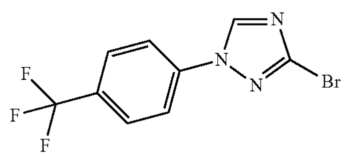 [SMILES: FC(F)(F)c1ccc(-n2cnc(Br)n2)cc1] | White Solid | 10 |
| C4 | 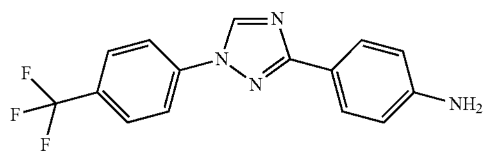 [SMILES: Nc1ccc(-c2ncn(-c3ccc(C(F)(F)F)cc3)n2)cc1] | Yellow Solid | 11 |
| C7 | 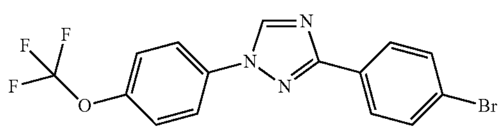 [SMILES: FC(F)(F)Oc1ccc(-n2cnc(-c3ccc(Br)cc3)n2)cc1] | Off-white solid | 15 |
| C8 | 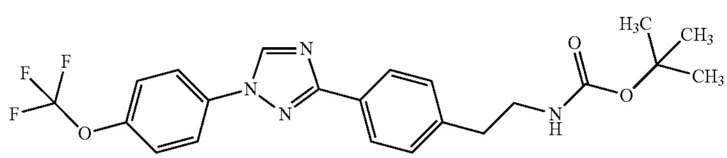 [SMILES: CC(C)(C)OC(=O)NCCc1ccc(-c2ncn(-c3ccc(OC(F)(F)F)cc3)n2)cc1] | Light tan solid | 16 |
| C9 | 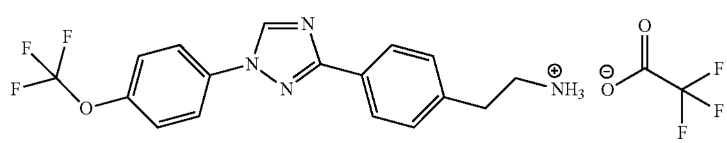 [SMILES: [NH3+]CCc1ccc(-c2ncn(-c3ccc(OC(F)(F)F)cc3)n2)cc1 ; O=C([O-])C(F)(F)F] | White solid | 17 |
| C11 | 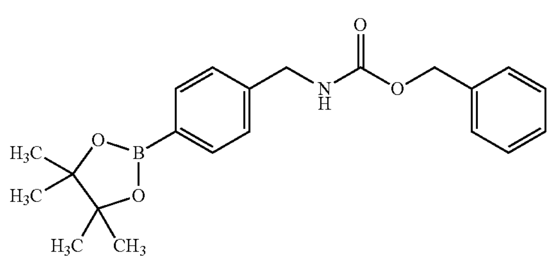 [SMILES: CC1(C)OB(c2ccc(CNC(=O)OCc3ccccc3)cc2)OC1(C)C] | White solid. | 19 |
| C12 | 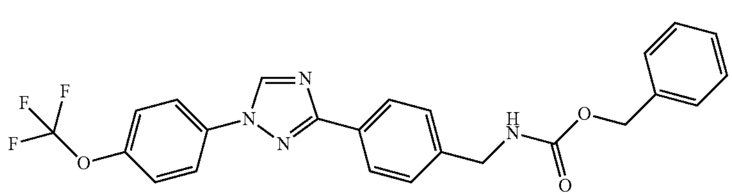 [SMILES: O=C(NCc1ccc(-c2ncn(-c3ccc(OC(F)(F)F)cc3)n2)cc1)OCc1ccccc1] | Off-white solid | 20 |

TABLE 2-continued
Structures for Intermediates
| No. | Structure | App. | Prepared according to Example: |
|---|---|---|---|
| C13 | 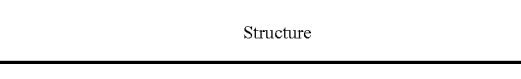 | Off-white solid | 21, 23 |
TABLE 3
Structures for Molecules of Formula One
| No. | Structure | App. | Prepared according to Example: |
|---|---|---|---|
| F1 | 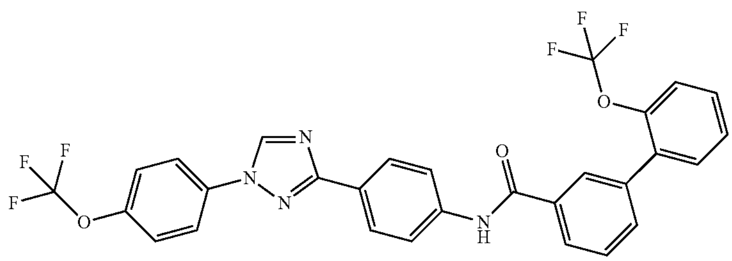 [SMILES: O=C(Nc1ccc(-c2ncn(-c3ccc(OC(F)(F)F)cc3)n2)cc1)c1cccc(-c2ccccc2OC(F)(F)F)c1] | Off-White Solid | 4 |
| F2 | 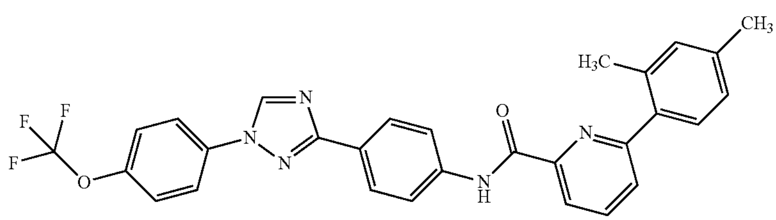 [SMILES: Cc1ccc(-c2cccc(C(=O)Nc3ccc(-c4ncn(-c5ccc(OC(F)(F)F)cc5)n4)cc3)n2)c(C)c1] | Tan Solid | 4 |
| F3 | 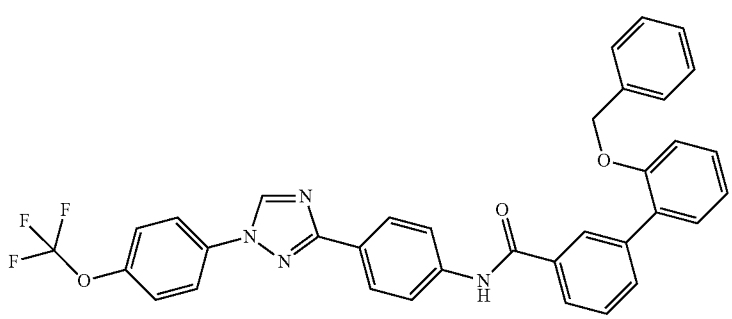 [SMILES: O=C(Nc1ccc(-c2ncn(-c3ccc(OC(F)(F)F)cc3)n2)cc1)c1cccc(-c2ccccc2OCc2ccccc2)c1] | White Solid | 4 |
| F4 | 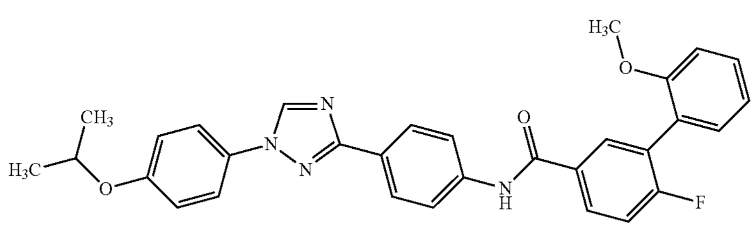 | White Solid | 3 |

TABLE 3-continued

Structures for Molecules of Formula One

| No. | Structure | App. | Prepared according to Example: |
|---|---|---|---|
| F5 | 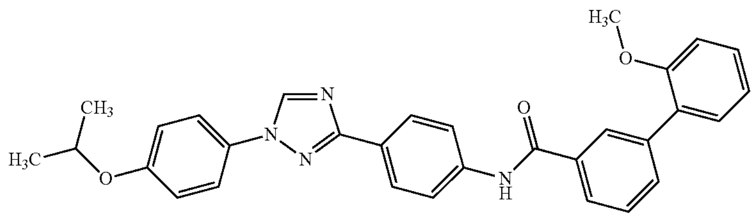 [SMILES: COc1ccccc1-c1cccc(C(=O)Nc2ccc(-c3ncn(-c4ccc(OC(C)C)cc4)n3)cc2)c1] | Off-White Solid | 3 |
| F6 | 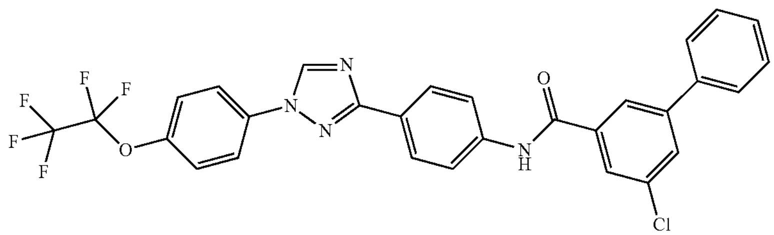 [SMILES: O=C(Nc1ccc(-c2ncn(-c3ccc(OC(F)(F)C(F)(F)F)cc3)n2)cc1)c1cc(Cl)cc(-c2ccccc2)c1] | Off-White Solid | 7 |
| F7 | 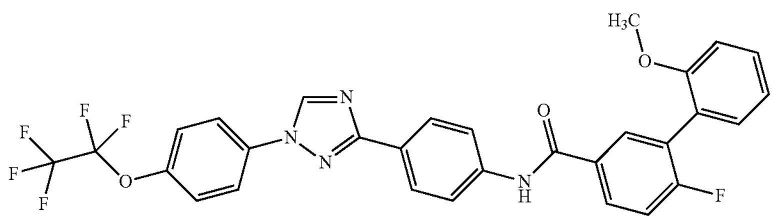 [SMILES: COc1ccccc1-c1cc(C(=O)Nc2ccc(-c3ncn(-c4ccc(OC(F)(F)C(F)(F)F)cc4)n3)cc2)ccc1F] | Off-White Solid | 7 |
| F8 | 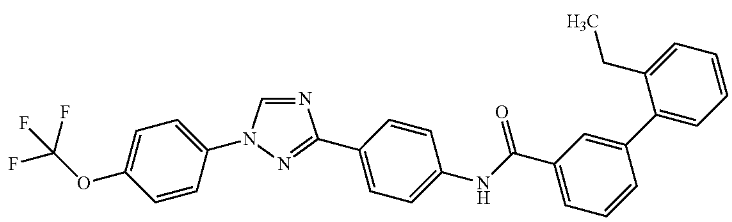 [SMILES: CCc1ccccc1-c1cccc(C(=O)Nc2ccc(-c3ncn(-c4ccc(OC(F)(F)F)cc4)n3)cc2)c1] | White Solid | 4 |
| F9 | 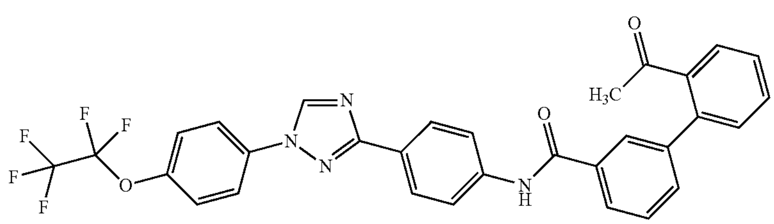 [SMILES: CC(=O)c1ccccc1-c1cccc(C(=O)Nc2ccc(-c3ncn(-c4ccc(OC(F)(F)C(F)(F)F)cc4)n3)cc2)c1] | Off-White Solid | 7 |
| F10 | 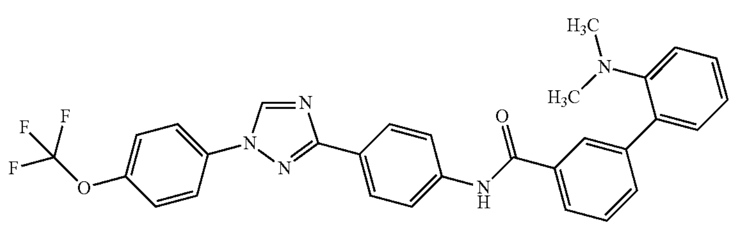 [SMILES: CN(C)c1ccccc1-c1cccc(C(=O)Nc2ccc(-c3ncn(-c4ccc(OC(F)(F)F)cc4)n3)cc2)c1] | Yellow Oil | 4 |

TABLE 3-continued

Structures for Molecules of Formula One

| No. | Structure | App. | Prepared according to Example: |
|---|---|---|---|
| F11 | 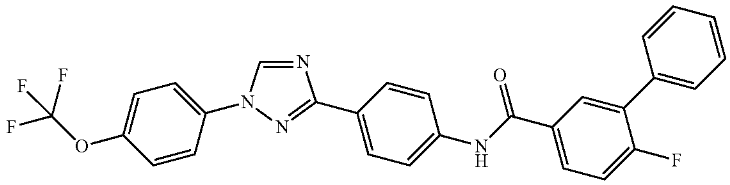 [SMILES: O=C(Nc1ccc(-c2ncn(-c3ccc(OC(F)(F)F)cc3)n2)cc1)c1ccc(F)c(-c2ccccc2)c1] | White Solid | 4 |
| F12 | 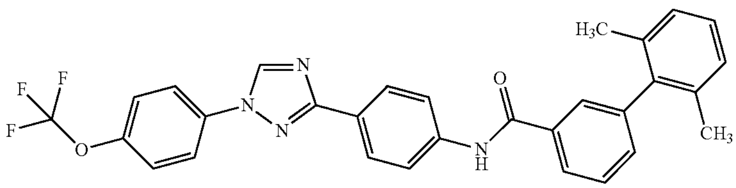 [SMILES: Cc1cccc(C)c1-c1cccc(C(=O)Nc2ccc(-c3ncn(-c4ccc(OC(F)(F)F)cc4)n3)cc2)c1] | Off-White Solid | 4 |
| F13 | 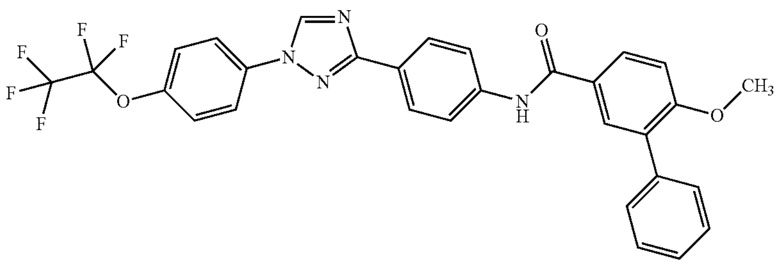 [SMILES: COc1ccc(C(=O)Nc2ccc(-c3ncn(-c4ccc(OC(F)(F)C(F)(F)F)cc4)n3)cc2)cc1-c1ccccc1] | White Solid | 7 |
| F14 | 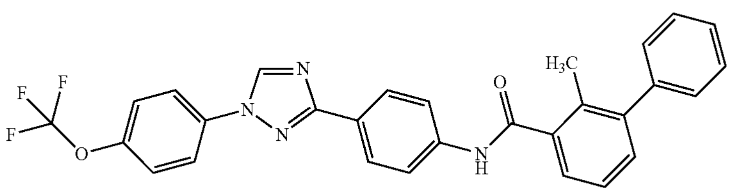 [SMILES: Cc1c(C(=O)Nc2ccc(-c3ncn(-c4ccc(OC(F)(F)F)cc4)n3)cc2)cccc1-c1ccccc1] | White Solid | 4 |
| F15 | 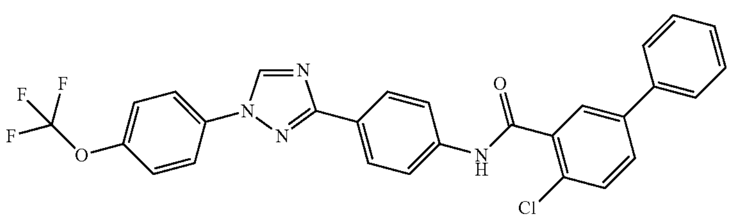 | White Solid | 4 |
| F16 | 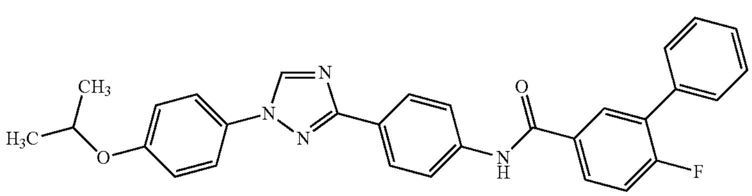 [SMILES: CC(C)Oc1ccc(-n2cnc(-c3ccc(NC(=O)c4ccc(F)c(-c5ccccc5)c4)cc3)n2)cc1] | White Solid | 3 |
| F17 | 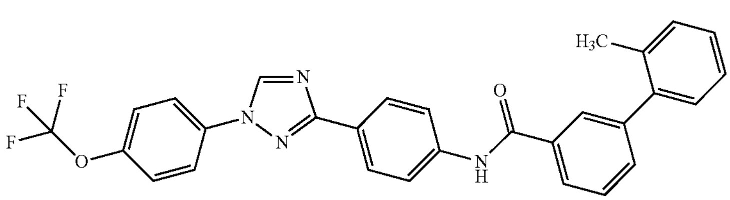 [SMILES: Cc1ccccc1-c1cccc(C(=O)Nc2ccc(-c3ncn(-c4ccc(OC(F)(F)F)cc4)n3)cc2)c1] | Off-White Solid | 4 |

TABLE 3-continued

Structures for Molecules of Formula One

| No. | Structure | App. | Prepared according to Example: |
|---|---|---|---|
| F18 | 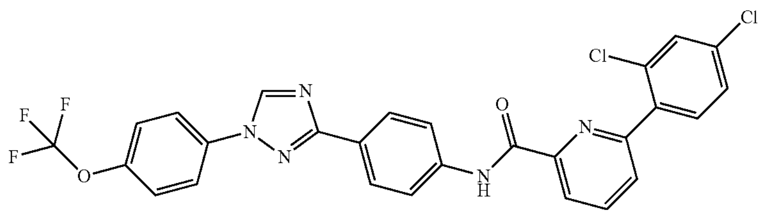 [SMILES: O=C(Nc1ccc(-c2ncn(-c3ccc(OC(F)(F)F)cc3)n2)cc1)c1cccc(-c2ccc(Cl)cc2Cl)n1] | Off-White | 4 |
| F19 | 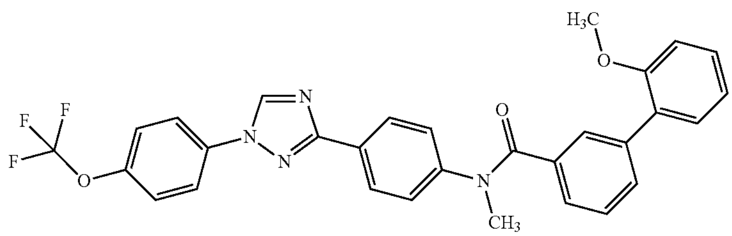 [SMILES: COc1ccccc1-c1cccc(C(=O)N(C)c2ccc(-c3ncn(-c4ccc(OC(F)(F)F)cc4)n3)cc2)c1] | Colorless Oil | 5 |
| F20 | 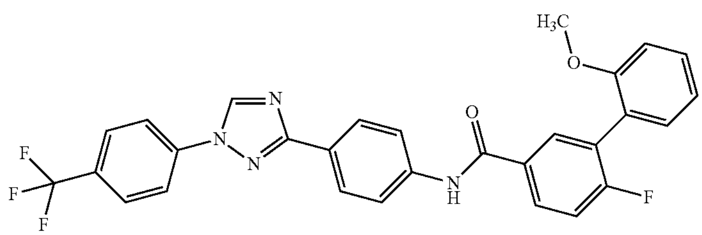 [SMILES: COc1ccccc1-c1cc(C(=O)Nc2ccc(-c3ncn(-c4ccc(C(F)(F)F)cc4)n3)cc2)ccc1F] | White Solid | 12 |
| F21 | 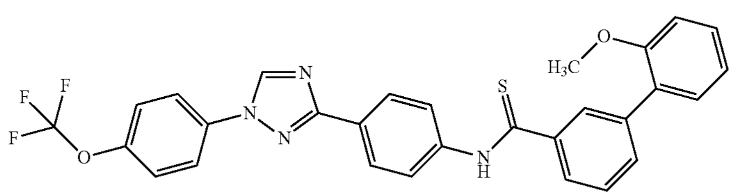 | Yellow Solid | 6 |
| F22 | 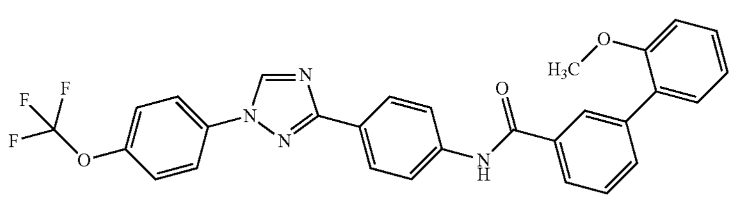 [SMILES: COc1ccccc1-c1cccc(C(=S)Nc2ccc(-c3ncn(-c4ccc(OC(F)(F)F)cc4)n3)cc2)c1] | White Solid | 4 |
| F23 | 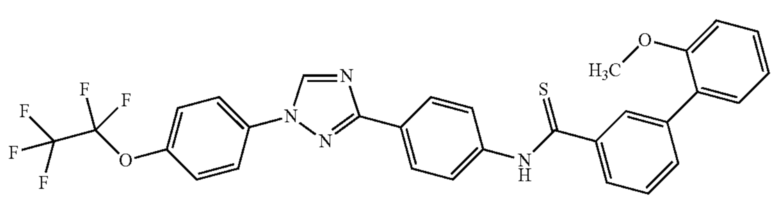 | Yellow Solid | 9 |

TABLE 3-continued

Structures for Molecules of Formula One

| No. | Structure | App. | Prepared according to Example: |
|---|---|---|---|
| F24 | 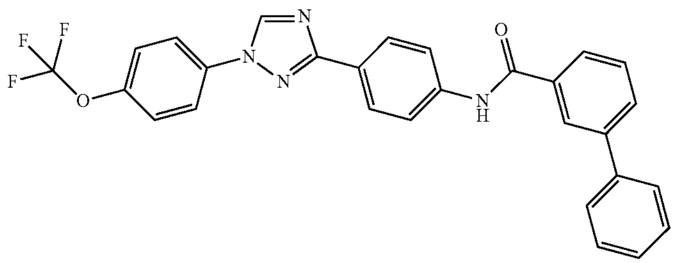 [SMILES: O=C(Nc1ccc(-c2ncn(-c3ccc(OC(F)(F)F)cc3)n2)cc1)c1cccc(-c2ccccc2)c1] | White Solid | 4 |
| F25 | 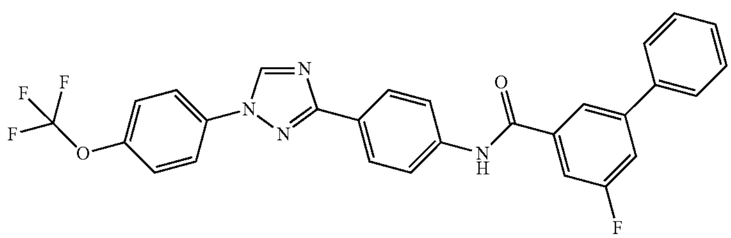 [SMILES: O=C(Nc1ccc(-c2ncn(-c3ccc(OC(F)(F)F)cc3)n2)cc1)c1cc(F)cc(-c2ccccc2)c1] | Off-White Solid | 4 |
| F26 | 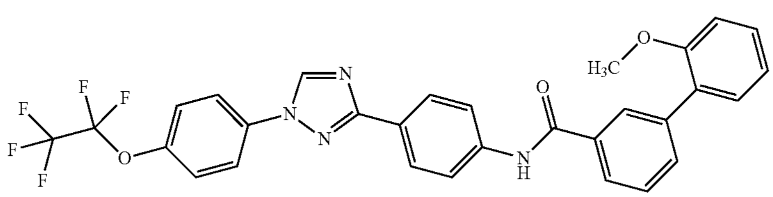 [SMILES: COc1ccccc1-c1cccc(C(=O)Nc2ccc(-c3ncn(-c4ccc(OC(F)(F)C(F)(F)F)cc4)n3)cc2)c1] | White Solid | 7 |
| F27 | 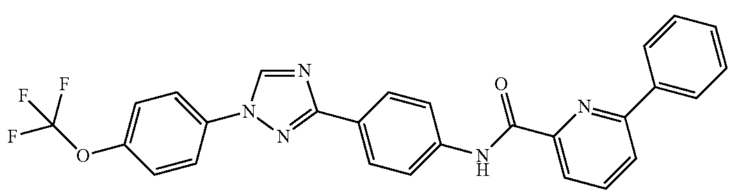 [SMILES: O=C(Nc1ccc(-c2ncn(-c3ccc(OC(F)(F)F)cc3)n2)cc1)c1cccc(-c2ccccc2)n1] | White Solid | 4 |
| F28 | 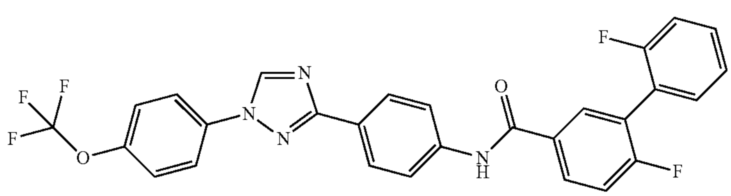 [SMILES: O=C(Nc1ccc(-c2ncn(-c3ccc(OC(F)(F)F)cc3)n2)cc1)c1ccc(F)c(-c2ccccc2F)c1] | Off-White Solid | 4 |
| F29 | 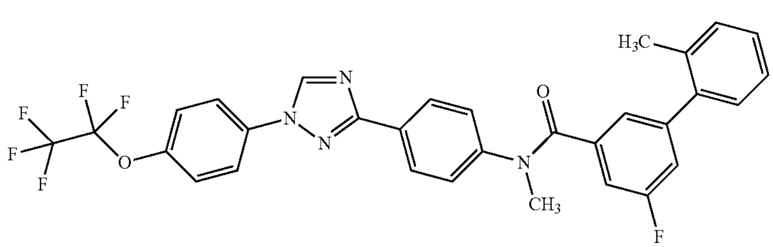 [SMILES: Cc1ccccc1-c1cc(F)cc(C(=O)N(C)c2ccc(-c3ncn(-c4ccc(OC(F)(F)C(F)(F)F)cc4)n3)cc2)c1] | Colorless Oil | 8 |

TABLE 3-continued

Structures for Molecules of Formula One

| No. | Structure | App. | Prepared according to Example: |
|---|---|---|---|
| F30 | 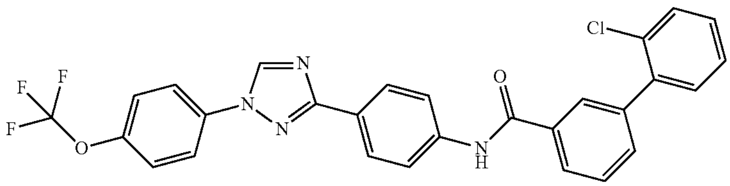 [SMILES: O=C(Nc1ccc(-c2ncn(-c3ccc(OC(F)(F)F)cc3)n2)cc1)c1cccc(-c2ccccc2Cl)c1] | White Solid | 4 |
| F31 | 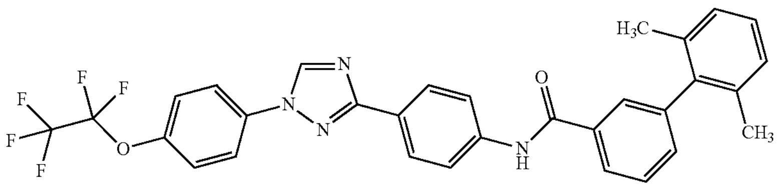 [SMILES: Cc1cccc(C)c1-c1cccc(C(=O)Nc2ccc(-c3ncn(-c4ccc(OC(F)(F)C(F)(F)F)cc4)n3)cc2)c1] | Off-White Solid | 7 |
| F32 | 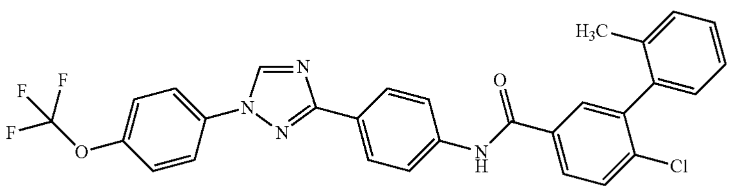 [SMILES: Cc1ccccc1-c1cc(C(=O)Nc2ccc(-c3ncn(-c4ccc(OC(F)(F)F)cc4)n3)cc2)ccc1Cl] | White Solid | 4 |
| F33 | 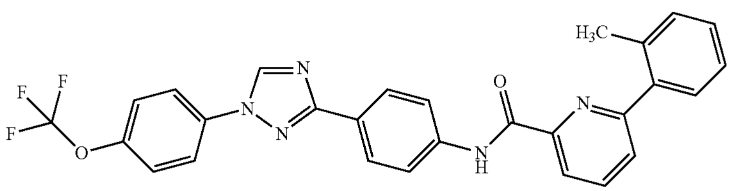 [SMILES: Cc1ccccc1-c1cccc(C(=O)Nc2ccc(-c3ncn(-c4ccc(OC(F)(F)F)cc4)n3)cc2)n1] | White Solid | 4 |
| F34 | 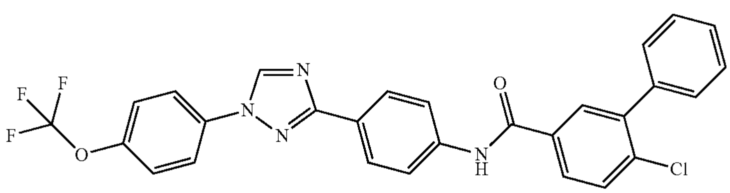 | Tan Solid | 4 |
| F35 | 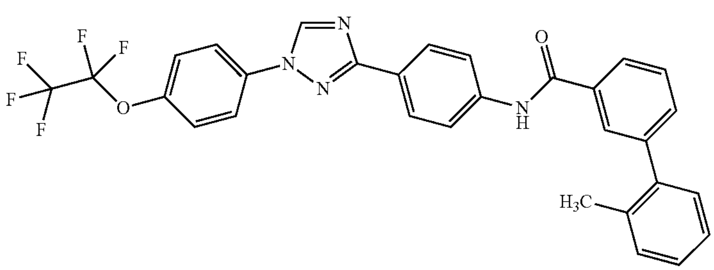 [SMILES: Cc1ccccc1-c1cccc(C(=O)Nc2ccc(-c3ncn(-c4ccc(OC(F)(F)C(F)(F)F)cc4)n3)cc2)c1] | White Solid | 7 |
| F36 | 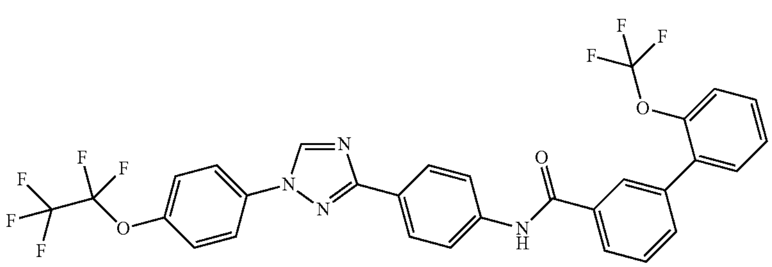 [SMILES: O=C(Nc1ccc(-c2ncn(-c3ccc(OC(F)(F)C(F)(F)F)cc3)n2)cc1)c1cccc(-c2ccccc2OC(F)(F)F)c1] | Off-White Solid | 7 |

TABLE 3-continued

Structures for Molecules of Formula One

| No. | Structure | App. | Prepared according to Example: |
|---|---|---|---|
| F37 | 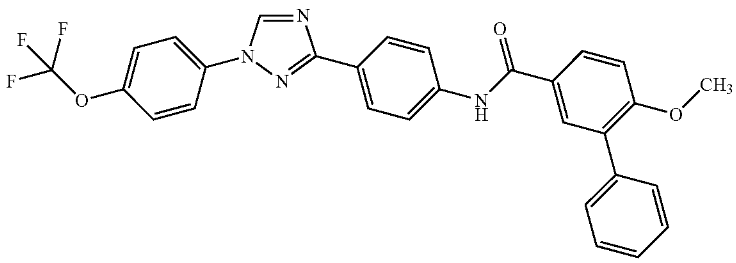 [SMILES: COc1ccc(C(=O)Nc2ccc(-c3ncn(-c4ccc(OC(F)(F)F)cc4)n3)cc2)cc1-c1ccccc1] | White Solid | 4 |
| F38 | 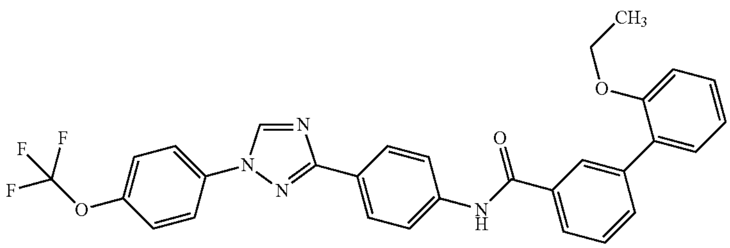 [SMILES: CCOc1ccccc1-c1cccc(C(=O)Nc2ccc(-c3ncn(-c4ccc(OC(F)(F)F)cc4)n3)cc2)c1] | White Solid | 4 |
| F39 | 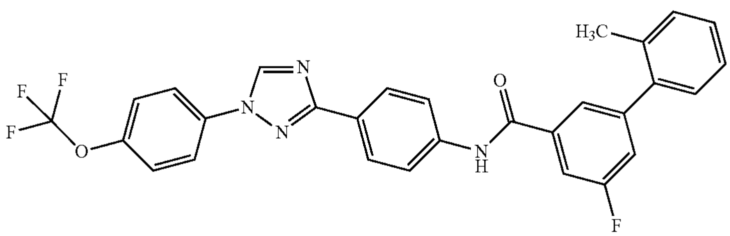 [SMILES: Cc1ccccc1-c1cc(F)cc(C(=O)Nc2ccc(-c3ncn(-c4ccc(OC(F)(F)F)cc4)n3)cc2)c1] | Orange Oily Solid | 4 |
| F40 | 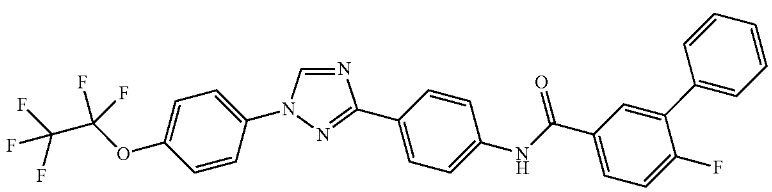 [SMILES: O=C(Nc1ccc(-c2ncn(-c3ccc(OC(F)(F)C(F)(F)F)cc3)n2)cc1)c1ccc(F)c(-c2ccccc2)c1] | Off-White Solid | 7 |
| F41 | 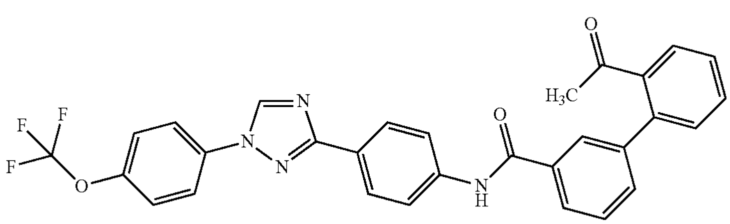 [SMILES: CC(=O)c1ccccc1-c1cccc(C(=O)Nc2ccc(-c3ncn(-c4ccc(OC(F)(F)F)cc4)n3)cc2)c1] | Off-White Solid | 4 |
| F42 | 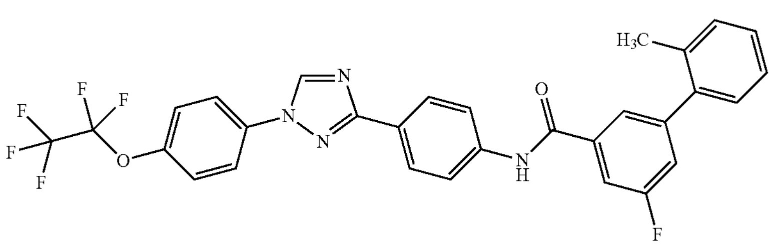 [SMILES: Cc1ccccc1-c1cc(F)cc(C(=O)Nc2ccc(-c3ncn(-c4ccc(OC(F)(F)C(F)(F)F)cc4)n3)cc2)c1] | Off-White Solid | 7 |

TABLE 3-continued

Structures for Molecules of Formula One

| No. | Structure | App. | Prepared according to Example: |
|---|---|---|---|
| F43 | 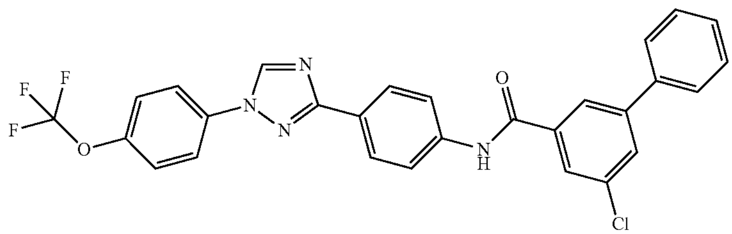 [SMILES: O=C(Nc1ccc(-c2ncn(-c3ccc(OC(F)(F)F)cc3)n2)cc1)c1cc(Cl)cc(-c2ccccc2)c1] | Off-White Solid | 4 |
| F44 | 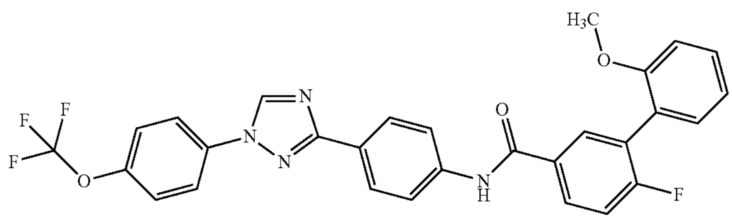 [SMILES: COc1ccccc1-c1cc(C(=O)Nc2ccc(-c3ncn(-c4ccc(OC(F)(F)F)cc4)n3)cc2)ccc1F] | White Solid | 4 |
| F45 | 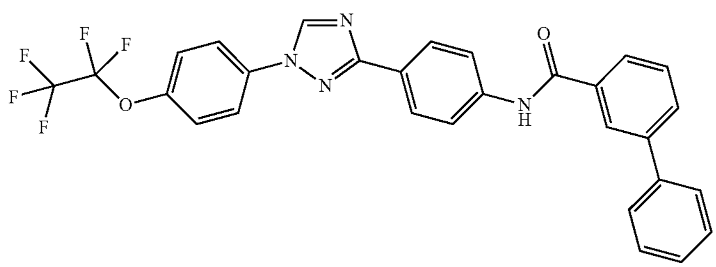 [SMILES: O=C(Nc1ccc(-c2ncn(-c3ccc(OC(F)(F)C(F)(F)F)cc3)n2)cc1)c1cccc(-c2ccccc2)c1] | White Solid | 7 |
| F46 | 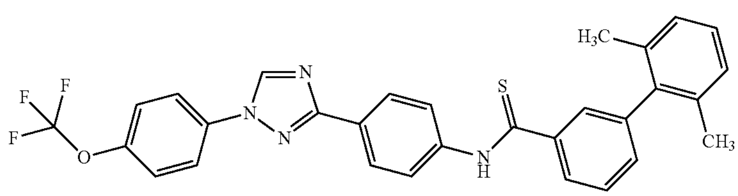 [SMILES: Cc1cccc(C)c1-c1cccc(C(=S)Nc2ccc(-c3ncn(-c4ccc(OC(F)(F)F)cc4)n3)cc2)c1] | Yellow Oil | 6 |
| F47 | 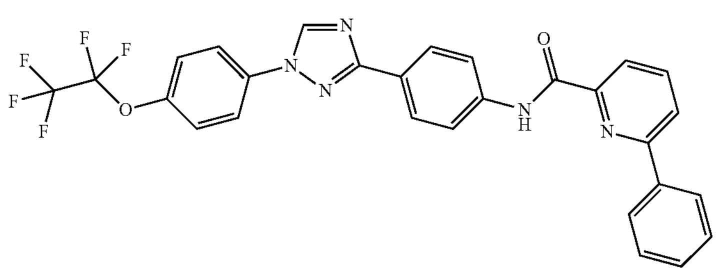 [SMILES: O=C(Nc1ccc(-c2ncn(-c3ccc(OC(F)(F)C(F)(F)F)cc3)n2)cc1)c1cccc(-c2ccccc2)n1] | White Solid | 7 |
| F48 | 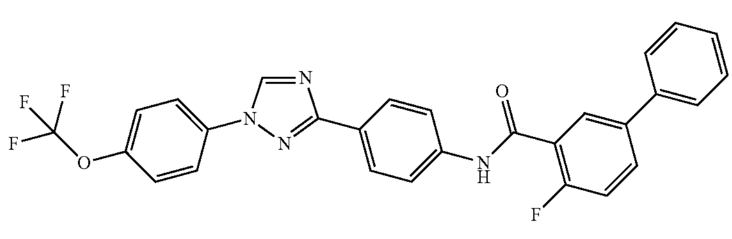 [SMILES: O=C(Nc1ccc(-c2ncn(-c3ccc(OC(F)(F)F)cc3)n2)cc1)c1cc(-c2ccccc2)ccc1F] | White Solid | 4 |

TABLE 3-continued

Structures for Molecules of Formula One

| No. | Structure | App. | Prepared according to Example: |
|---|---|---|---|
| F49 | 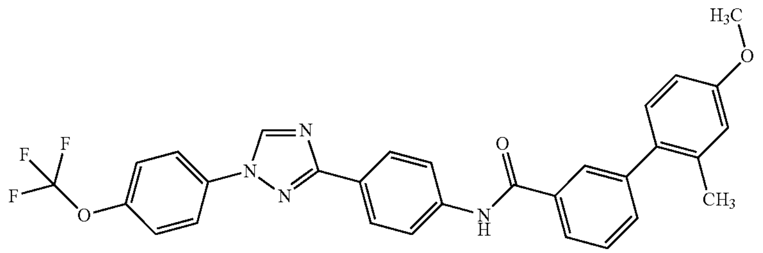 [SMILES: COc1ccc(-c2cccc(C(=O)Nc3ccc(-c4ncn(-c5ccc(OC(F)(F)F)cc5)n4)cc3)c2)c(C)c1] | White Solid | 4 |
| F50 | 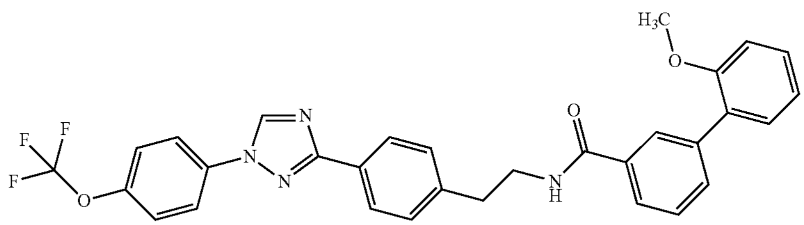 [SMILES: COc1ccccc1-c1cccc(C(=O)NCCc2ccc(-c3ncn(-c4ccc(OC(F)(F)F)cc4)n3)cc2)c1] | White Solid | 18 |
| F51 | 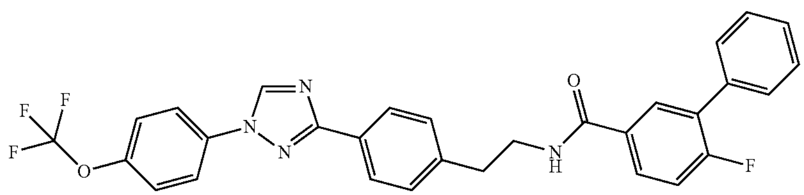 [SMILES: O=C(NCCc1ccc(-c2ncn(-c3ccc(OC(F)(F)F)cc3)n2)cc1)c1ccc(F)c(-c2ccccc2)c1] | White Solid | 18 |
| F52 | 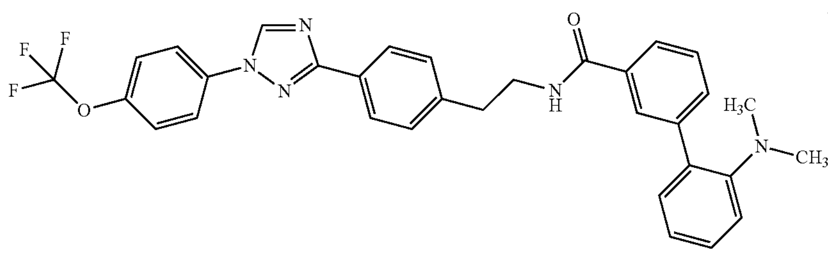 [SMILES: CN(C)c1ccccc1-c1cccc(C(=O)NCCc2ccc(-c3ncn(-c4ccc(OC(F)(F)F)cc4)n3)cc2)c1] | White Solid | 18 |
| F53 | 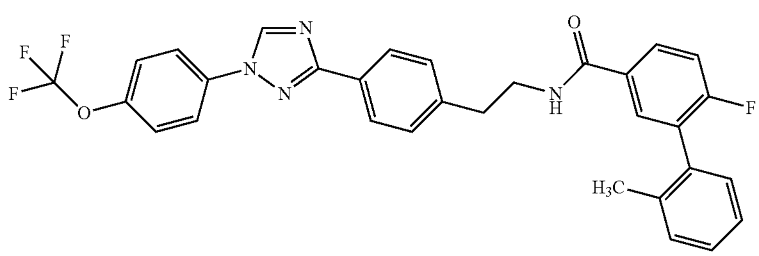 [SMILES: Cc1ccccc1-c1cc(C(=O)NCCc2ccc(-c3ncn(-c4ccc(OC(F)(F)F)cc4)n3)cc2)ccc1F] | White Solid | 18 |
| F54 | 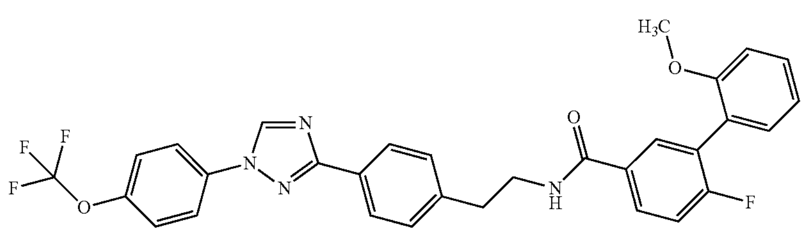 [SMILES: COc1ccccc1-c1cc(C(=O)NCCc2ccc(-c3ncn(-c4ccc(OC(F)(F)F)cc4)n3)cc2)ccc1F] | Colorless oil | 18 |

TABLE 3-continued

Structures for Molecules of Formula One

| No. | Structure | App. | Prepared according to Example: |
|---|---|---|---|
| F55 | 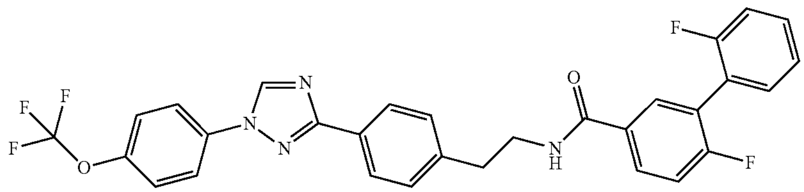 [SMILES: O=C(NCCc1ccc(-c2ncn(-c3ccc(OC(F)(F)F)cc3)n2)cc1)c1ccc(F)c(-c2ccccc2F)c1] | White solid | 18 |
| F56 | 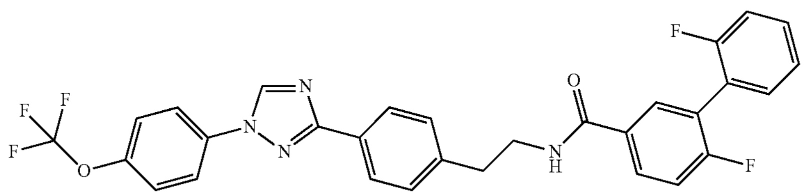 [SMILES: O=C(NCCc1ccc(-c2ncn(-c3ccc(OC(F)(F)F)cc3)n2)cc1)c1ccc(F)c(-c2ccccc2F)c1] | White solid | 18 |
| F57 | 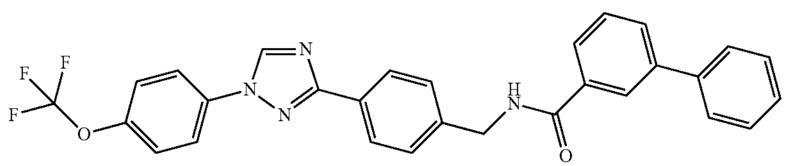 [SMILES: O=C(NCc1ccc(-c2ncn(-c3ccc(OC(F)(F)F)cc3)n2)cc1)c1cccc(-c2ccccc2)c1] | Off-white solid | 24 |
| F58 | 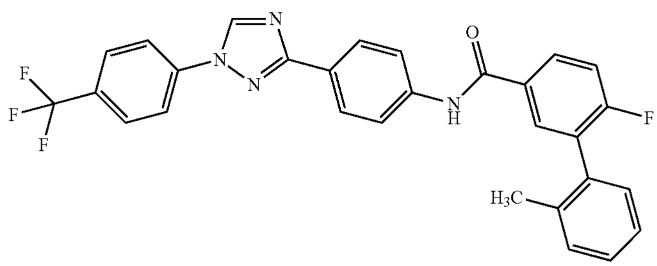 [SMILES: Cc1ccccc1-c1cc(C(=O)Nc2ccc(-c3ncn(-c4ccc(C(F)(F)F)cc4)n3)cc2)ccc1F] | White solid | 12 |
| F59 | 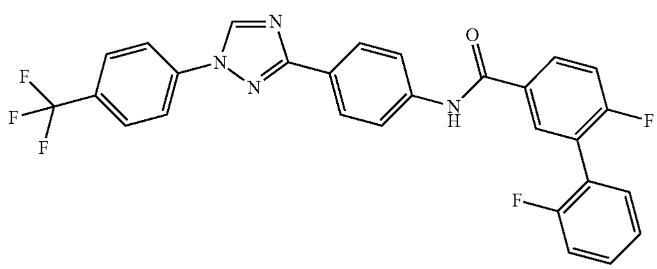 [SMILES: O=C(Nc1ccc(-c2ncn(-c3ccc(C(F)(F)F)cc3)n2)cc1)c1ccc(F)c(-c2ccccc2F)c1] | White solid | 12 |
| F60 | 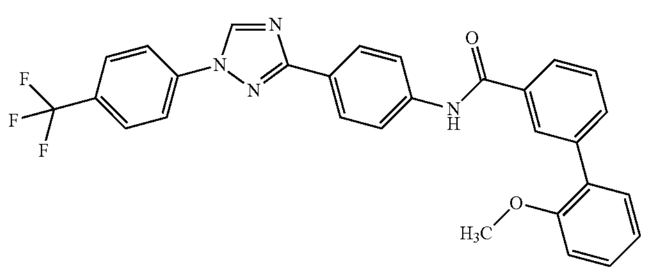 [SMILES: COc1ccccc1-c1cccc(C(=O)Nc2ccc(-c3ncn(-c4ccc(C(F)(F)F)cc4)n3)cc2)c1] | Off-white solid | 12 |

TABLE 3-continued

Structures for Molecules of Formula One

| No. | Structure | App. | Prepared according to Example: |
|---|---|---|---|
| F61 | 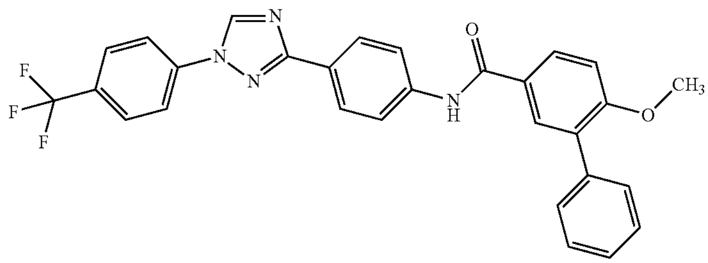 [SMILES: COc1ccc(C(=O)Nc2ccc(-c3ncn(-c4ccc(C(F)(F)F)cc4)n3)cc2)cc1-c1ccccc1] | White solid | 12 |
| F62 | 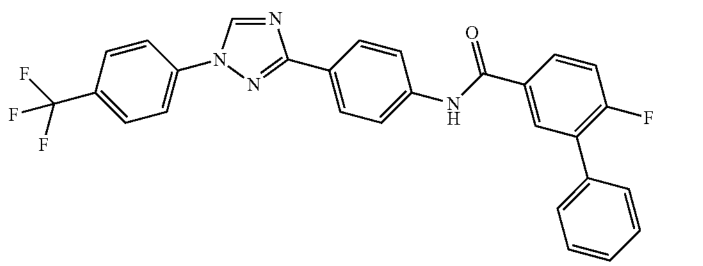 [SMILES: O=C(Nc1ccc(-c2ncn(-c3ccc(C(F)(F)F)cc3)n2)cc1)c1ccc(F)c(-c2ccccc2)c1] | White solid | 12 |
| F64 | 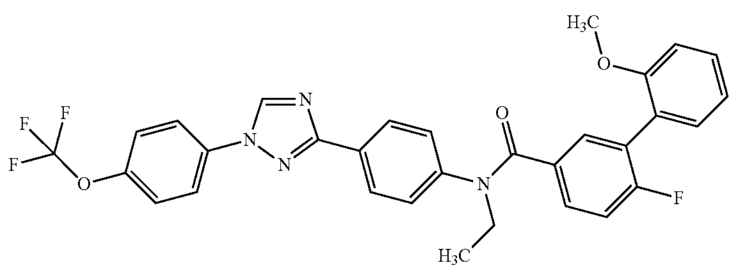 [SMILES: CCN(C(=O)c1ccc(F)c(-c2ccccc2OC)c1)c1ccc(-c2ncn(-c3ccc(OC(F)(F)F)cc3)n2)cc1] | Colorless oil | 5 |
| F65 | 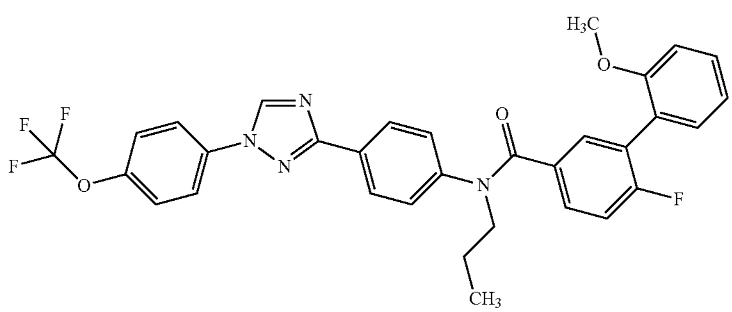 [SMILES: CCCN(C(=O)c1ccc(F)c(-c2ccccc2OC)c1)c1ccc(-c2ncn(-c3ccc(OC(F)(F)F)cc3)n2)cc1] | Colorless oil | 5 |
| F66 | 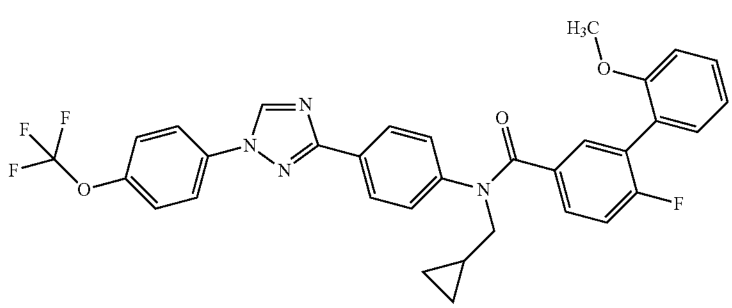 [SMILES: COc1ccccc1-c1cc(C(=O)N(CC2CC2)c2ccc(-c3ncn(-c4ccc(OC(F)(F)F)cc4)n3)cc2)ccc1F] | Colorless oil | 5 |

TABLE 3-continued

Structures for Molecules of Formula One

| No. | Structure | App. | Prepared according to Example: |
|---|---|---|---|
| F67 | 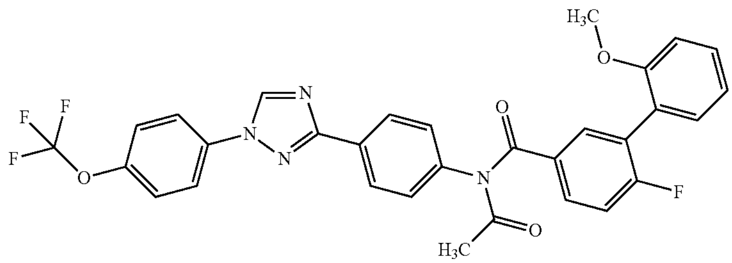 [SMILES: COc1ccccc1-c1cc(C(=O)N(C(C)=O)c2ccc(-c3ncn(-c4ccc(OC(F)(F)F)cc4)n3)cc2)ccc1F] | Colorless oil | 5 |
| F68 | 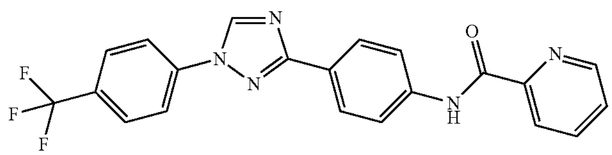 [SMILES: O=C(Nc1ccc(-c2ncn(-c3ccc(C(F)(F)F)cc3)n2)cc1)c1ccccn1] | White solid | 12 |

TABLE 4

Analytical Data for Compounds in Table 3.

| No. | Mp (° C.) | IR (cm$^{-1}$) | Mass (m/z) | $^1$H NMR | $^{13}$CNMR; $^{19}$F NMR |
|---|---|---|---|---|---|
| F1 | 162-169 | IR (thin film) 3251, 3060, 1667, 1595, 1515 cm$^{-1}$ | HRMS-FAB (m/z) calcd for C$_{29}$H$_{18}$F$_6$N$_4$O$_3$, 584.1283; found, 584.1287. | $^1$H NMR (400 MHz, DMSO-d$_6$) δ 10.53 (s, 1H), 9.40 (s, 1H), 8.14-8.03 (m, 6H), 8.00-7.95 (m, 2H), 7.73 (dt, J = 7.7, 1.5 Hz, 1H), 7.70-7.53 (m, 7H). | $^{13}$C NMR (101 MHz, DMSO-d$_6$) δ 165.13, 161.82, 146.98, 145.20, 143.64, 140.35, 136.21, 135.65, 134.92, 133.85, 132.12, 131.69, 129.77, 128.53, 128.13, 128.03, 127.24, 126.53, 125.42, 122.50, 121.56, 120.99, 120.31; $^{19}$F NMR (376 MHz, DMSO-d$_6$) δ −56.15, −56.98. |
| F2 | 152-156 | IR (thin film) 3530, 3131, 2917, 1690, 1614, 1588, 1517 cm$^{-1}$ | HRMS-FAB (m/z) calcd for C$_{29}$H$_{22}$F$_3$N$_5$O$_2$, 529.1726; found, 529.1728. | $^1$H NMR (400 MHz, CDCl$_3$) δ 10.22 (s, 1H), 8.56 (s, 1H), 8.27 (dd, J = 7.7, 1.0 Hz, 1H), 8.24-8.18 (m, 2H), 7.98 (t, J = 7.8 Hz, 1H), 7.93-7.85 (m, 2H), 7.84-7.77 (m, 2H), 7.61 (dd, J = 7.8, 1.0 Hz, 3H), 7.42-7.34 (m, 2H), 7.22-7.14 (m, 1H), 2.43 (s, 6H). | $^{13}$C NMR (101 MHz, CDCl$_3$) δ 163.16, 162.23, 158.59, 148.92, 148.35, 141.47, 139.09, 138.88, 138.01, 136.50, 135.78, 135.60, 131.86, 129.73, 127.46, 126.98, 126.90, 126.22, 122.39, 121.18, 120.20, 119.66, 21.20, 20.56. |
| F3 | 183-186 | IR (thin film) 3306, 3064, 1658, 1595, 1513 cm$^{-1}$ | HRMS-FAB (m/z) calcd for C$_{35}$H$_{25}$F$_3$N$_4$O$_3$, 606.1879; found, 606.1875. | $^1$H NMR (400 MHz, CDCl$_3$) δ 8.55 (s, 1H), 8.19-8.14 (m, 2H), 8.09 (t, J = 1.6 Hz, 1H), 7.90-7.86 (m, 1H), 7.82-7.73 (m, 4H), 7.63-7.59 (m, 2H), 7.54 (t, J = 7.7 Hz, 1H), 7.43-7.23 (m, 9H), 7.10 (ddt, J = 6.5, 3.3, 1.7 Hz, 2H), 5.11 (s, 2H). | $^{13}$C NMR (101 MHz, CDCl$_3$) δ 165.81, 163.09, 155.49, 148.34, 141.47, 139.32, 138.93, 136.94, 135.57, 134.48, 133.04, 130.83, 129.86, 129.31, 128.70, 128.64, 128.00, 127.94, 127.35, 126.97, 126.32, 126.07, 122.39, 121.57, 121.18, 119.94, 113.17, 70.46; $^{19}$F NMR (376 MHz, CDCl$_3$) δ −58.01. |
| F4 | 139-143 | IR (thin film) 3298, 3118, 2977, 2935, 2836, 2247, 1654, 1598, 1514 cm$^{-1}$ | HRMS-FAB (m/z) calcd for C$_{31}$H$_{27}$FN$_4$O$_3$, 522.2067; found, 522.2070. | $^1$H NMR (400 MHz, CDCl$_3$) δ 8.44 (s, 1H), 8.23-8.14 (m, 2H), 7.94 (s, 1H), 7.92-7.86 (m, 2H), 7.77-7.72 (m, 2H), 7.63-7.58 (m, 2H), 7.41 (ddd, J = 8.3, 7.5, 1.8 Hz, 1H), 7.29 (dd, J = 7.5, 1.3 Hz, 1H), 7.25-7.19 (m, 1H), 7.08-6.97 (m, 4H), 4.60 (p, J = 6.1 Hz, 1H), 3.82 (s, 3H), 1.37 (d, J = 6.0 Hz, 6H). | $^{13}$C NMR (101 MHz, CDCl$_3$) δ 164.72, 163.51, 162.45, 160.98, 157.69, 156.82, 141.40, 138.93, 131.17, 131.16, 131.00, 130.95, 130.75, 130.71, 130.29, 129.99, 128.45, 128.36, 127.33, 126.99, 126.97, 126.80, 123.79, 121.75, 120.66, 119.95, 116.65, 116.26, 116.02, 111.11, 70.44, 55.69, 21.93; $^{19}$F NMR (376 MHz, CDCl$_3$) δ −108.15. |
| F5 | 128-132 | IR (thin film) 3296, 3062, 2976, 2935, 2835, 2246, 1654, 1595, 1513 cm$^{-1}$ | HRMS-FAB (m/z) calcd for C$_{31}$H$_{28}$N$_4$O$_3$, 504.2161; found, 504.2156. | $^1$H NMR (400 MHz, CDCl$_3$) δ 8.44 (s, 1H), 8.23-8.17 (m, 2H), 8.03 (t, J = 1.6 Hz, 1H), 7.99 (s, 1H), 7.85 (ddd, J = 7.7, 1.8, 1.2 Hz, 1H), 7.80-7.75 (m, 2H), 7.75-7.69 (m, 1H), 7.64-7.58 (m, 2H), 7.53 (t, J = 7.7 Hz, 1H), 7.40-7.32 (m, 2H), 7.09-6.97 (m, | $^{13}$C NMR (101 MHz, CDCl$_3$) δ 165.79, 162.49, 157.67, 156.37, 141.40, 139.25, 139.08, 134.73, 133.10, 130.79, 130.30, 129.42, 129.27, 128.53, 128.06, 127.32, 126.88, 125.61, 121.75, 120.97, 119.89, 116.65, 111.25, 70.43, 55.60, 21.93. |

TABLE 4-continued

Analytical Data for Compounds in Table 3.

| No. | Mp (° C.) | IR (cm$^{-1}$) | Mass (m/z) | $^1$H NMR | $^{13}$CNMR; $^{19}$F NMR |
|---|---|---|---|---|---|
| | | | | 4H), 4.60 (p, J = 6.1 Hz, 1H), 3.83 (s, 3H), 1.37 (d, J = 6.1 Hz, 6H). | |
| F6 | 201-205 | IR (thin film) 3273, 3094, 2251, 2125, 1660, 1599, 1570, 1532, 1514 cm$^{-1}$ | HRMS-FAB (m/z) calcd for C$_{29}$H$_{18}$ClF$_5$N$_4$O$_2$, 584.1038; found, 584.1045. | $^1$H NMR (400 MHz, DMSO-d$_6$) δ 10.62 (s, 1H), 9.42 (s, 1H), 8.23 (t, J = 1.6 Hz, 1H), 8.16-8.06 (m, 4H), 8.04-7.93 (m, 4H), 7.83 (dd, J = 8.3, 1.2 Hz, 2H), 7.63 (d, J = 9.1 Hz, 2H), 7.57-7.51 (m, 2H), 7.50-7.44 (m, 1H). | $^{13}$C NMR (101 MHz, DMSO-d$_6$) δ 164.00, 161.79, 146.00, 143.66, 142.34, 140.13, 137.93, 137.12, 135.79, 133.90, 129.28, 129.03, 128.43, 127.02, 126.56, 126.33, 125.60, 124.64, 123.08, 120.98, 120.39; $^{19}$F NMR (376 MHz, DMSO-d6) δ −85.21, −86.93. |
| F7 | 179-186 | IR (thin film) 3255, 3069, 2838, 2251, 2124, 1667, 1599, 1534, 1513 cm$^{-1}$ | HRMS-FAB (m/z) calcd for C$_{30}$H$_{20}$F$_6$N$_4$O$_3$, 598.1440; found, 598.1428. | $^1$H NMR (400 MHz, DMSO-d$_6$) δ 10.45 (s, 1H), 9.41 (s, 1H), 8.14-8.01 (m, 6H), 7.98-7.93 (m, 2H), 7.62 (d, J = 9.1 Hz, 2H), 7.50-7.40 (m, 2H), 7.35 (dd, J = 7.5, 1.7 Hz, 1H), 7.20-7.15 (m, 1H), 7.10 (td, J = 7.4, 1.0 Hz, 1H), 3.78 (s, 3H). | $^{13}$C NMR (101 MHz, DMSO-d$_6$) δ 164.38, 162.65, 161.87, 160.14, 156.51, 146.04, 143.69, 140.43, 135.84, 131.48, 131.44, 130.91, 130.78, 130.75, 130.04, 129.49, 129.40, 126.56, 125.94, 125.77, 125.39, 123.51, 123.14, 121.03, 120.51, 120.31, 115.67, 115.44, 111.37, 55.51; $^{19}$F NMR (376 MHz, DMSO-d6) δ −85.21, −86.92, −109.18. |
| F8 | 173-176 | IR (thin film) 3294, 3060, 2968, 2932, 2873, 2246, 1654, 1593, 1514 cm$^{-1}$ | HRMS-FAB (m/z) calcd for C$_{30}$H$_{23}$F$_3$N$_4$O$_2$, 528.1773; found, 528.1782. | $^1$H NMR (400 MHz, CDCl$_3$) δ 8.55 (s, 1H), 8.23-8.17 (m, 2H), 8.00 (s, 1H), 7.89 (dt, J = 7.1, 1.8 Hz, 1H), 7.84-7.76 (m, 5H), 7.59-7.49 (m, 2H), 7.42-7.32 (m, 4H), 7.29-7.19 (m, 2H), 2.60 (q, J = 7.5 Hz, 2H), 1.11 (t, J = 7.5 Hz, 3H). | $^{13}$C NMR (101 MHz, CDCl$_3$) δ 165.57, 163.04, 148.33, 142.70, 141.56, 141.48, 140.35, 139.28, 135.56, 134.69, 132.80, 129.86, 128.75, 128.67, 128.07, 127.70, 127.48, 126.51, 125.76, 125.61, 122.39, 121.17, 119.98, 26.15, 15.62; $^{19}$F NMR (376 MHz, CDCl$_3$) δ −58.01. |
| F9 | 170-180 | IR (thin film) 3251, 3060, 2252, 2125, 1684, 1595, 1531, 1513 cm$^{-1}$ | HRMS-FAB (m/z) calcd for C$_{31}$H$_{21}$F$_5$N$_4$O$_3$, 592.1534; found, 592.1545. | $^1$H NMR (400 MHz, DMSO-d$_6$) δ 10.51 (s, 1H), 9.41 (s, 1H), 8.14-8.08 (m, 4H), 8.02 (dt, J = 7.7, 1.3 Hz, 1H), 8.00-7.95 (m, 3H), 7.74-7.71 (m, 1H), 7.69-7.49 (m, 7H), 2.27 (s, 3H). | $^{13}$C NMR (101 MHz, DMSO-d$_6$) δ 202.71, 165.15, 161.84, 146.01, 143.65, 140.62, 140.38, 139.94, 139.22, 135.80, 134.84, 131.85, 130.98, 130.58, 128.56, 128.01, 127.77, 127.60, 126.87, 126.52, 125.39, 123.08, 120.99, 120.32, 30.17; $^{19}$F NMR (376 MHz, DMSO-d6) δ −85.21, −86.93. |
| F10 | | IR (thin film) 3298, 3062, 2941, 2831, 2782, 2245, 1655, 1593, 1514 cm$^{-1}$ | HRMS-FAB (m/z) calcd for C$_{30}$H$_{24}$F$_3$N$_5$O$_2$, 543.1882; found, 543.1893. | $^1$H NMR (400 MHz, CDCl$_3$) δ 8.55 (s, 1H), 8.23-8.18 (m, 2H), 8.10 (t, J = 1.6 Hz, 1H), 8.02 (s, 1H), 7.86-7.77 (m, 6H), 7.53 (t, J = 7.7 Hz, 1H), 7.38 (d, J = 8.3 Hz, 2H), 7.31 (ddd, J = 8.1, 7.4, 1.7 Hz, 1H), 7.25 (d, J = 7.5 Hz, 1H), 7.10-7.01 (m, 2H), 2.55 (s, 6H). | $^{13}$C NMR (101 MHz, CDCl$_3$) δ 165.83, 163.06, 151.29, 148.32, 142.65, 141.48, 139.41, 135.57, 134.95, 132.89, 132.32, 131.57, 128.97, 128.71, 127.46, 127.02, 126.40, 125.42, 122.38, 121.77, 121.17, 119.93, 117.86, 43.49; $^{19}$F NMR(376 MHz, CDCl$_3$) δ −58.01. |
| F11 | 166-170 | IR (thin film) 3316, 3106, 1651, 1593, 1514 cm$^{-1}$ | HRMS-FAB (m/z) calcd for C$_{28}$H$_{25}$F$_3$N$_4$O$_4$, 538.1828; found, 538.1833. | $^1$H NMR (400 MHz, DMSO-d$_6$) δ 10.52 (s, 1H), 9.40 (s, 1H), 8.19 (dd, J = 7.5, 2.4 Hz, 1H), 8.16-8.01 (m, 5H), 8.00-7.92 (m, 2H), 7.72-7.59 (m, 4H), 7.59-7.44 (m, 4H). | $^{13}$C NMR (101 MHz, CDCl$_3$) δ 164.41, 162.02, 161.91, 159.70, 147.09, 143.73, 140.41, 135.74, 134.43, 131.50, 130.49, 129.53, 128.98, 128.74, 128.28, 128.08, 126.62, 125.51, 122.59, 121.33, 121.08, 120.41, 118.78, 116.57, 116.34; $^{19}$F NMR (376 MHz, DMSO-d6) δ −56.97, −113.91. |
| F12 | 180-192 | IR (thin film) 3290, 3061, 2246, 1652, 1593, 1513 cm$^{-1}$ | HRMS-FAB (m/z) calcd for C$_{30}$H$_{23}$F$_3$N$_4$O$_2$, 528.1773; found, 528.1796. | $^1$H NMR (400 MHz, CDCl$_3$) δ 8.56 (s, 1H), 8.23-8.17 (m, 2H), 7.98 (s, 1H), 7.91 (ddd, J = 7.8, 1.8, 1.2 Hz, 1H), 7.83-7.76 (m, 4H), 7.68 (t, J = 1.6 Hz, 1H), 7.58 (t, J = 7.7 Hz, 1H), 7.41-7.35 (m, 3H), 7.21 (dd, J = 8.5, 6.4 Hz, 1H), 7.16-7.11 (m, 2H), 2.05 (s, 6H). | $^{13}$C NMR (101 MHz, CDCl$_3$) δ 165.47, 163.05, 148.37, 141.88, 141.49, 140.52, 139.28, 135.93, 135.57, 135.00, 132.87, 129.19, 127.58, 126.50, 125.68, 122.40, 121.18, 119.99, 115.80, 20.91. |
| F13 | 188-197 | IR (thin film) 3394, 3262, 3104, 1657, 1598, 1514 cm$^{-1}$ | HRMS-FAB (m/z) calcd for C$_{30}$H$_{21}$F$_5$N$_4$O$_3$, 580.1534; found, 580.1545. | $^1$H NMR (400 MHz, DMSO-d$_6$) δ 10.35 (s, 1H), 9.41 (s, 1H), 8.13-8.03 (m, 4H), 8.01 (d, J = 2.4 Hz, 1H), 7.99-7.94 (m, 2H), 7.65-7.55 (m, 4H), 7.51-7.31 (m, 4H), 7.28 (d, J = 8.8 Hz, 1H), 3.87 (s, 3H). | $^{13}$C NMR (101 MHz, DMSO-d$_6$) δ 164.85, 161.94, 158.79, 146.04, 143.65, 140.69, 137.48, 135.85, 129.94, 129.53, 129.38, 129.35, 129.22, 129.16, 128.21, 128.05, 127.17, 126.80, 126.52, 125.15, 123.11, 121.01, 120.27, 111.21, 55.85; $^{19}$F NMR (376 MHz, DMSO-d$_6$) δ −85.22, −86.93. |
| F14 | 178-187 | IR (thin film) 3268, 3112, 3060, 1670, 1652, 1613, 1589, 1511 cm$^{-1}$ | HRMS-FAB (m/z) calcd for C$_{29}$H$_{21}$F$_3$N$_4$O$_2$, 514.1617; found, 514.1637. | $^1$H NMR (400 MHz, DMSO-d$_6$) δ 10.64 (s, 1H), 9.39 (s, 1H), 8.09 (dd, J = 9.0, 6.9 Hz, 4H), 7.92 (d, J = 8.7 Hz, 2H), 7.62 (d, J = 8.3 Hz, 2H), 7.49 (dd, J = 7.9, 6.6 Hz, 3H), 7.45-7.30 (m, 5H), 2.26 (s, 3H). | $^{13}$C NMR (101 MHz, CDCl$_3$) δ 168.35, 161.91, 147.05, 143.72, 142.41, 140.88, 140.55, 138.56, 135.73, 131.92, 130.78, 129.06, 128.36, 127.21, 126.71, 126.18, 125.74, 125.37, 122.58, 121.11, 119.62, 17.27. |

TABLE 4-continued

Analytical Data for Compounds in Table 3.

| No. | Mp (° C.) | IR (cm$^{-1}$) | Mass (m/z) | $^1$H NMR | $^{13}$C NMR; $^{19}$F NMR |
|---|---|---|---|---|---|
| F15 | >200 (dec.) | IR (thin film) 3234, 3031, 1675, 1599, 1543, 1516 cm$^{-1}$ | HRMS-FAB (m/z) calcd for C$_{28}$H$_{18}$ClF$_3$N$_4$O$_2$, 534.1070; found, 534.1084. | $^1$H NMR (400 MHz, CDCl$_3$) δ 8.59 (s, 1H), 8.23 (d, J = 8.6 Hz, 2H), 8.17 (s, 1H), 7.93 (d, J = 8.0 Hz, 1H), 7.84-7.78 (m, 4H), 7.70 (d, J = 1.6 Hz, 1H), 7.62 (td, J = 6.9, 6.3, 3.2 Hz, 3H), 7.52-7.37 (m, 5H). | $^{13}$C NMR (101 MHz, DMSO-d$_6$) δ 164.87, 161.83, 147.03, 143.72, 143.06, 140.20, 137.92, 135.70, 135.44, 130.69, 129.52, 129.12, 128.48, 127.54, 126.95, 126.75, 125.58, 125.43, 122.56, 121.10, 119.62. |
| F16 | 183-186 | IR (thin film) 3252, 3058, 2976, 2932, 2252, 1666, 1599, 1535, 1514 cm$^{-1}$ | HRMS-FAB (m/z) calcd for C$_{30}$H$_{25}$FN$_4$O$_2$, 492.1962; found492.1964. | $^1$H NMR (400 MHz, DMSO-d$_6$) δ 10.50 (s, 1H), 9.21 (s, 1H), 8.19 (dd, J = 7.5, 2.4 Hz, 1H), 8.13-8.02 (m, 3H), 7.97-7.92 (m, 2H), 7.84-7.78 (m, 2H), 7.70-7.65 (m, 2H), 7.58-7.44 (m, 4H), 7.14-7.08 (m, 2H), 4.70 (p, J = 6.0 Hz, 1H), 1.30 (d, J = 6.0 Hz, 6H). | $^{13}$C NMR (101 MHz, DMSO-d$_6$) δ 164.33, 162.15, 161.34, 159.64, 156.78, 142.89, 140.10, 134.40, 131.48, 131.45, 130.48, 130.44, 129.95, 129.58, 129.48, 128.94, 128.91, 128.70, 128.24, 128.16, 128.02, 126.40, 125.89, 121.00, 120.35, 116.53, 116.32, 69.61, 21.71; $^{19}$F NMR (376 MHz, DMSO-d$_6$) δ −113.94 |
| F17 | 164-168 | IR (thin film) 3296, 3061, 2246, 1654, 1593, 1515 cm$^{-1}$ | HRMS-FAB (m/z) calcd for C$_{29}$H$_{21}$F$_3$N$_4$O$_2$, 514.1617; found, 514.1630. | $^1$H NMR (400 MHz, CDCl$_3$) δ 8.55 (s, 1H), 8.23-8.17 (m, 2H), 8.06-8.00 (m, 2H), 7.84 (ddd, J = 7.7, 1.8, 1.2 Hz, 1H), 7.82-7.76 (m, 4H), 7.72 (dt, J = 7.7, 1.2 Hz, 1H), 7.52 (t, J = 7.7 Hz, 1H), 7.41-7.32 (m, 4H), 7.09-6.98 (m, 2H), 3.83 (s, 3H). | $^{13}$C NMR (101 MHz, CDCl$_3$) δ 165.60, 163.05, 148.36, 142.71, 141.49, 140.68, 139.29, 135.57, 135.31, 134.80, 132.78, 130.50, 129.69, 128.70, 127.85, 127.69, 127.49, 126.52, 125.97, 125.58, 122.39, 121.67, 121.18, 119.99, 119.11, 20.43. |
| F18 | 182-201 | IR (thin film) 3318, 3103, 2918, 2849, 1690, 1615, 1590, 1570, 1532, 1517 cm$^{-1}$ | HRMS-FAB (m/z) calcd for C$_{27}$H$_{16}$Cl$_2$F$_3$N$_5$O$_2$, 569.0633; found, 569.0634. | $^1$H NMR (400 MHz, CDCl$_3$) δ 10.15 (s, 1H), 8.57 (s, 1H), 8.34 (dd, J = 7.8, 1.0 Hz, 1H), 8.25-8.18 (m, 2H), 8.02 (t, J = 7.8 Hz, 1H), 7.94-7.87 (m, 2H), 7.84-7.77 (m, 3H), 7.62-7.56 (m, 2H), 7.48-7.36 (m, 3H). | $^{13}$C NMR (101 MHz, CDCl$_3$) δ 163.13, 161.77, 154.45, 149.48, 148.35, 141.49, 138.96, 138.05, 136.56, 135.56, 133.19, 132.30, 130.26, 127.58, 127.48, 126.36, 122.39, 121.41, 121.20, 119.71. |
| F19 | | | ESIMS m/z 545 ([M + H]$^+$) | $^1$H NMR (400 MHz, CDCl$_3$) δ 8.55 (s, 1H), 8.11-8.06 (m, 2H), 7.80-7.74 (m, 2H), 7.54 (t, J = 1.5 Hz, 1H), 7.44 (dt, J = 7.6, 1.5 Hz, 1H), 7.41-7.36 (m, 2H), 7.31-7.17 (m, 5H), 7.03 (dd, J = 7.8, 1.8 Hz, 1H), 6.92 (ddd, J = 8.5, 5.9, 1.2 Hz, 2H), 3.71 (s, 3H), 3.56 (s, 3H). | $^{13}$C NMR (151 MHz, CDCl$_3$) δ 162.64, 156.35, 148.37, 146.24, 141.58, 138.24, 135.43, 131.03, 130.78, 129.93, 129.74, 128.79, 128.26, 127.43, 127.38, 127.16, 126.99, 122.92, 122.37, 121.21, 121.10, 120.74, 119.49, 117.78, 111.24, 55.51, 38.32; $^{19}$F NMR (376 MHz, CDCl$_3$) δ −58.03. |
| F20 | >220 (dec.) | IR (thin film) 3252, 3067, 2838, 2250, 2125, 1667, 1615, 1599, 1524 cm$^{-1}$ | HRMS-FAB (m/z) calcd for C$_{29}$H$_{20}$F$_4$N$_4$O$_2$, 532.1522; found, 532.1537. | $^1$H NMR (400 MHz, DMSO-d$_6$) δ 10.46 (s, 1H), 9.52 (s, 1H), 8.20 (d, J = 8.4 Hz, 2H), 8.15-8.10 (m, 2H), 8.05 (ddt, J = 9.1, 7.1, 2.3 Hz, 2H), 8.01-7.94 (m, 4H), 7.50-7.40 (m, 2H), 7.35 (dd, J = 7.5, 1.7 Hz, 1H), 7.20-7.15 (m, 1H), 7.10 (td, J = 7.4, 1.0 Hz, 1H), 3.78 (s, 3H). | $^{13}$C NMR (101 MHz, DMSO-d$_6$) δ 164.40, 162.65, 162.05, 160.15, 156.51, 144.02, 140.55, 139.59, 131.49, 131.44, 130.91, 130.77, 130.74, 130.05, 129.50, 129.41, 127.71, 127.39, 127.10, 127.06, 126.66, 125.94, 125.78, 125.27, 125.22, 123.51, 122.57, 120.51, 120.32, 119.44, 115.68, 115.45, 111.38, 55.52; $^{19}$F NMR (376 MHz, DMSO-d6) δ −60.80, −109.15. |
| F21 | 138-148 | IR (thin film) 2959, 2836, 1596, 1515 cm$^{-1}$ | HRMS-FAB (m/z) calcd for C$_{29}$H$_{21}$F$_3$N$_4$O$_2$S, 546.1337; found, 546.1334. | $^1$H NMR (400 MHz, CDCl$_3$) δ 9.21 (s, 1H), 8.74 (s, 1H), 8.22 (d, J = 7.7 Hz, 2H), 7.95 (d, J = 10.0 Hz, 3H), 7.79 (d, J = 9.0 Hz, 3H), 7.67 (d, J = 7.4 Hz, 1H), 7.47 (t, J = 7.6 Hz, 1H), 7.36 (dd, J = 16.8, 8.0 Hz, 3H), 7.08-6.91 (m, 3H), 3.83 (d, J = 3.6 Hz, 3H). | $^{13}$C NMR (101 MHz, CDCl$_3$) δ 161.99, 156.37, 148.57, 141.80, 140.48, 139.07, 135.24, 132.73, 132.57, 130.82, 129.42, 129.25, 128.34, 127.84, 127.40, 125.65, 123.30, 122.40, 121.64, 121.30, 120.98, 111.24, 55.61; $^{19}$F NMR (376 MHz, CDCl$_3$) δ −57.99. |
| F22 | 63-67 | IR (thin film) 3290, 3063, 2938, 2835, 2246, 1655, 1593, 1513 cm$^{-1}$ | HRMS-FAB (m/z) calcd for C$_{29}$H$_{21}$F$_3$N$_4$O$_3$, 530.1566; found, 530.1573. | $^1$H NMR (400 MHz, CDCl$_3$) δ 8.55 (s, 1H), 8.23-8.17 (m, 2H), 8.06-8.00 (m, 2H), 7.84 (ddd, J = 7.7, 1.8, 1.2 Hz, 1H), 7.82-7.76 (m, 4H), 7.72 (dt, J = 7.7, 1.2 Hz, 1H), 7.52 (t, J = 7.7 Hz, | $^{13}$C NMR (101 MHz, CDCl$_3$) δ 165.85, 163.07, 156.39, 148.32, 141.48, 141.48, 139.41, 134.68, 133.15, 130.79, 129.43, 129.30, 128.54, 128.08, 127.46, 126.41, 125.62, 122.38, 121.67, 121.17, 120.99, 119.97, 119.11, 111.29, 55.61. |

TABLE 4-continued

Analytical Data for Compounds in Table 3.

| No. | Mp (° C.) | IR (cm$^{-1}$) | Mass (m/z) | $^1$H NMR | $^{13}$CNMR; $^{19}$F NMR |
|---|---|---|---|---|---|
| | | | | 1H), 7.41-7.32 (m, 4H), 7.09-6.98 (m, 2H), 3.83 (s, 3H). | |
| F23 | 145-154 | IR (thin film) 2940, 2836, 1596, 1513 cm$^{-1}$ | HRMS-FAB (m/z) calcd for C$_{30}$H$_{21}$F$_5$N$_4$O$_2$S, 596.1305; found, 596.1308. | $^1$H NMR (400 MHz, CDCl$_3$) δ 9.19 (s, 1H), 8.69 (s, 1H), 8.24 (d, J = 7.7 Hz, 2H), 8.03-7.87 (m, 3H), 7.68 (d, J = 7.5 Hz, 3H), 7.48 (t, J = 7.6 Hz, 1H), 7.37 (dd, J = 21.0, 8.3 Hz, 4H), 7.09-6.91 (m, 3H), 3.84 (s, 3H). | $^{13}$C NMR (101 MHz, CDCl$_3$) δ 162.32, 156.38, 147.70, 141.80, 140.42, 139.09, 135.51, 132.73, 132.60, 130.82, 129.43, 129.26, 128.36, 127.38, 125.63, 123.28, 123.10, 121.25, 120.98, 113.77, 113.61, 111.25, 55.62; $^{19}$F NMR (376 MHz, CDCl$_3$) δ −85.88, −87.84. |
| F24 | 180-183 | IR (thin film) 3293, 3061, 1655, 1593, 1515 cm$^{-1}$ | HRMS-FAB (m/z) calcd for C$_{28}$H$_{19}$F$_3$N$_4$O$_2$, 500.1460; found, 500.1469. | $^1$H NMR (400 MHz, CDCl$_3$) δ 8.56 (s, 1H), 8.22 (d, J = 8.7 Hz, 2H), 8.10 (t, J = 1.7 Hz, 1H), 8.03 (s, 1H), 7.87-7.75 (m, 6H), 7.66-7.60 (m, 2H), 7.57 (t, J = 7.7 Hz, 1H), 7.48 (t, J = 7.5 Hz, 2H), 7.40 (t, J = 8.0 Hz, 3H). | $^{13}$C NMR (101 MHz, CDCl$_3$) δ 165.68, 163.05, 148.34, 142.05, 141.49, 140.02, 139.27, 135.56, 135.43, 130.67, 129.31, 128.97, 127.92, 127.49, 127.21, 126.55, 125.92, 125.67, 122.39, 121.18, 120.03, 119.11; $^{19}$F NMR (376 MHz, CDCl$_3$) δ −58.01. |
| F25 | 180-189 | IR (thin film) 3306, 3114, 1648, 1592, 1544, 1515 cm$^{-1}$ | HRMS-FAB (m/z) calcd for C$_{28}$H$_{18}$F$_4$N$_4$O$_2$, 518.1366; found, 518.1383. | $^1$H NMR (400 MHz, CDCl$_3$) δ 8.57 (s, 1H), 8.25-8.19 (m, 2H), 8.01 (s, 1H), 7.86 (t, J = 1.5 Hz, 1H), 7.83-7.76 (m, 4H), 7.64-7.58 (m, 2H), 7.56 (ddd, J = 8.7, 2.3, 1.6 Hz, 1H), 7.52-7.36 (m, 6H). | $^{13}$C NMR (101 MHz, CDCl$_3$) δ 164.45, 162.94, 161.91, 148.41, 144.31, 141.53, 138.95, 138.84, 137.45, 137.37, 135.53, 129.11, 129.04, 128.52, 127.52, 127.15, 126.79, 122.40, 121.67, 121.37, 121.19, 120.15, 119.10, 117.62, 117.40, 113.10, 112.87; $^{19}$F NMR (376 MHz, CDCl$_3$) δ −58.01, −111.14. |
| F26 | 150-154 | IR (thin film) 3251, 3065, 2836, 2250, 2124, 1667, 1596, 1531, 1513 cm$^{-1}$ | HRMS-FAB (m/z) calcd for C$_{30}$H$_{21}$F$_5$N$_4$O$_3$, 580.1534; found, 580.1541. | $^1$H NMR (400 MHz, DMSO-d$_6$) δ 10.48 (s, 1H), 9.41 (s, 1H), 8.15-8.05 (m, 5H), 8.01-7.90 (m, 3H), 7.72 (dt, J = 7.7, 1.2 Hz, 1H), 7.66-7.54 (m, 3H), 7.45-7.36 (m, 2H), 7.17 (dd, J = 8.8, 0.9 Hz, 1H), 7.09 (td, J = 7.5, 1.0 Hz, 1H), 3.80 (s, 3H). | $^{13}$C NMR (101 MHz, CDCl$_3$) δ 165.66, 161.92, 156.11, 146.07, 143.70, 140.55, 138.30, 135.87, 134.67, 132.56, 130.49, 129.30, 129.02, 128.39, 128.07, 126.57, 126.26, 125.36, 123.14, 121.05, 120.82, 120.30, 111.76, 55.53; $^{19}$F NMR (376 MHz, DMSO-d6) δ −85.21, −86.92. |
| F27 | 199-204 | IR (thin film) 3307, 3105, 1678, 1589, 1538, 1516 cm$^{-1}$ | HRMS-FAB (m/z) calcd for C$_{27}$H$_{18}$F$_3$N$_5$O$_2$, 501.1413; found, 501.1427. | $^1$H NMR (400 MHz, CDCl$_3$) δ 10.29 (s, 1H), 8.57 (s, 1H), 8.26 (ddd, J = 14.8, 7.2, 1.5 Hz, 3H), 8.10-7.90 (m, 6H), 7.85-7.77 (m, 2H), 7.62-7.47 (m, 3H), 7.43-7.36 (m, 2H). | $^{13}$C NMR (101 MHz, CDCl$_3$) δ 163.15, 162.15, 156.11, 149.45, 148.32, 141.48, 139.03, 138.63, 138.18, 135.59, 129.68, 129.01, 127.50, 127.02, 126.31, 123.54, 122.40, 121.20, 120.87, 119.72. |
| F28 | 175-182 | IR (thin film) 3294, 3117, 1655, 1595, 1515 cm$^{-1}$ | HRMS-FAB (m/z) calcd for C$_{28}$H$_{17}$F$_5$N$_4$O$_2$, 536.1272; found, 536.1273. | $^1$H NMR (400 MHz, CDCl$_3$) δ 8.55 (s, 1H), 8.23-8.16 (m, 2H), 7.99 (s, 1H), 7.92 (dd, J = 7.3, 5.2 Hz, 2H), 7.83-7.73 (m, 4H), 7.46-7.35 (m, 4H), 7.31-7.15 (m, 3H). | $^{13}$C NMR (101 MHz, CDCl$_3$) δ 164.49, 163.26, 162.98, 161.00, 160.72, 158.52, 148.38, 141.49, 139.09, 135.53, 131.46, 131.09, 131.05, 130.86, 130.85, 130.82, 130.50, 130.42, 129.06, 128.97, 127.48, 126.66, 124.35, 124.32, 124.15, 122.39, 122.28, 121.17, 120.11, 119.10, 116.59, 116.36, 116.03, 115.81; $^{19}$F NMR (376 MHz, CDCl$_3$) δ −58.02, −108.64, −114.62. |
| F29 | | IR (thin film) 1514, 1609, 1644, 3065 cm$^{-1}$ | HRMS-FAB (m/z) calcd for C$_{31}$H$_{22}$F$_6$N$_4$O$_2$, 596.1647; found, 596.1653. | $^1$H NMR (400 MHz, CDCl$_3$) δ 8.57 (s, 1H), 8.14-8.07 (m, 2H), 7.84-7.77 (m, 2H), 7.40 (d, J = 9.0 Hz, 2H), 7.24-7.08 (m, 6H), 6.99 (t, J = 1.4 Hz, 1H), 6.91 (dd, J = 7.9, 1.2 Hz, 2H), 3.55 (s, 3H), 1.94 (s, 3H). | $^{13}$C NMR (101 MHz, CDCl$_3$) δ 169.29, 163.17, 162.51, 160.71, 147.64, 145.72, 143.75, 143.68, 141.63, 139.71, 137.64, 137.56, 135.58, 135.09, 130.26, 129.46, 128.77, 127.84, 127.60, 127.01, 125.78, 125.36, 123.12, 123.01, 121.16, 120.98, 117.72, 117.51, 114.33, 114.10, 112.14, 38.25, 19.91; $^{19}$F NMR (376 MHz, CDCl$_3$) δ −85.89, −87.86, −112.79. |
| F30 | 171-179 | IR (thin film) 3306, 3118, 1642, 1592, 1515 cm$^{-1}$ | HRMS-FAB (m/z) calcd for C$_{28}$H$_{18}$ClF$_3$N$_4$O$_2$, 534.1070; found, 534.1085. | $^1$H NMR (400 MHz, CDCl$_3$) δ 8.56 (s, 1H), 8.24-8.17 (m, 2H), 8.02 (s, 1H), 7.96-7.89 (m, 2H), 7.83-7.76 (m, 4H), 7.66 (dt, J = 7.7, 1.3 Hz, 1H), 7.57 (t, J = 7.7 Hz, 1H), 7.52-7.48 (m, 1H), 7.42-7.30 (m, 5H). | $^{13}$C NMR (101 MHz, CDCl$_3$) δ 165.47, 163.04, 148.36, 141.49, 140.08, 139.32, 139.25, 135.57, 134.83, 133.06, 132.43, 131.28, 130.09, 129.15, 128.67, 128.02, 127.49, 127.06, 126.55, 126.35, 122.39, 121.18, 120.05. |
| F31 | 102-110 | IR (thin film) 3251, 3062, | HRMS-FAB (m/z) calcd for C$_{31}$H$_{23}$F$_5$N$_4$O$_2$, 578.1741; found, 578.1749. | $^1$H NMR (400 MHz, DMSO-d$_6$) δ 10.42 (s, 1H), 9.41 (s, 1H), 8.13-8.07 (m, 4H), 8.03 (dt, | $^{13}$C NMR (101 MHz, DMSO-d$_6$) δ 165.13, 161.85, 146.00, 143.64, 140.56, 140.47, 140.40, 135.80, 135.21, 134.67, 132.19, 128.74, 127.75, |

TABLE 4-continued

Analytical Data for Compounds in Table 3.

| No. | Mp (° C.) | IR (cm$^{-1}$) | Mass (m/z) | $^1$H NMR | $^{13}$CNMR; $^{19}$F NMR |
|---|---|---|---|---|---|
| | | 2250, 2124, 1667, 1596, 1532, 1513 cm$^{-1}$ | | J = 7.8, 1.2 Hz, 1H), 7.99 (d, J = 1.9 Hz, 1H), 7.97 (d, J = 1.9 Hz, 1H), 7.85 (t, J = 1.5 Hz, 1H), 7.70-7.58 (m, 3H), 7.40 (dt, J = 7.5, 1.4 Hz, 1H), 7.26-7.13 (m, 3H), 2.02 (s, 6H). | 127.27, 126.48, 126.44, 125.34, 123.08, 120.97, 120.37, 20.51; $^{19}$F NMR (376 MHz, DMSO-d6) δ −85.22, −86.94. |
| F32 | 202-204 | IR (thin film) 3295, 3116, 3062, 2246, 1653, 1596, 1567, 1513 cm$^{-1}$ | HRMS-FAB (m/z) calcd for C$_{29}$H$_{20}$ClF$_3$N$_4$O$_2$, 548.1227; found, 548.1234. | $^1$H NMR (400 MHz, CDCl$_3$) δ 8.55 (s, 1H), 8.22-8.17 (m, 2H), 7.95 (s, 1H), 7.87 (dd, J = 8.3, 2.3 Hz, 1H), 7.82-7.73 (m, 5H), 7.61 (d, J = 8.3 Hz, 1H), 7.42-7.25 (m, 5H), 7.17 (dd, J = 7.4, 1.2 Hz, 1H), 2.15 (s, 3H). | $^{13}$C NMR (101 MHz, CDCl$_3$) δ 164.47, 162.98, 148.37, 141.49, 141.25, 139.01, 138.24, 137.59, 136.17, 135.54, 133.21, 130.06, 129.38, 129.27, 128.45, 127.49, 126.70, 125.75, 122.40, 121.66, 121.17, 120.06, 119.10, 19.79. |
| F33 | 170-180 | IR (thin film) 3343, 3124, 1686, 1616, 1589, 1546, 1517 cm$^{-1}$ | HRMS-FAB (m/z) calcd for C$_{28}$H$_{20}$F$_3$N$_5$O$_2$, 515.1569; found, 515.1567. | $^1$H NMR (400 MHz, CDCl$_3$) δ 10.20 (s, 1H), 8.56 (s, 1H), 8.30 (dd, J = 7.7, 1.0 Hz, 1H), 8.24-8.17 (m, 2H), 8.00 (t, J = 7.8 Hz, 1H), 7.92-7.86 (m, 2H), 7.84-7.77 (m, 2H), 7.63 (dd, J = 7.8, 1.0 Hz, 1H), 7.50-7.44 (m, 1H), 7.39 (tq, J = 6.4, 3.3, 2.2 Hz, 5H), 2.45 (s, 3H). | $^{13}$C NMR (101 MHz, CDCl$_3$) δ 162.14, 161.14, 157.53, 147.97, 147.30, 140.45, 138.25, 138.04, 137.07, 134.93, 134.58, 130.05, 128.70, 127.89, 126.44, 126.01, 125.24, 125.16, 121.37, 120.17, 119.41, 118.66, 19.58. |
| F34 | 166-169 | IR (thin film) 3290, 3060, 2246, 1652, 1595, 1565, 1513 cm$^{-1}$ | HRMS-FAB (m/z) calcd for C$_{28}$H$_{18}$ClF$_3$N$_4$O$_2$, 534.1070; found, 534.1081. | $^1$H NMR (400 MHz, CDCl$_3$) δ 8.55 (s, 1H), 8.23-8.17 (m, 2H), 7.98 (s, 1H), 7.87-7.74 (m, 6H), 7.60 (d, J = 8.2 Hz, 1H), 7.49-7.35 (m, 7H). | $^{13}$C NMR (101 MHz, CDCl$_3$) δ 164.53, 162.98, 148.38, 141.50, 141.12, 139.02, 138.33, 136.55, 135.55, 133.45, 130.55, 129.83, 129.34, 128.29, 128.19, 127.50, 127.17, 126.72, 122.40, 121.18, 120.09. |
| F35 | 196-199 | IR (thin film) 3135, 1656, 1592, 1541, 1512 cm$^{-1}$ | HRMS-FAB (m/z) calcd for C$_{30}$H$_{21}$F$_5$N$_4$O$_2$, 564.1585; found, 5564.1589. | $^1$H NMR (400 MHz, DMSO-d$_6$) δ 10.47 (s, 1H), 9.40 (s, 1H), 8.10 (dd, J = 8.9, 6.7 Hz, 4H), 8.03-7.93 (m, 4H), 7.67-7.56 (m, 4H), 7.37-7.28 (m, 4H), 2.28 (s, 3H). | $^{13}$C NMR (101 MHz, DMSO-d$_6$) δ 165.39, 161.92, 146.08, 143.72, 141.37, 140.53, 135.87, 134.78, 134.70, 132.22, 130.41, 129.62, 128.40, 127.99, 127.69, 126.57, 126.48, 126.06, 125.41, 123.16, 121.07, 120.38, 20.14; $^{19}$F NMR (376 MHz, DMSO-d$_6$) δ −85.21, −86.92. |
| F36 | 129-133 | IR (thin film) 3291, 3064, 1667, 1605, 1513 cm$^{-1}$ | HRMS-FAB (m/z) calcd for C$_{30}$H$_{18}$F$_8$N$_4$O$_3$, 634.1251; found, 634.1258. | $^1$H NMR (400 MHz, DMSO-d$_6$) δ 10.53 (s, 1H), 9.41 (s, 1H), 8.14-8.03 (m, 6H), 8.01-7.94 (m, 2H), 7.75-7.52 (m, 8H). | $^{13}$C NMR (101 MHz, DMSO-d$_6$) δ 165.13, 161.83, 146.01, 145.21, 143.65, 140.36, 136.21, 135.80, 134.92, 133.85, 132.12, 131.69, 129.77, 128.54, 128.13, 128.03, 127.24, 126.53, 125.40, 123.08, 121.56, 120.99, 120.31; $^{19}$F NMR (376 MHz, DMSO-d6) δ −56.15, −85.21, −86.93. |
| F37 | 120-132 | IR (thin film) 3385, 3264, 3096, 3006, 2838, 2251, 2125, 1656, 1600, 1517 cm$^{-1}$ | HRMS-FAB (m/z) calcd for C$_{29}$H$_{21}$F$_3$N$_4$O$_3$, 530.1566; found, 530.1569. | $^1$H NMR (400 MHz, DMSO-d$_6$) δ 10.35 (s, 1H), 9.40 (s, 1H), 8.12-8.03 (m, 5H), 8.01 (d, J = 2.4 Hz, 1H), 7.98-7.94 (m, 2H), 7.65-7.60 (m, 2H), 7.57 (dd, J = 8.3, 1.3 Hz, 2H), 7.50-7.44 (m, 2H), 7.41-7.35 (m, 1H), 7.28 (d, J = 8.8 Hz, 1H), 3.87 (s, 3H). | $^{13}$C NMR (101 MHz, DMSO-d$_6$) δ 164.79, 161.88, 158.74, 146.97, 143.60, 140.62, 137.42, 135.65, 129.88, 129.33, 129.29, 129.10, 128.00, 127.12, 126.74, 126.46, 125.10, 122.48, 121.24, 120.97, 120.22, 118.69, 111.36, 55.80; $^{19}$F NMR (376 MHz, DMSO-d$_6$) δ −56.97. |
| F38 | 164-172 | IR (thin film) 330, 3063, 2980, 2931, 2246, 1656, 1594, 1514 cm$^{-1}$ | HRMS-FAB (m/z) calcd for C$_{30}$H$_{23}$F$_3$N$_4$O$_3$, 544.1722; found, 544.1730. | $^1$H NMR (400 MHz, CDCl$_3$) δ 8.55 (s, 1H), 8.20 (d, J = 8.7 Hz, 2H), 8.07 (t, J = 1.5 Hz, 1H), 8.01 (s, 1H), 7.87-7.73 (m, 6H), 7.52 (t, J = 7.7 Hz, 1H), 7.36 (ddd, J = 15.4, 7.7, 6.2 Hz, 4H), 7.08-6.96 (m, 2H), 4.07 (q, J = 7.0 Hz, 2H), 1.37 (t, J = 7.0 Hz, 3H). | $^{13}$C NMR (101 MHz, CDCl$_3$) δ 165.86, 163.07, 155.77, 148.33, 141.47, 139.32, 135.57, 134.56, 133.17, 130.76, 129.48, 129.23, 128.45, 128.01, 127.47, 126.39, 125.57, 122.38, 121.67, 121.16, 120.97, 119.91, 119.10, 112.56, 64.03, 14.86; $^{19}$F NMR (376 MHz, CDCl$_3$) δ −58.01. |
| F39 | | IR (thin film) 3295, 3066, 1655, 1591, 1515 cm$^{-1}$ | HRMS-FAB (m/z) calcd for C$_{29}$H$_{20}$F$_4$N$_4$O$_2$, 532.1522; found, 532.1519. | $^1$H NMR (400 MHz, CDCl$_3$) δ 8.56 (s, 1H), 8.20 (d, J = 8.8 Hz, 2H), 8.01 (s, 1H), 7.83-7.75 (m, 4H), 7.64-7.57 (m, 2H), 7.41-7.36 | $^{13}$C NMR (101 MHz, CDCl$_3$) δ 171.22, 164.36, 163.79, 162.96, 161.32, 148.38, 148.36, 144.97, 144.89, 141.51, 139.53, 138.97, 136.83, 136.76, 135.53, 135.19, 130.64, 129.49, 128.28, 127.50, 126.75, 126.08, 123.33, 123.31, 122.40, |

TABLE 4-continued

Analytical Data for Compounds in Table 3.

| No. | Mp (° C.) | IR (cm$^{-1}$) | Mass (m/z) | $^1$H NMR | $^{13}$CNMR; $^{19}$F NMR |
|---|---|---|---|---|---|
| | | | | (m, 2H), 7.34-7.21 (m, 5H), 2.29 (s, 3H). | 121.19, 120.11, 119.87, 119.66, 115.83, 113.12, 112.89, 20.36; $^{19}$F NMR (376 MHz, CDCl$_3$) δ −58.02, −111.56. |
| F40 | 200-205 | IR (thin film) 3301, 3122, 1666, 1600, 1515 cm$^{-1}$ | HRMS-FAB (m/z) calcd for C$_{29}$H$_{18}$F$_6$N$_4$O$_2$, 568.1334; found, 568.1342. | $^1$H NMR (400 MHz, DMSO-d$_6$) δ 10.52 (s, 1H), 9.40 (s, 1H), 8.19 (dd, J = 7.5, 2.4 Hz, 1H), 8.15-8.01 (m, 5H), 7.96 (d, J = 8.9 Hz, 2H), 7.70-7.59 (m, 4H), 7.59-7.44 (m, 4H). | $^{13}$C NMR (101 MHz, DMSO-d$_6$) δ 164.37, 162.16, 161.87, 159.66, 146.05, 143.69, 140.36, 135.83, 134.39, 131.45, 131.41, 130.48, 130.44, 129.58, 129.49, 128.93, 128.90, 128.70, 128.24, 128.17, 128.03, 126.58, 125.46, 123.13, 121.03, 120.37, 116.53, 116.29; $^{19}$F NMR (376 MHz,DMSO-d6) δ −85.22, −86.93, −113.91. |
| F41 | 177-184 | IR (thin film) 3251, 3060, 2252, 1594, 1514 cm$^{-1}$ | HRMS-FAB (m/z) calcd for C$_{30}$H$_{21}$F$_3$N$_4$O$_3$, 542.1566; found, 542.1562. | $^1$H NMR (400 MHz, DMSO-d$_6$) δ 10.51 (s, 1H), 9.40 (s, 1H), 8.13-8.06 (m, 4H), 8.02 (dt, J = 7.7, 1.3 Hz, 1H), 7.99-7.95 (m, 3H), 7.74-7.70 (m, 1H), 7.68-7.59 (m, 4H), 7.58-7.50 (m, 3H), 2.27 (s, 3H). | $^{13}$C NMR (101 MHz, DMSO-d$_6$) δ 202.70, 165.13, 161.81, 146.98, 143.63, 140.60, 140.35, 139.93, 139.20, 135.64, 134.82, 131.84, 130.97, 130.56, 128.55, 128.00, 127.76, 127.58, 126.86, 126.50, 125.38, 122.49, 120.98, 120.30, 30.16; $^{19}$F NMR (376 MHz, DMSO-d6) δ −56.96. |
| F42 | 134-138 | IR (thin film) 3255, 3063, 2250, 2125, 1669, 1592, 1533, 1513 cm$^{-1}$ | HRMS-FAB (m/z) calcd for C$_{30}$H$_{20}$F$_6$N$_4$O$_2$, 582.1490; found, 582.1452. | $^1$H NMR (400 MHz, DMSO-d$_6$) δ 10.52 (s, 1H), 9.41 (s, 1H), 8.16-8.05 (m, 4H), 8.00-7.93 (m, 2H), 7.88-7.78 (m, 2H), 7.62 (d, J = 9.1 Hz, 2H), 7.50 (ddd, J = 9.5, 2.5, 1.4 Hz, 1H), 7.38-7.30 (m, 4H), 2.29 (s, 3H). | $^{13}$C NMR (101 MHz, DMSO-d$_6$) δ 163.92, 162.88, 161.80, 160.44, 146.01, 143.76, 143.68, 140.13, 139.27, 136.73, 135.80, 134.80, 130.44, 129.50, 128.05, 126.53, 126.04, 125.58, 124.29, 123.08, 120.98, 120.40, 119.12, 118.91, 113.29, 113.06, 19.98; $^{19}$F NMR (376 MHz, DMSO-d6) δ −85.23, −86.94, −112.72. |
| F43 | >200 (dec.) | IR (thin film) 3298, 3119, 2919, 1648, 1595, 1582, 1570, 1549, 1516 cm$^{-1}$ | HRMS-FAB (m/z) calcd for C$_{28}$H$_{18}$ClF$_3$N$_4$O$_2$, 534.1070; found, 534.1087. | $^1$H NMR (400 MHz, CDCl$_3$) δ 8.56 (s, 1H), 8.24-8.19 (m, 2H), 8.02 (s, 1H), 7.96 (t, J = 1.6 Hz, 1H), 7.83-7.77 (m, 5H), 7.74 (t, J = 1.8 Hz, 1H), 7.62-7.57 (m, 2H), 7.52-7.36 (m, 5H). | $^{13}$C NMR (101 MHz, CDCl$_3$) δ 164.40, 162.97, 148.38, 148.36, 143.75, 141.50, 138.93, 138.69, 137.00, 135.54, 135.35, 130.49, 129.10, 128.51, 127.51, 127.16, 126.83, 125.75, 124.11, 122.40, 121.17, 120.16. |
| F44 | 195-202 | IR (thin film) 3251, 3068, 2838, 1667, 1598, 1515 cm$^{-1}$ | HRMS-FAB (m/z) calcd for C$_{29}$H$_{20}$F$_4$N$_4$O$_3$, 548.1472; found, 548.1470. | $^1$H NMR (400 MHz, DMSO-d$_6$) δ 10.45 (s, 1H), 9.40 (s, 1H), 8.13-8.01 (m, 6H), 7.95 (d, J = 8.8 Hz, 2H), 7.63 (d, J = 8.3 Hz, 2H), 7.50-7.40 (m, 2H), 7.35 (dd, J = 7.5, 1.7 Hz, 1H), 7.17 (d, J = 7.8 Hz, 1H), 7.10 (td, J = 7.4, 1.0 Hz, 1H), 3.78 (s, 3H). | $^{13}$C NMR (101 MHz, DMSO-d$_6$) δ 164.39, 162.65, 161.87, 160.14, 156.51, 147.04, 143.68, 140.42, 135.70, 131.44, 130.91, 130.75, 130.04, 129.49, 126.56, 125.94, 125.77, 125.41, 123.52, 122.55, 121.03, 120.51, 120.31, 115.67, 115.44, 111.38, 55.52; $^{19}$F NMR (376 MHz, DMSO-d6) δ −56.97, −109.17. |
| F45 | 185-194 | IR (thin film) 3299, 3062, 2247, 1654, 1594, 1513 cm$^{-1}$ | HRMS-FAB (m/z) calcd for C$_{29}$H$_{19}$F$_5$N$_4$O$_2$, 550.1428; found, 550.1431. | $^1$H NMR (400 MHz, CDCl$_3$) δ 8.56 (s, 1H), 8.24-8.19 (m, 2H), 8.10 (t, J = 1.7 Hz, 1H), 8.03 (s, 1H), 7.87-7.76 (m, 6H), 7.66-7.61 (m, 2H), 7.57 (t, J = 7.8 Hz, 1H), 7.51-7.45 (m, 2H), 7.43-7.37 (m, 3H). | $^{13}$C NMR (101 MHz, CDCl$_3$) δ 165.68, 163.07, 147.51, 142.05, 141.50, 140.03, 139.29, 135.73, 135.44, 130.67, 129.31, 128.97, 127.93, 127.50, 127.22, 126.54, 125.93, 125.68, 123.07, 121.15, 120.04; $^{19}$F NMR (376 MHz, CDCl$_3$) δ −85.89, −87.83. |
| F46 | | IR (thin film) 2950, 1673, 1596, 1515 cm$^{-1}$ | HRMS-FAB (m/z) calcd for C$_{30}$H$_{23}$F$_3$N$_4$OS, 544.1545; found, 544.1557. | $^1$H NMR (400 MHz, CDCl$_3$) δ 9.15 (s, 1H), 8.68 (s, 1H), 8.24 (s, 2H), 8.02-7.85 (m, 3H), 7.80 (d, J = 9.0 Hz, 2H), 7.69 (s, 1H), 7.52 (s, 1H), 7.44-7.30 (m, 2H), 7.22-7.08 (m, 3H), 6.95 (dd, J = 8.8, 3.2 Hz, 1H), 2.06 (d, J = 10.4 Hz, 6H). | $^{13}$C NMR (101 MHz, CDCl$_3$) δ 148.54, 141.76, 140.51, 140.31, 135.95, 135.38, 132.74, 132.61, 132.21, 128.93, 127.51, 127.48, 127.39, 125.36, 123.49, 122.42, 121.28, 113.79, 113.63, 55.39; $^{19}$F NMR (376 MHz, CDCl$_3$) δ −58.01. |
| F47 | 207-212 | IR (thin film) 3345, 3095, 1688, 1613, 1586, 1514 cm$^{-1}$ | HRMS-FAB (m/z) calcd for C$_{28}$H$_{18}$F$_5$N$_5$O$_2$, 551.1381; found, 551.1379. | $^1$H NMR (400 MHz, DMSO-d$_6$) δ 10.70 (s, 1H), 9.42 (s, 1H), 8.42-8.35 (m, 2H), 8.27 (dd, J = 7.3, 1.7 Hz, 1H), 8.21-8.06 (m, 8H), 7.67-7.49 (m, 5H). | $^{13}$C NMR (101 MHz, DMSO-d$_6$) δ 162.74, 161.88, 155.29, 149.72, 146.09, 143.75, 139.46, 139.15, 137.44, 135.86, 129.67, 128.82, 127.28, 126.61, 125.82, 123.37, 123.15, 121.10, 120.73; $^{19}$F NMR (376 MHz, DMSO-d6) δ −85.21, −86.92. |
| F48 | 186-196 | IR (thin film) 3332, 3118, 1674, 1610, 1554, 1535, 1515 cm$^{-1}$ | HRMS-FAB (m/z) calcd for C$_{28}$H$_{18}$F$_4$N$_4$O$_2$, 518.1366; found, 518.1365. | $^1$H NMR (400 MHz, CDCl$_3$) δ 8.67-8.56 (m, 2H), 8.42 (dd, J = 7.6, 2.5 Hz, 1H), 8.22 (d, J = 8.7 Hz, 2H), 7.82 (t, J = 8.9 Hz, 4H), 7.74 (ddt, J = 7.5, 4.8, 2.5 Hz, 1H), 7.64-7.57 (m, 2H), 7.47 (t, J = 7.5 Hz, 2H), 7.42-7.35 (m, 3H), 7.31-7.23 (m, 1H). | $^{13}$C NMR (101 MHz, CDCl$_3$) δ 162.98, 161.21, 161.17, 161.09, 158.64, 148.37, 141.53, 139.07, 138.97, 138.51, 135.55, 132.35, 132.26, 130.74, 128.98, 127.89, 127.48, 127.05, 126.70, 122.40, 121.19, 120.40, 116.78, 116.53; $^{19}$F NMR (376 MHz, CDCl$_3$) δ −58.01, −116.01. |

TABLE 4-continued

Analytical Data for Compounds in Table 3.

| No. | Mp (° C.) | IR (cm$^{-1}$) | Mass (m/z) | $^1$H NMR | $^{13}$CNMR; $^{19}$F NMR |
|---|---|---|---|---|---|
| F49 | 140-143 | IR (thin film) 3292, 3116, 2956, 2835, 2247, 1655, 1605, 1514 cm$^{-1}$ | HRMS-FAB (m/z) calcd for C$_{30}$H$_{23}$F$_3$N$_4$O$_3$, 544.1722; found, 544.1750. | $^1$H NMR (400 MHz, CDCl$_3$) δ 8.55 (s, 1H), 8.20 (d, J = 8.8 Hz, 2H), 8.00 (s, 1H), 7.87-7.76 (m, 6H), 7.56-7.47 (m, 2H), 7.42-7.35 (m, 2H), 7.18 (d, J = 8.3 Hz, 1H), 6.86-6.79 (m, 2H), 3.85 (s, 3H), 2.27 (s, 3H). | $^{13}$C NMR (101 MHz, CDCl$_3$) δ 165.69, 163.04, 159.14, 148.35, 142.42, 141.48, 139.31, 136.75, 135.56, 134.75, 133.32, 133.02, 130.79, 128.63, 127.93, 127.47, 126.48, 125.25, 122.39, 121.67, 121.17, 119.97, 115.88, 111.30, 55.29, 20.75. |
| F50 | 147-152 | IR (thin film) 3302, 1642, 1538, 1515, 1247, 1206, 1162, 1024 cm$^{-1}$ | HRMS-FAB (m/z) calcd for C$_{31}$H$_{25}$F$_3$N$_4$O$_3$, 558.1879; found, 558.1883. | $^1$H NMR (400 MHz, DMSO-d$_6$) δ 9.39 (s, 1H), 8.63 (t, J = 5.6 Hz, 1H), 8.10-8.01 (m, 4H), 7.91 (t, J = 1.6 Hz, 1H), 7.78 (dt, J = 7.7, 1.4 Hz, 1H), 7.65-7.59 (m, 3H), 7.49 (t, J = 7.7 Hz, 1H), 7.44-7.30 (m, 4H), 7.16-7.11 (m, 1H), 7.05 (td, J = 7.4, 1.0 Hz, 1H), 3.77 (s, 3H), 3.56 (q, J = 6.9 Hz, 2H), 2.94 (t, J = 7.2 Hz, 2H). | $^{13}$C NMR (101 MHz, DMSO-d$_6$) δ 166.18, 162.08, 156.05, 147.05, 143.69, 141.34, 138.13, 135.68, 134.47, 131.91, 130.42, 129.21, 129.15, 128.11, 127.89, 126.10, 125.63, 122.55, 121.28, 121.05, 120.74, 118.73, 111.69, 55.48, 40.61, 34.91; $^{19}$F NMR (376 MHz, DMSO-d$_6$) δ −56.98. |
| F51 | 184-187 | IR (thin film) 3303, 1626, 1607, 1541, 1517, 1279, 1255, 1209, 1165 cm$^{-1}$ | ESIMS m/z 547 ([M + H]$^+$) | $^1$H NMR (400 MHz, CDCl$_3$) δ 8.55 (s, 1H), 8.17-8.12 (m, 2H), 7.85-7.76 (m, 3H), 7.64 (ddd, J = 8.5, 4.6, 2.4 Hz, 1H), 7.53 (dt, J = 8.1, 1.4 Hz, 2H), 7.46-7.41 (m, 2H), 7.40-7.33 (m, 5H), 7.17 (dd, J = 10.1, 8.5 Hz, 1H), 6.21 (t, J = 5.6 Hz, 1H), 3.76 (q, J = 6.8 Hz, 2H), 3.01 (t, J = 6.8 Hz, 2H). | $^{13}$C NMR (101 MHz, CDCl$_3$) δ 166.50, 163.26, 162.84, 160.32, 148.37, 141.51, 140.63, 135.53, 134.75, 131.07, 131.03, 129.98, 129.94, 129.44, 129.30, 129.22, 128.98, 128.95, 128.85, 128.56, 128.12, 127.67, 127.58, 126.95, 122.40, 121.67, 121.17, 119.10, 116.54, 116.31, 41.11, 35.59; $^{19}$F NMR (376 MHz, CDCl$_3$) δ −58.02, −113.22. |
| F52 | 142-146 | IR (thin layer) 3313, 1641, 1538, 1516, 1247, 1207, 1162 cm$^{-1}$ | HRMS-FAB (m/z) calcd for C$_{32}$H$_{28}$F$_3$N$_5$O$_2$, 571.2195; found, 571.2222. | $^1$H NMR (400 MHz, CDCl$_3$) δ 8.55 (s, 1H), 8.14 (d, J = 8.2 Hz, 2H), 7.92 (t, J = 1.6 Hz, 1H), 7.79 (d, J = 9.0 Hz, 2H), 7.72 (d, J = 7.7 Hz, 1H), 7.64 (d, J = 7.8 Hz, 1H), 7.44 (d, J = 7.7 Hz, 1H), 7.42-7.33 (m, 4H), 7.30-7.23 (m, 1H), 7.20 (dd, J = 7.5, 1.6 Hz, 1H), 7.05-6.98 (m, 2H), 6.24 (t, J = 5.7 Hz, 1H), 3.78 (q, J = 6.7 Hz, 2H), 3.01 (t, J = 6.9 Hz, 2H), 2.51 (s, 6H). | $^{13}$C NMR (101 MHz, CDCl$_3$) δ 167.67, 163.30, 151.22, 148.37, 142.35, 141.49, 140.76, 135.56, 134.70, 133.04, 131.79, 131.59, 129.21, 128.77, 128.63, 128.49, 126.92, 125.07, 122.39, 121.66, 121.16, 117.73, 43.44, 41.04, 35.67; $^{19}$F NMR (376 MHz, CDCl$_3$) δ −58.02. |
| F53 | 91-111 | IR (thin film) 3317, 1643, 1592, 1540, 1516, 1261, 1208 cm$^{-1}$ | HRMS-FAB (m/z) calcd for C$_{31}$H$_{42}$F$_4$N$_4$O$_2$, 560.1835; found, 560.1841. | $^1$H NMR (400 MHz, CDCl$_3$) δ 8.57 (s, 1H), 8.16-8.11 (m, 2H), 7.83-7.77 (m, 2H), 7.44-7.32 (m, 6H), 7.29-7.20 (m, 3H), 7.20-7.13 (m, 2H), 6.20 (t, J = 5.6 Hz, 1H), 3.76 (q, J = 6.8 Hz, 2H), 3.01 (t, J = 6.9 Hz, 2H), 2.24 (s, 3H). | $^{13}$C NMR (101 MHz, CDCl$_3$) δ 166.28, 163.64, 163.20, 161.18, 148.40, 144.64, 144.56, 141.53, 140.50, 139.68, 139.66, 136.58, 136.51, 135.53, 135.14, 130.55, 129.51, 129.18, 128.83, 128.09, 126.97, 125.99, 123.25, 123.22, 122.40, 121.19, 119.34, 119.13, 112.73, 112.50, 20.33; $^{19}$F NMR (376 MHz, CDCl$_3$) δ −58.02, −112.20. |
| F54 | | | ESIMS m/z 577 ([M + H]$^+$) | $^1$H NMR (400 MHz, CDCl$_3$) δ 8.56 (s, 1H), 8.18-8.11 (m, 2H), 7.80 (d, J = 9.1 Hz, 2H), 7.75-7.65 (m, 2H), 7.42-7.32 (m, 5H), 7.25 (d, J = 6.8 Hz, 1H), 7.18-7.10 (m, 1H), 7.06-6.95 (m, 2H), 6.16 (t, J = 5.7 Hz, 1H), 3.81-3.71 (m, 5H), 3.00 (t, J = 6.9 Hz, 2H). | $^{19}$F NMR (376 MHz, CDCl$_3$) δ −58.02, −109.14. |
| F55 | 157-162 | IR (thin film) 3301, 1628, 1517, 1253, 1207, 1165 cm$^{-1}$ | HRMS-FAB (m/z) calcd for C$_{30}$H$_{21}$F$_5$N$_4$O$_2$, 564.1585; found, 564.1586. | $^1$H NMR (400 MHz, DMSO-d$_6$) δ 9.39 (s, 1H), 8.71 (t, J = 5.5 Hz, 1H), 8.10-8.01 (m, 4H), 8.00-7.92 (m, 2H), 7.62 (d, J = 8.4 Hz, 2H), 7.53 (tdd, J = 7.6, 3.2, 1.4 Hz, 2H), 7.48-7.33 (m, 5H), 3.56 (q, J = 6.6 Hz, 2H), 2.93 (t, J = 7.3 Hz, 2H). | $^{13}$C NMR (101 MHz, DMSO-d$_6$) δ 164.78, 162.06, 161.91, 160.31, 159.41, 157.85, 147.05, 143.69, 141.23, 135.67, 131.63, 131.60, 131.14, 131.11, 130.81, 130.72, 130.67, 129.74, 129.65, 129.18, 128.15, 126.12, 124.81, 124.78, 122.65, 122.54, 122.49, 122.28, 122.13, 121.28, 118.73, 115.88, 115.79, 115.65, 115.57, 40.69, 34.88; $^{19}$F NMR (376 MHz, DMSO-d$_6$) δ −56.99, −111.42, −111.47, −114.90, −114.96. |
| F56 | 151-156 | IR (thin film) 2942, 2890, 2866, 1463, | HRMS-FAB (m/z) calcd for C$_{31}$H$_{25}$F$_3$N$_4$O$_3$, 558.1879; found, 558.1883. | $^1$H NMR (400 MHz, CDCl$_3$) δ 8.55 (s, 1H), 8.17-8.11 (m, 2H), 7.83-7.76 (m, 2H), 7.74-7.65 (m, 2H), 7.50 (dd, J = 8.3, 1.3 | $^{13}$C NMR (101 MHz, CDCl$_3$) δ 167.02, 163.32, 158.99, 148.35, 141.49, 140.84, 137.56, 135.56, 129.61, 129.47, 129.24, 128.74, 128.08, 127.76, 127.32, 126.96, 126.91, 122.39, 121.67, |

TABLE 4-continued

Analytical Data for Compounds in Table 3.

| No. | Mp (° C.) | IR (cm$^{-1}$) | Mass (m/z) | $^1$H NMR | $^{13}$CNMR; $^{19}$F NMR |
|---|---|---|---|---|---|
| | | 1380, 1037, 1027 cm$^{-1}$ | | Hz, 2H), 7.44-7.29 (m, 7H), 6.97 (d, J = 8.6 Hz, 1H), 6.17 (t, J = 5.7 Hz, 1H), 3.84 (s, 3H), 3.75 (q, J = 6.8 Hz, 2H), 3.00 (t, J = 6.9 Hz, 2H). | 121.17, 119.10, 110.83, 55.74, 41.03, 35.72; $^{19}$F NMR (376 MHz, CDCl$_3$) δ −58.02. |
| F57 | 180-183 | | ESIMS m/z 515 ([M + H]$^+$) | $^1$H NMR (300 MHz, DMSO-d$_6$) δ 9.39 (s, 1H), 9.25 (t, J = 6.0 Hz, 1H), 8.22 (t, J = 1.7 Hz, 1H), 8.14-7.98 (m, 4H), 7.96-7.81 (m, 2H), 7.80-7.70 (m, 2H), 7.66-7.45 (m, 6H), 7.45-7.34 (m, 1H), 4.60 (d, J = 5.9 Hz, 2H). | |
| F58 | 202-210 | | HRMS-FAB (m/z) calcd for C$_{29}$H$_{20}$F$_4$N$_4$O, 516.1573; found, 516.1572. | $^1$H NMR (400 MHz, CDCl$_3$) δ 8.65 (s, 1H), 8.24-8.18 (m, 2H), 8.00 (s, 1H), 7.91 (d, J = 8.4 Hz, 2H), 7.82-7.75 (m, 4H), 7.63-7.57 (m, 2H), 7.33-7.20 (m, 5H), 2.29 (s, 3H). | $^{19}$F NMR (376 MHz, CDCl$_3$) δ −62.48, −111.52. |
| F59 | 217-222 | | HRMS-FAB (m/z) calcd for C$_{28}$H$_{17}$F$_5$N$_4$O, 520.1323; found, 520.1327. | $^1$H NMR (400 MHz, DMSO-d$_6$) δ 10.51 (s, 1H), 9.53 (s, 1H), 8.20 (d, J = 8.4 Hz, 2H), 8.17-8.09 (m, 4H), 8.02-7.92 (m, 4H), 7.65-7.50 (m, 3H), 7.45-7.35 (m, 2H). | $^{19}$F NMR (376 MHz, DMSO-d$_6$) δ −60.80, −110.30, −114.84. |
| F60 | 183-187 | | HRMS-FAB (m/z) calcd for C$_{29}$H$_{21}$F$_3$N$_4$O$_2$, 514.1617; found, 514.1613. | $^1$H NMR (400 MHz, DMSO-d$_6$) δ 10.49 (s, 1H), 9.53 (s, 1H), 8.20 (d, J = 8.4 Hz, 2H), 8.17-8.10 (m, 2H), 8.08 (t, J = 1.5 Hz, 1H), 8.03-7.91 (m, 5H), 7.72 (dt, J = 7.7, 1.3 Hz, 1H), 7.59 (t, J = 7.7 Hz, 1H), 7.45-7.36 (m, 2H), 7.19-7.14 (m, 1H), 7.09 (td, J = 7.5, 1.0 Hz, 1H), 3.80 (s, 3H). | $^{19}$F NMR (376 MHz, DMSO-d$_6$) δ −60.79. |
| F61 | 203-206 | | HRMS-FAB (m/z) calcd for C$_{29}$H$_{21}$F$_3$N$_4$O$_2$, 514.1617; found 514.1628. | $^1$H NMR (400 MHz, DMSO-d$_6$) δ 10.36 (s, 1H), 9.52 (s, 1H), 8.20 (d, J = 8.4 Hz, 2H), 8.14-8.10 (m, 2H), 8.05 (dd, J = 8.6, 2.4 Hz, 1H), 8.02-7.95 (m, 5H), 7.57 (dd, J = 8.3, 1.3 Hz, 2H), 7.47 (td, J = 6.8, 6.4, 1.6 Hz, 2H), 7.41-7.35 (m, 1H), 7.28 (d, J = 8.8 Hz, 1H), 3.87 (s, 3H). | $^{19}$F NMR (376 MHz, DMSO-d$_6$) δ −60.80. |
| F62 | 212-215 | | HRMS-FAB (m/z) calcd for C$_{28}$H$_{18}$F$_4$N$_4$O, 502.1417; found, 502.1417. | $^1$H NMR (400 MHz, DMSO-d$_6$) δ 10.53 (s, 1H), 9.53 (s, 1H), 8.22-8.17 (m, 3H), 8.15-8.11 (m, 2H), 8.05 (ddd, J = 8.5, 4.8, 2.4 Hz, 1H), 7.98 (t, J = 8.5 Hz, 4H), 7.70-7.65 (m, 2H), 7.58-7.45 (m, 4H). | $^{19}$F NMR (376 MHz, DMSO-d$_6$) δ −60.79, −113.89. |
| F64 | | | HRMS-FAB (m/z) calcd for C$_{31}$H$_{24}$F$_4$N$_4$O$_3$, 576.1785; found, 576.1784. | $^1$H NMR (400 MHz, CDCl$_3$) δ 8.58 (s, 1H), 8.15-8.08 (m, 2H), 7.82-7.76 (m, 2H), 7.42-7.26 (m, 5H), 7.20-7.13 (m, 2H), 6.95-6.87 (m, 4H), 4.03 (q, J = 7.1 Hz, 2H), 3.69 (s, 3H), 1.26 (t, J = 7.1, 1.5 Hz, 3H). | $^{19}$F NMR (400 MHz, CDCl$_3$) δ −58.02, −110.78. |
| F65 | | | HRMS-FAB (m/z) calcd for C$_{32}$H$_{26}$F$_4$N$_4$O$_3$, 590.1941; found, 590.1947. | $^1$H NMR (400 MHz, CDCl$_3$) δ 8.58 (s, 1H), 8.13-8.07 (m, 2H), 7.82-7.76 (m, 2H), 7.42-7.25 (m, 5H), 7.19-7.13 (m, 2H), 6.94-6.85 (m, 4H), 3.98-3.88 (m, 2H), 3.68 (s, 3H), 1.74-1.64 (m, 2H), 0.96 (t, J = 7.4 Hz, 3H). | $^{19}$F NMR (400 MHz, CDCl$_3$) δ −58.03, −110.85. |
| F66 | | | HRMS-FAB (m/z) calcd for C$_{33}$H$_{26}$F$_4$N$_4$O$_3$, 602.1941; found, 602.1941. | $^1$H NMR (400 MHz, CDCl$_3$) δ 8.57 (s, 1H), 8.11 (d, J = 8.6 Hz, 2H), 7.82-7.76 (m, 2H), 7.42-7.26 (m, 5H), 7.22 (d, J = 8.6 Hz, 2H), 6.94-6.85 (m, 4H), 3.90-3.79 (m, 2H), 3.69 (s, 3H), 1.19-1.08 (m, 1H), 0.50-0.41 (m, 2H), 0.20 (d, J = 5.0 Hz, 2H). | $^{19}$F NMR (400 MHz, CDCl$_3$) δ −58.02, −110.87. |

TABLE 4-continued

Analytical Data for Compounds in Table 3.

| No. | Mp (° C.) | IR (cm$^{-1}$) | Mass (m/z) | $^1$H NMR | $^{13}$CNMR; $^{19}$F NMR |
|---|---|---|---|---|---|
| F67 | | | HRMS-FAB (m/z) calcd for C$_{31}$H$_{22}$F$_4$N$_4$O$_4$, 590.1577; found, 590.1578. | $^1$H NMR (400 MHz, CDCl$_3$) (~9:1 mixture of N-Acetyl and O-acetyl) δ 8.58 (s, 1H), 8.23-8.17 (m, 2H), 7.81-7.76 (m, 2H), 7.72-7.63 (m, 2H), 7.42-7.33 (m, 3H), 7.30-7.25 (m, 2H), 7.09-7.02 (m, 2H), 7.01-6.94 (m, 2H), 3.74 (s, 3H), 2.47 (s, 3H). | $^{19}$F NMR (400 MHz, CDCl$_3$) δ −58.02, −106.07. |
| F68 | 179-182 | | HRMS-FAB (m/z) calcd for C$_{21}$H$_{14}$F$_3$N$_5$O, 409.1150; found, 409.1154. | $^1$H NMR (400 MHz, DMSO-d$_6$) δ 10.84 (s, 1H), 9.53 (s, 1H), 8.78 (ddd, J = 4.8, 1.6, 0.9 Hz, 1H), 8.20 (d, J = 8.0 Hz, 3H), 8.16-8.06 (m, 5H), 7.99 (d, J = 8.6 Hz, 2H), 7.71 (ddd, J = 7.6, 4.8, 1.3 Hz, 1H). | $^{19}$F NMR (376 MHz, DMSO-d$_6$) δ −60.80. |

| % Control (or Mortality) | Rating |
|---|---|
| BAW and CL Rating Table | |
| 50-100 | A |
| More than 0-Less than 50 | B |
| Not Tested | C |
| No activity noticed in this bioassay | D |
| GPA & YFM Rating Table | |
| 80-100 | A |
| More than 0-Less than 80 | B |
| Not Tested | C |
| No activity noticed in this bioassay | D |

TABLE ABC

Biological Results

| No. | BAW | CL | GPA | YFM |
|---|---|---|---|---|
| F1 | D | A | C | D |
| F2 | B | D | C | D |
| F3 | D | D | C | D |
| F4 | A | A | C | B |
| F5 | A | A | C | B |
| F6 | D | D | C | D |
| F7 | A | A | C | D |
| F8 | A | A | B | B |
| F9 | A | A | C | A |
| F10 | A | A | C | B |
| F11 | A | A | C | D |
| F12 | A | A | B | A |
| F13 | D | A | C | D |
| F14 | A | A | B | D |
| F15 | D | D | C | D |
| F16 | D | A | C | B |
| F17 | A | A | C | D |
| F18 | D | D | C | D |
| F19 | A | A | C | A |
| F20 | A | A | C | A |
| F21 | A | A | C | A |
| F22 | A | A | C | A |
| F23 | A | A | C | A |
| F24 | A | A | B | D |
| RF25 | A | A | C | D |
| F26 | A | A | C | A |
| F27 | B | D | C | D |
| F28 | A | A | C | A |
| F29 | A | D | C | D |
| F30 | A | A | C | D |
| F31 | A | A | C | D |
| F32 | D | A | C | D |
| F33 | D | A | C | D |
| F34 | A | A | C | D |
| F35 | A | A | C | D |
| F36 | D | A | C | D |
| F37 | A | A | C | A |
| F38 | A | A | B | A |
| F39 | A | A | C | D |
| F40 | D | A | C | D |
| F41 | A | A | C | A |
| F42 | D | A | C | D |
| F43 | A | A | C | D |
| F44 | A | A | C | B |
| F45 | A | A | C | D |
| F46 | B | D | C | D |
| F47 | D | D | C | D |
| F48 | D | A | C | D |
| F49 | A | A | C | B |
| F50 | A | A | C | D |
| F51 | A | D | C | D |
| F52 | A | A | C | A |
| F53 | A | A | C | A |
| F54 | A | A | C | C |
| F55 | A | A | B | D |
| F56 | A | A | C | A |
| F57 | D | A | C | D |
| F58 | A | A | C | D |
| F59 | A | A | D | A |
| F60 | A | A | B | A |
| F61 | A | A | C | A |
| F62 | A | A | C | B |
| F64 | A | A | C | D |
| F65 | A | A | C | D |
| F66 | A | A | C | D |
| F67 | A | A | C | A |
| F68 | B | D | C | D |

We claim:

1. A process comprising applying a molecule of Formula One to a locus to control a pest, in a sufficient amount to control said pest, wherein said pest is Beet Armyworm (*Spodoptera exigua*), Cabbage Looper (*Trichoplusia ni*), Green Peach Aphid (*Myzus persicae*) or Yellow Fever Mosquito (*Aedes aegypti*);

113

Formula One

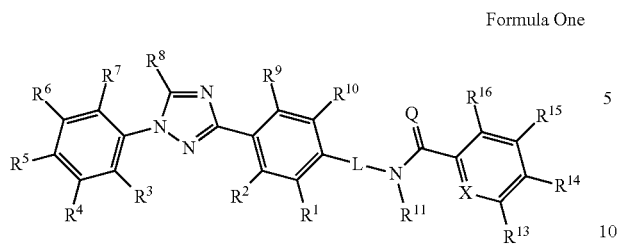

wherein
- (A) $R^1$, $R^2$, $R^3$, $R^4$, $R^5$, $R^6$, $R^7$, $R^9$, $R^{10}$, $R^{14}$, $R^{15}$, and $R^{16}$ is each independently selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, or $C_3$-$C_5$ cycloalkenyloxy,
  wherein each alkyl, alkenyl, alkenyloxy, alkynyl, alkynyloxy, haloalkyl, alkoxy, haloalkoxy, cycloalkyl, cycloalkoxy, cycloalkenyl, or cycloalkenyloxy, are optionally substituted with one or more substituents independently selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_1$-$C_4$ alkynyloxy, $C_1$-$C_4$ haloalkyl, $C_1$-$C_4$ haloalkoxy, $C_3$-$C_6$ cycloalkyl, $C_3$-$C_6$ cycloalkoxy, $C_3$-$C_6$ cycloalkenyl, or $C_3$-$C_6$ cycloalkenyloxy;
- (B) $R^8$ is H;
- (C) L is a linker that is a bond connecting nitrogen to the carbon in the ring;
- (D) $R^{11}$ is selected from H, $(C_1$-$C_4)$alkyl, $(C_2$-$C_4)$alkenyl, $(C_2$-$C_4)$alkenyloxy, $(C_2$-$C_4)$alkynyl, $(C_2$-$C_4)$alkynyloxy, $(C_1$-$C_4)$haloalkyl, $(C_1$-$C_4)$alkoxy, $(C_1$-$C_4)$haloalkoxy, $(C_1$-$C_4)$alkyl $(C_1$-$C_4)$alkoxy, $(C_3$-$C_6)$cycloalkyl, $(C_3$-$C_6)$cycloalkoxy, $(C_3$-$C_6)$cycloalkenyl, $(C_3$-$C_6)$cycloalkenyloxy, $((C_1$-$C_4)$alkyl)) $(C_3$-$C_6)$cycloalkyl), $C(O)(C_1$-$C_4)$alkyl, $C(O)$phenyl, $((C_1$-$C_4)$alkyl)$C(O)(C_1$-$C_4)$alkyl, and $((C_1$-$C_4)$alkyl)$C(O)O((C_1$-$C_4)$alkyl),
  wherein each alkyl, alkenyl, alkenyloxy, alkynyl, alkynyloxy, haloalkyl, alkoxy, haloalkoxy, cycloalkyl, cycloalkoxy, cycloalkenyl, cycloalkenyloxy, and phenyl, are optionally substituted with one or more substituents independently selected from H, F, Cl, Br, I, CN, $NO_2$, OH, oxo, and $OC(O)(C_1$-$C_4)$alkyl;
- (E) X is selected from N or $CR^{12}$, wherein $R^{12}$ is selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, or $C_3$-$C_6$ cycloalkenyloxy;
- (F) $R^{13}$ is selected from a group consisting of H, phenyl, or substituted phenyl,
  wherein said substituted phenyl is substituted with one or more substituents independently selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, $C_3$-$C_6$ cycloalkenyloxy, $OC_1$-$C_4$ alkylphenyl, $C(O)C_1$-$C_4$ alkyl, or $N(C_1$-$C_4$ alkyl)$(C_1$-$C_4$ alkyl); and
- (G) Q is selected from O or S.

114

2. A molecule having a structure of Formula One wherein said molecule is in the form of an agriculturally acceptable acid addition salt, a salt derivative, a solvate, or an ester derivative;

Formula One

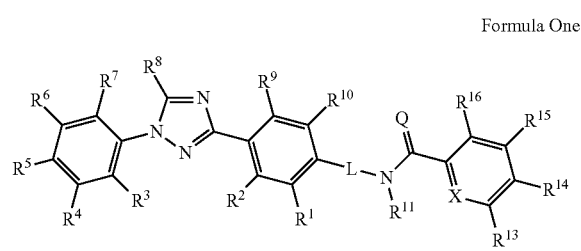

wherein
- (A) $R^1$, $R^2$, $R^3$, $R^4$, $R^5$, $R^6$, $R^7$, $R^9$, $R^{10}$, $R^{14}$, $R^{15}$, and $R^{16}$ is each independently selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, or $C_3$-$C_6$ cycloalkenyloxy,
  wherein each alkyl, alkenyl, alkenyloxy, alkynyl, alkynyloxy, haloalkyl, alkoxy, haloalkoxy, cycloalkyl, cycloalkoxy, cycloalkenyl, or cycloalkenyloxy, are optionally substituted with one or more substituents independently selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, or $C_3$-$C_6$ cycloalkenyloxy;
- (B) $R^8$ is H;
- (C) L is a linker that is a bond connecting nitrogen to the carbon in the ring;
- (D) $R^{11}$ is selected from H, $(C_1$-$C_4)$alkyl, $(C_2$-$C_4)$alkenyl, $(C_2$-$C_4)$alkenyloxy, $(C_2$-$C_4)$alkynyl, $(C_2$-$C_4)$alkynyloxy, $(C_1$-$C_4)$haloalkyl, $(C_1$-$C_4)$alkoxy, $(C_1$-$C_4)$haloalkoxy, $(C_1$-$C_4)$alkyl $(C_1$-$C_4)$alkoxy, $(C_3$-$C_6)$cycloalkyl, $(C_3$-$C_6)$cycloalkoxy, $(C_3$-$C_6)$cycloalkenyl, $(C_3$-$C_6)$cycloalkenyloxy, $((C_1$-$C_4)$alkyl)) $(C_3$-$C_6)$cycloalkyl), $C(O)(C_1$-$C_4)$alkyl, $C(O)$phenyl, $((C_1$-$C_4)$alkyl)$C(O)(C_1$-$C_4)$alkyl, and $((C_1$-$C_4)$alkyl)$C(O)O((C_1$-$C_4)$alkyl),
  wherein each alkyl, alkenyl, alkenyloxy, alkynyl, alkynyloxy, haloalkyl, alkoxy, haloalkoxy, cycloalkyl, cycloalkoxy, cycloalkenyl, cycloalkenyloxy, and phenyl, are optionally substituted with one or more substituents independently selected from H, F, Cl, Br, I, CN, $NO_2$, OH, oxo, and $OC(O)(C_1$-$C_4)$alkyl;
- (E) X is selected from N or $CR^{12}$, wherein $R^{12}$ is selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, or $C_3$-$C_6$ cycloalkenyloxy;
- (F) $R^{13}$ is selected from a group consisting of H, phenyl, or substituted phenyl,
  wherein said substituted phenyl is substituted with one or more substituents independently selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, $C_3$-$C_6$ cycloalkenyloxy, $OC_1$-$C_4$ alkylphenyl, $C(O)C_1$-$C_4$ alkyl, or $N(C_1$-$C_4$ alkyl)($C_1$-$C_4$ alkyl); and (G) Q is selected from O or S.

3. A pesticidal composition comprising a molecule of Formula One and a carrier in the form of a seed dressing;

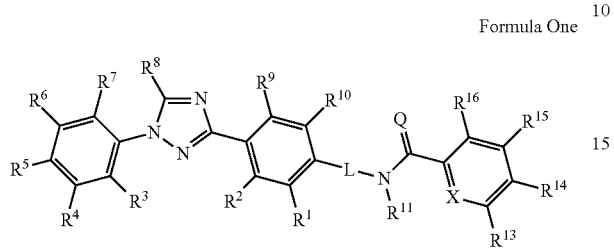

Formula One wherein (A) $R^1$, $R^2$, $R^3$, $R^4$, $R^5$, $R^6$, $R^7$, $R^9$, $R^{10}$, $R^{14}$, $R^{15}$, and $R^{16}$ is each independently selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, or $C_3$-$C_5$ cycloalkenyloxy, wherein each alkyl, alkenyl, alkenyloxy, alkynyl, alkynyloxy, haloalkyl, alkoxy, haloalkoxy, cycloalkyl, cycloalkoxy, cycloalkenyl, or cycloalkenyloxy, are optionally substituted with one or more substituents independently selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, or $C_3$-$C_6$ cycloalkenyloxy;

(B) $R^8$ is H;

(C) L is a linker that is a bond connecting nitrogen to the carbon in the ring;

(D) $R^{11}$ is selected from H, $(C_1$-$C_4)$alkyl, $(C_2$-$C_4)$ alkenyl, $(C_2$-$C_4)$alkenyloxy, $(C_2$-$C_4)$alkynyl, $(C_2$-$C_4)$ alkynyloxy, $(C_1$-$C_4)$haloalkyl, $(C_1$-$C_4)$alkoxy, $(C_1$-$C_4)$haloalkoxy, $(C_1$-$C_4)$alkyl $(C_1$-$C_4)$alkoxy, $(C_3$-$C_6)$ cycloalkyl, $(C_3$-$C_6)$cycloalkoxy, $(C_3$-$C_6)$ cycloalkenyl, $(C_3$-$C_6)$cycloalkenyloxy, $((C_1$-$C_4)$ alkyl)) $(C_3$-$C_6)$cycloalkyl), $C(O)(C_1$-$C_4)$alkyl, $C(O)$ phenyl, $((C_1$-$C_4)$alkyl)$C(O)(C_1$-$C_4)$alkyl, and $((C_1$-$C_4)$alkyl)$C(O)O((C_1$-$C_4)$alkyl), wherein each alkyl, alkenyl, alkenyloxy, alkynyl, alkynyloxy, haloalkyl, alkoxy, haloalkoxy, cycloalkyl, cycloalkoxy, cycloalkenyl, cycloalkenyloxy, and phenyl, are optionally substituted with one or more substituents independently selected from H, F, Cl, Br, I, CN, $NO_2$, OH, oxo, and $OC(O)(C_1$-$C_4)$alkyl;

(E) X is selected from N or $CR^{12}$, wherein $R^{12}$ is selected from a group consisting of H, F, Cl, Br, I, CN, $NO_2$, OH, $C_2$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, or $C_3$-$C_6$ cycloalkenyloxy;

(F) $R^{13}$ is selected from a group consisting of H, phenyl, or substituted phenyl, wherein said substituted phenyl is substituted with one or more substituents independently selected from a group consisting of H, F, Cl, Br, I, CN, $NO_2$, OH, $C_1$-$C_4$ alkyl, $C_2$-$C_4$ alkenyl, $C_2$-$C_4$ alkenyloxy, $C_2$-$C_4$ alkynyl, $C_2$-$C_4$ alkynyloxy, $C_1$-$C_4$ haloalkyl, $C_1$-$C_4$ alkoxy, $C_1$-$C_4$ haloalkoxy, $C_3$-$C_6$ cycloalkyl, $C_3$-$C_6$ cycloalkoxy, $C_3$-$C_6$ cycloalkenyl, $C_3$-$C_6$ cycloalkenyloxy, $OC_1$-$C_4$ alkylphenyl, $C(O)C_1$-$C_4$ alkyl, or $N(C_1$-$C_4$ alkyl)($C_1$-$C_4$ alkyl); and (G) Q is selected from O or S.

* * * * *